(12) United States Patent
Yaghi et al.

(10) Patent No.: US 8,946,454 B2
(45) Date of Patent: Feb. 3, 2015

(54) CHEMICAL FRAMEWORK COMPOSITIONS AND METHODS OF USE

(75) Inventors: Omar M. Yaghi, Los Angeles, CA (US); Qiaowei Li, Los Angeles, CA (US); Ognjen S. Miljanic, Houston, TX (US); Wenyu Zhang, Los Angeles, CA (US); James Fraser Stoddart, Evanston, IL (US)

(73) Assignee: The Regents of the University of California, Oakland, CA (US)

( * ) Notice: Subject to any disclaimer, the term of this patent is extended or adjusted under 35 U.S.C. 154(b) by 661 days.

(21) Appl. No.: 12/996,378

(22) PCT Filed: Jun. 5, 2009

(86) PCT No.: PCT/US2009/046463
§ 371 (c)(1),
(2), (4) Date: Feb. 18, 2011

(87) PCT Pub. No.: WO2009/149381
PCT Pub. Date: Dec. 10, 2009

(65) Prior Publication Data
US 2011/0137025 A1    Jun. 9, 2011

Related U.S. Application Data

(60) Provisional application No. 61/059,224, filed on Jun. 5, 2008.

(51) Int. Cl.
| | | |
|---|---|---|
| *C07D 495/06* | (2006.01) | |
| *C07D 495/08* | (2006.01) | |
| *C07F 3/00* | (2006.01) | |
| *B01J 20/22* | (2006.01) | |
| *C07D 323/00* | (2006.01) | |
| *C07D 339/06* | (2006.01) | |
| *C07D 471/22* | (2006.01) | |
| *C07D 493/04* | (2006.01) | |
| *C07D 495/04* | (2006.01) | |
| *C07D 497/18* | (2006.01) | |

(52) U.S. Cl.
CPC .............. *C07F 3/003* (2013.01); *B01J 20/226* (2013.01); *C07D 323/00* (2013.01); *C07D 339/06* (2013.01); *C07D 471/22* (2013.01); *C07D 493/04* (2013.01); *C07D 495/04* (2013.01); *C07D 497/18* (2013.01); *B01D 2253/204* (2013.01)
USPC ........................................................ 549/351

(58) Field of Classification Search
None
See application file for complete search history.

(56) References Cited

U.S. PATENT DOCUMENTS

| | | |
|---|---|---|
| 4,532,225 A | 7/1985 | Tsao et al. |
| 5,160,500 A | 11/1992 | Chu et al. |
| 5,208,335 A | 5/1993 | Ramprasad et al. |
| 5,648,508 A | 7/1997 | Yaghi |
| 6,501,000 B1 | 12/2002 | Stilbrany et al. |
| 6,617,467 B1 | 9/2003 | Muller et al. |
| 6,624,318 B1 | 9/2003 | Muller et al. |
| 6,893,564 B2 | 5/2005 | Muller et al. |
| 6,929,679 B2 | 8/2005 | Mueller et al. |
| 6,930,193 B2 | 8/2005 | Yaghi et al. |
| 7,196,210 B2 | 3/2007 | Yaghi et al. |
| 7,202,385 B2 | 4/2007 | Yaghi et al. |
| 7,279,517 B2 | 10/2007 | Mueller et al. |
| 7,309,380 B2 | 12/2007 | Muller et al. |
| 7,343,747 B2 | 3/2008 | Muller et al. |
| 7,411,081 B2 | 8/2008 | Mueller et al. |
| 7,524,444 B2 | 4/2009 | Hesse et al. |
| 7,582,798 B2 | 9/2009 | Yaghi et al. |
| 7,652,132 B2 | 1/2010 | Yaghi et al. |
| 7,662,746 B2 | 2/2010 | Yaghi et al. |
| 7,799,120 B2 | 9/2010 | Yaghi et al. |
| 7,815,716 B2 | 10/2010 | Mueller et al. |
| 2003/0004364 A1 | 1/2003 | Yaghi et al. |
| 2003/0078311 A1 | 4/2003 | Muller et al. |
| 2003/0148165 A1 | 8/2003 | Muller et al. |
| 2003/0222023 A1 | 12/2003 | Mueller et al. |
| 2004/0081611 A1 | 4/2004 | Muller et al. |
| 2004/0225134 A1 | 11/2004 | Yaghi et al. |
| 2004/0249189 A1 | 12/2004 | Mueller et al. |
| 2004/0265670 A1 | 12/2004 | Muller et al. |
| 2005/0004404 A1 | 1/2005 | Muller et al. |
| 2005/0014371 A1 | 1/2005 | Tsapatsis |
| 2005/0124819 A1 | 6/2005 | Yaghi et al. |
| 2005/0154222 A1 | 7/2005 | Muller et al. |
| 2005/0192175 A1 | 9/2005 | Yaghi et al. |
| 2006/0057057 A1 | 3/2006 | Muller et al. |
| 2006/0135824 A1 | 6/2006 | Mueller et al. |
| 2006/0154807 A1 | 7/2006 | Yaghi et al. |
| 2006/0185388 A1 | 8/2006 | Muller et al. |

(Continued)

FOREIGN PATENT DOCUMENTS

DE    102005023856 A1    11/2006
DE    102005054523 A1    5/2007

(Continued)

OTHER PUBLICATIONS

Butler. Tetrahedron Letters, 2004, 45, 467-72.*
"IUPAC Gold Book-macrocycle". http://goldbook.iupac.org/M03662.html, accessed Jan. 30, 2014.*
Liu. Journal of Organic Chemistry, 2005, 70, 9334-44.*
"IUPAC Gold Book-cryptand", http://goldbook.iupac.org/C01426.html, accessed Jan. 30, 2014.*
Deska. ARKIVOC, 2013, i, 185-242.*

(Continued)

*Primary Examiner* — Noble Jarrell
(74) *Attorney, Agent, or Firm* — Joseph R. Baker, Jr.; Gavrilovich, Dodd & Lindsey LLP

(57) ABSTRACT

The disclosure provides metal organic frameworks useful for sensing, gas sorption, microelectronics and switches.

16 Claims, 42 Drawing Sheets

(56) References Cited

U.S. PATENT DOCUMENTS

| | | |
|---|---|---|
| 2006/0252641 A1 | 11/2006 | Yaghi et al. |
| 2006/0252972 A1 | 11/2006 | Pilliod et al. |
| 2006/0287190 A1 | 12/2006 | Eddaoudi et al. |
| 2007/0068389 A1 | 3/2007 | Yaghi et al. |
| 2007/0202038 A1 | 8/2007 | Yaghi et al. |
| 2008/0184883 A1 | 8/2008 | Zhou et al. |
| 2009/0155588 A1 | 6/2009 | Hesse et al. |
| 2010/0132549 A1 | 6/2010 | Yaghi et al. |
| 2010/0143693 A1 | 6/2010 | Yaghi et al. |
| 2010/0186588 A1 | 7/2010 | Yaghi et al. |
| 2010/0286022 A1 | 11/2010 | Yaghi et al. |

FOREIGN PATENT DOCUMENTS

| | | |
|---|---|---|
| EP | 1674555 A1 | 6/2006 |
| WO | 2004101575 A2 | 11/2004 |
| WO | 2006072573 A2 | 7/2006 |
| WO | 2006116340 A1 | 11/2006 |
| WO | 2007101241 A2 | 9/2007 |
| WO | 2007111739 A2 | 10/2007 |
| WO | 2008091976 A1 | 7/2008 |
| WO | 2008138989 A1 | 11/2008 |
| WO | 2008140788 A1 | 11/2008 |
| WO | 2009020745 A9 | 2/2009 |
| WO | 2009042802 A1 | 4/2009 |
| WO | 2010078337 A1 | 7/2010 |
| WO | 2010080618 A1 | 7/2010 |
| WO | 2010083418 A1 | 7/2010 |
| WO | 2010088629 A1 | 8/2010 |
| WO | 2010090683 A1 | 8/2010 |
| WO | 2010148276 A3 | 12/2010 |
| WO | 2010148296 A3 | 12/2010 |
| WO | 2010148374 A3 | 12/2010 |
| WO | 2011014503 A1 | 2/2011 |
| WO | 2011038208 A2 | 3/2011 |

OTHER PUBLICATIONS

Deska. ARKIVOC, 2013, i, 66-100.*
Chambron. Pure and Applied Chemistry, 1990, 62(6), 1027-34.*
Niu et al., "Synthesis and structural characterization of the one dimensional polymers [Rh2(OAc)4(NCPhCN)S, S=CH3COCH3, CH3OH, C2H5OH, C4H8O, and C6H6," Polyhedron 17(23-24):4079-89 (1998).
Oisaki et al., "A Metal-Organic Framework with Covalently Bound Organometallic Complexes," J. Am. Chem. Soc. 132:9262-9264 (2010).
O'Keefe et al., "Structural Study of New Hydrocarbon Nano-Crystals by Energy-Filtered Electron Diffraction," Ultramicroscopy 98:145-150 (2004).
O'Keefe et al., "Germanate Zeolites: Contrasting the Behavior of Germanate and Silicate Structures Built from Cubic T8O20 units (T=Si or Ge)," Chem. Eur. J. 5:2796-2801 (1999).
O'Keefe et al., "Frameworks for Extended Solids: Geometrical Design Principles," J. Solid State Chem. 152:3-20 (2000).
Okeeffe et al., "Reticular Chemistry—Present and Future Prospects—Introduction," J. Solid State Chem.178:V-VI (2005).
O'Keeffe et al., "The Reticular Chemistry Structure Resource (RCSR) Database of, and Symbols for, Crystal Nets," Acc. Chem. Res. 41:1782-1789 (2008).
Park, Kyo Sung et al., "Exceptional chemical and thermal stability of zeolitic imidazolate frameworks," Proc. Natl. Acad. Sci., Jul. 5, 2006, pp. 10186-10191, vol. 103, No. 27.
Park, Jae Woo. International Search Report for PCT/US2010/039123. Date of Mailing: Feb. 24, 2011.
Patteux, Claudine. International Search Report for PCT/US2010/043373. Date of Mailing: Oct. 10, 2010.
Pawsey et al., "Hyperpolarized 129Xe Nuclear Magnetic Resonance Studies of Isoreticular Metal-Organic Frameworks," Phys. Chem. 111:6060-6067 (2007).
Phan et al., "Synthesis, Structure, and Carbon Dioxide Capture Properties of Zeolitic Imidazolate Frameworks," Acc. Chem. Res 43:58-67 (2009).

Phan et al., "Metal-Organic Frameworks of Vanadium as Catalysts for Conversion of Methane to Acetic Acid," Inorg. Chem. 50:7388-7390 (2011).
Plevert et al., "A Flexible Germanate Structure Containing 24-Ring Channels With Very Low Framework Density," J. Am. Chem. Soc. 123:12706-12707 (2001).
Plevert et al., "Synthesis and Characterization of Zirconogermanates," Inorg. Chem., 42:5954-5959 (2003).
Plevert et al., "Layered Structures Constructed from New Linkages of Ge7(O,OH,F)19 Clusters," Chem. Mater. 15:714-718 (2003).
Reineke et al., "From Condensed Lanthanide Coordination Solids to Microporous Frameworks Having Accessible Metal Sites," J. Am. Chem. Soc 121:1651-1657 (1999).
Reineke et al., "A Microporosity of Lanthanide-Organic Frameworks," Angew. Chem. Int. Ed. 38:2590-2594 (1999).
Reineke et al., "Large Free Volume in Interpenetrating Networks: The Role of Secondary Building Units Exemplified by Tb2(ADB)3[(CH3)2SO]4-16[(CH3)2SO]," J. Am. Chem. Soc. 122:4843-4844 (2000); Featured in Science Magazine, Editors Choice (Nov. 2000).
Rosi et al., "Infinite Secondary Building Units and Forbidden Catenation in Metal-Organic Frameworks," Angew. Chem. Int. Ed. 41:294-297 (2002).
Rosi et al., "Advances in the Chemistry of Metal-Organic Frameworks," CrystEngComm 4:401-404 (2002).
Rosi et al., "Hydrogen Storage in Microporous Metal-Organic Frameworks," Science 300:1127-1129 (2003); Featured in (1) Chemical & Engineering News magazine, May 19, 2004, and (2) Technology Research News Magazine, May 21, 2003.
Rosi et al., "Rod-Packings and Metal-Organic Frameworks Constructed from Rod-Shaped Secondary Building Units," J. Am. Chem. Soc. 127:1504-1518 (2005).
Rowsell et al., "Hydrogen Sorption in Functionalized Metal-Organic Frameworks," J. Am. Chem. Soc.126:5666-5667 (2004).
Rowsell et al., "Metal-Organic Frameworks: A New Class of Porous Materials," Microporous Mesoporous Mater. 73:3-14 (2004).
Rowsell et al., "Strategies for Hydrogen Storage in Metal-Organic Frameworks," Angew. Chem. Int. Ed. 44:4670-4679 (2005).
Rowsell et al., "Gas Adsorption Sites in a Large-Pore Metal-Organic Framework," Science 309:1350-1354 (2005).
Rowsell et al., "Characterization of H2 Binding sites in prototypical metal-organic frameworks by inelastic neutron scattering," J. Am. Chem. Soc. 127:14904-14910 (2005).
Rowsell et al., "Effects of Functionalization, Catenation, and Variation of the Metal Oxide and Organic Linking Units on the Low-Pressure Hydrogen Adsorption Properties of Metal-Organic Frameworks," J. Am. Chem. Soc. 128:1304-1315 (2006).
Siberio-Perez, "Raman Spectroscopic Investigation of CH4 and N2 Adsorption in Metal-Organic Frameworks," Chem. Mater. 19:3681-3685 (2007).
Smaldone et al., "Metal-Organic Frameworks from Edible Nature Products," Angew. Chem. Int. Ed. 49:8630-8634 (2010).
Spencer et al., "Determination of the Hydrogen Absorption Sites in Zn4O(1,4-benzenedicarboxylate) by Single Crystal Neutron Diffraction," Chem. Commun. 3:278-280 (2006); Epub Dec. 6, 2005.
Stallmach et al., "NMR Studies on the Diffusion of Hydrocarbons on the Metal-Organic Framework Material MOF-5," Angew. Chem. Int. Ed. 45:2123-2126 (2006).
Sudik et al., "Design, Synthesis, Structure, and Gas (N2, Ar, CO2, CH4 and H2) Sorption Properties of Porous Metal-Organic Tetrahedral and Heterocuboidal Polyhedra," J. Am. Chem. Soc. 127:7110-7118 (2005).
Sudik et al., "Metal-Organic Frameworks Based on Trigonal Prismatic Building Blocks and the New "acs" Topology," Inorg. Chem. 44:2998-3000 (2005).
Sudik et al., "A Metal-Organic Framework with a Hierarchical System of Pores and Tetrahedral Bbuilding Blocks," Angew. Chem. Int. Ed. 45:2528-2533 (2006).
Tranchemontagne et al. "Metal-Organic Frameworks with High Capacity and Selectivity for Harmful Gases," Proc. Natl. Acad. Sci. USA 105:11623-11627 (2008).
Tranchemontagne et al., "Reticular Chemistry of Metal-Organic Polyhedra," Angew. Chem. Int. Ed., 2008, 47:5136-5147 (2008).

(56) References Cited

OTHER PUBLICATIONS

Tranchemontagne et al., "Room Temperature Synthesis of Metal-organic Frameworks: MOF-5, MOF-74, MOF-177, MOF-199, and IRMOF-0," Tetrahedron 64:8553-8557 (2008).
Tranchemontagne et al. "Secondary Building Units, Nets and Bonding in the Chemistry of Metal-Organic Frameworks," Chem. Soc. Rev. 38:1257-1283 (2009).
Vairaprakash et al., "Synthesis of Metal-Organic Complex Arrays," J. Am. Chem. Soc. 133:759-761 (2011).
Valente et al., "Metal-organic Frameworks with Designed Chiral Recognition Sites," Chem. Commun. 46: 4911-4913 (2010).
Vodak et al., "Metal-Organic Frameworks Constructed from Pentagonal Antiprismatic and Cuboctahedral Secondary Building Units," Chem. Commun. 2534-2535 (2001).
Vodak et al., "Computation of Aromatic C3N4 Networks and Synthesis of the Molecular Precursor N(C3N3)3Cl6," Chem. Eur. J. 9:4197-4201 (2003).
Walton et al., "Understanding Inflections and Steps in Carbon Dioxide Adsorption Isotherms in Metal-Organic Frameworks," J. Am. Chem. Soc. 130:406-407 (2008).
Wang et al., "Colossal Cages in Zeolitic Imidazolate Frameworks as Selective Carbon Dioxide Reservoirs," Nature 453:207-211 (2008).
Yaghi et al., "Selective binding and removal of guests in a microporous metal-organic framework," Nature, Dec. 1995, pp. 703-706, vol. 378.
Yaghi et al., "Conversion of Hydrogen-Bonded manganese(II) and zinc(II) squarate (C4O42-) molecules, Chains, and Sheets to 3-D Cage Networks," J. Chem. Soc., Dalton Trans., 1995, 727-732.
Yaghi et al., "Presence of Mutually Interpenetrating Sheets and Channels in the Extended Structure of Cu(4,4'- Bipyridine)Cl," Angew. Chem. Int. Ed. Engl., 1995, 34, 207-209.
Yaghi et al., "The Utility of Polymeric Matrices in the Preparation of Single Crystals of Coordination Solids: Synthesis and Structure of CuII(1,4-C4H4N2)(C4O4)(OH2)4," J. Solid State Chem., 1995, 117, 256-260.
Goebel, Matthias, Supplemental European Search Report and Written Opinion for EP08826913. Date of Completion of Search and Written Opinion: Nov. 10, 2010.
Goebel, Matthias, Supplemental European Search Report and Written Opinion for EP08754337. Date of Completion of Search and Written Opinion: Dec. 3, 2010.
Grzesiak et al., "Polymer-Induced Heteronucleation for the Discovery of New Extended Solids," Angew. Chem. Int. Ed. 45:2553-2556 (2006).
Halper et al., "Topological Control in Heterometallic Metal-Organic Frameworks by Anion Templating and Metalloligand Design," J. Am. Chem. Soc. 128:15255-15268 (2006).
Hayashi et al., "Zeolite A Imidazolate Frameworks," Nature Materials 6:501-506 (2007).
Hexiang et al., "Multiple Functional Groups of Varying Rations in Metal-Organic Frameworks," Science 327 (5967):846-850 (2010).
Holler et al., "The first dinitrile frameworks of the rare earth elements: [LnCl3(1,4-Ph(CN)2] and [Ln2Cl6(1,4Ph(CN)2], Ln=Sm, Gd, Tb, Y; Access to novel metal-organic frameworks by solvent free synthesis in molten 1,4-benodinitrile," Inorganic Chemistry 47(21): 10141-9 (2008).
Honda, Masashi, International Preliminary Report on Patentability for PCT/US2008/051859. Date of Issuance of the Report: Jul. 28, 2009.
Howe, Patrick. International Search Report and Written Opinion for PCT/US2009/068849. Date of Mailing of the Search Report: 06/04/201.
Howe, Patrick. International Search Report and Written Opinion for PCT/US2010/022777. Date of Mailing: Jun. 7, 2010.
Huang et al., "Thermal Conductivity of Metal-Organic Framework 5 (MOF-5): Part II. Measurement," Int. J. Heat Mass Transfer 50:405-411 (2007).
Isaeva et al., "Metal-organic frameworks—new materials for hydrogen storage," Russian Journal of General Chemistry 77(4):721-739 (2007).
Jeong et al., "Asymmetric Catalytic Reactions by NbO-Type Chiral Metal-Organic Frameworks," Chem. Sci. 2:877-882 (2011).
Kaye et al., "Impact of Preparation and Handling on the Hydrogen Storage Properties of Zn4O(1,4-benzenedicarboxylate)3 (MOF-5)," J. Am. Chem. Soc. 129:14176-14177 (2007).
Kim et al., "Assembly of Metal-Organic Frameworks From Large Organic and Inorganic Secondary Building Units: New Examples and Simplifying Principles for Complex Structures," J. Am. Chem. Soc. 123:8239-8247 (2001).
Kim, Su Mi, International Search Report and Written Opinion for PCT/US2009/068731. Date of Mailing: Aug. 19, 2010.
Kim, Su Mi. International Search Report for PCT/US2010/039154. Date of Mailing: Feb. 23, 2011.
Klaes, Daphne. International Search Report and Written Opinion for PCT/US2010/021201. Date of Mailing: Apr. 27, 2010.
Kyoungmoo et al., "A Crystalline Mesoporous Coordination Copolymer with High Microporosity," Angew. Chem. Int. Ed. 47(4):677-680 (2008).
Lee, Ji Min. International Search Report for PCT/US2010/039284. Date of Mailing: Feb. 22, 2011.
Li et al., "Coordinatively Unsaturated Metal Centers in the Extended Porous Framewokr of Zn3(BDC)3-6CH3OH (BDC=1,4-Benzenedicarboxylate)," J. Am. Chem. Soc. 2186-2187 (1998).
Li et al., "Establishing Microporosity in Open Metal-Organic Frameworks: Gas Sorption Isotherms for Zn(BDC) (BDC=1,4-Benzenedicaroxylate)," J. Am. Chem. Soc. 120:8571-8572 (1998).
Li et al., "Porous Germanates: Synthesis, Structure and Inclusion Properties of Ge7O14.5F2-[(CH3)2NH2]3(H2O)O.86," J. Am. Chem. Soc. 120:8567-8568 (1998).
Li et al., "Transformation of Germanium Dioxide to 4-Connected Porous Germanate Net," J. Am. Chem. Soc. 10569-10570 (1998).
Li et al., "An Open-Framework Germanate with Polycubane-Like Topology," Angew. Chem. INt. Ed., 38:653-655 (1999).
Li et al., "Supertetrahedral Sulfide Crystals with Giant Cavities and Channels," Science 283:1145-1147 (1999).
Li et al., "Non-interpenetrating Indium Sulfide with a Supertetrahedral Cristobalite Famework," J. Am. Chem. Soc. 121:6096-6097 (1999).
Li et al., "Design and Synthesis of an Exceptionally Stable and Highly Porous Metal-Organic Framework," Science 402:276-279 (1999); Featured in (1) Chemical and Engineering News (Nov. 22, 19999) and (2) Science News (Nov. 20, 1999).
Li et al., "Ge2ZrO6F2 (H2DAB)H2O: A 4-Connected Microporous Material with "Bow Tie" Building Units and an Exceptional Proportion of 3-Rings," J. Am. Chem. Soc. 122:12409-12410 (2000).
Li et al., "20 A [Cd4In16S35]14-Supertetrahedral T4 Clusters as Building Units in Decorated Cristobalite Frameworks," J. Am. Chem Soc. 123:4867-4868 (2001).
Li et al., "[Cd16In64S134]44-: 31-Å Tetrahedron with a Large Cavity," Angew. Chem. Int. Ed 42:1819-1821 (2003).
Li et al., "A metal-organic framework replete with ordered donor-acceptor catenanes," Chem. Commun. 46:380-382 (2010).
Li et al., "A Catenated Strut in a Catenated Metal-Organic Framework," Angew. Chem. Int. Ed. 49:6751-6755 (2010).
Linder, Nora. International Preliminary Report on Patentability for PCT/US2010/022777. Date of Mailing: Aug. 11, 2011.
Llabres et al., "MOFs as catalysts: Activity, reusability and shape-selectivity of a Pd-containing MOF," JOurnal of Catalysis 250(2):294-298.
Long et al., "The Pervasive Chemistry of Metal-Organic Frameworks," Chem. Soc. Rev. 38:1213-1214 (2009).
Lu et al., "Synthesis and Structure of Chemically Stable Metal-Organic Polyhedra," J. Am. Chem. Soc. 131:(35) 12532-12533 (2009).
Michalitsch, Richard. International Search Report and Written Opinion for PCT/US2009/069700. Date of Mailing: May 7, 2010.
Millward et al., "Metal-Organic Frameworks with Exceptionally High Capacity for Storage of Carbon Dioxide at Room Temperature," J. Am. Chem. Soc. 127:17998-17999 (2005).
Morris et al., "Crystals as Molecules: Postsynthesis Covalent Functionalization of Zeolitic Imidazolate Frameworks," J. Am. Chem. Soc. 130:12626-12627 (2008).

(56) References Cited

OTHER PUBLICATIONS

Morris et al., "A Combined Experimental-Computational Investigation of Carbon Dioxide Capture in a Series of Isoreticular Zeolitic Imidazolate Frameworks," J. Am. Chem. Soc. 132:11006-11008 (2010).
Morris et al., "Postsynthetic Modification of a Metal-Organic Framework for Stabilization of a Hemiaminal and Ammonia Uptake," Inorg. Chem. 50:6853-6855 (2011).
Moyse, Ellen, International Preliminary Report on Patentability and Written Opinion, Date of Issuance of Report: Nov. 17, 2009, International Application No: PCT/US08/006008.
Mulhausen, Dorothee. International Preliminary Report on Patentability for PCT/US2009/069700. Date of Mailing: Jul. 7, 2011.
Mulhausen, Dorothee. International Preliminary Report on Patentability for PCT/US2010/021201. Date of Mailing Jul. 28, 2011.
Ni et al,. "Porous Metal-Organic Truncated Octahedron Constructed from Paddle-Wheel Squares and Terthiophene Links," J. Am. Chem. Soc. 127:12752-12753 (2005).
Nickitas-Etienne, Athina, International Preliminary Report on Patentability and Written Opinion, Date of Issuance of Report: Jan. 19, 2010, International Application No: PCT/US08/70149.
Nickitas-Etienne, Athina. International Preliminary Report on Patentability for PCT/US2008/07741. Date of issuance of this report: Mar. 30, 2010.
Nickitas-Etienne, Athina, International Preliminary Report on Patentability for PCT/US2009/068731. Date of Issuance of the Report: Jun. 21, 2011.
Nickitas-Etienne, Athina. International Preliminary Report on Patentability for PCT/US2009/068849. Date of Mailing: Jun. 30, 2011.
Ashton, Peter R. et al., "Hydrogen-Bonded Complexes of Aromatic Crown Ethers with (9-Anthracenyl) methylammonium Derivatives", J. Am. Chem. Soc., 1997, 119 (44), pp. 10641-10651.
Carlucci, Lucia et al., "Polycatenation, polythreading and polyknotting in coordination network chemistry", Coordination Chemistry Reviews 246, 2003, pp. 247-289.
Han, SS et al., "Improved designs of metal-organic frameworks for hydrogen storage", Angew. Chem Int. Ed., 2007, 46, pp. 6289-6292.
Kim, Su Mi, International Search Report and Written Opinion, Date of mailing of report: Feb. 24, 2010, International Application No: PCT/US09/046463.
Loeb, SJ, "Rotaxanes as ligands: form molecules to materials", Chemical Society Reviews, 2007, 36, pp. 226-235.
Wong-Foy, AG et al., "Exceptional H2 saturation uptake in microporous metal-organic frameworks", J. Am. Chem. Soc., 2006, 128, pp. 3794-3495.
Andrew et al., "Post-Synthetic Modification of Tagged MOFs," Angew. Chem. Int. Ed. 47:8482-8486 (2008).
Baharlou, Simin. International Preliminary Report on Patentability for PCT/US2009/046463. Date of Mailing: Dec. 16, 2010.
Banerjee et al., "High-Throughput Synthesis of Zeolitic Imidazolate Frameworks and Application to CO2 Capture," Science 319:939-943 (2008).
Banerjee et al., "Control of Pore Size and Functionality in Isoreticular Zeolitic Imidazolate Frameworks and their Carbon Dioxide Selective Capture Properties," J. Am. Chem. Soc. 131:3875-3877 (2009).
Barman et al., "Azulene Based Metal-Organic Frameworks for Strong Adsorption of H2," Chem. Commun. 46:7981-7983 (2010).
Barton et al., "Tailored Porous Materials," Chem. Mater. 11:2633-2656 (1999).
Bloch et al., "Metal Insertion in a Microporous Metal-Organic Framework Lined with 2,2'-Bipyridine" J. Am. Chem. Soc. 132:14382-14384 (2010).
Braun et al., "1,4-Benzenedicarboxylate Derivatives as Links in the Design of Paddle-Wheel Units and Metal-Organic Frameworks," Chem. Commun. 24:2532-2533 (2001).
Britt et al., "Highly efficient separation of carbon dioxide by a metal-organic framework replete with open metal sites," Proc. Natl. Acad. Sci. USA 106:20637-20640 (2009).

Carlucci et al., "Nanoporous three-dimensional networks topologically related to cooperite from the self-assembly of copper(I)centres and teh 1,2,4,5-tetracyanobenzene," New J. Chem. 23(23):397-401 (1999).
Carlucci, Lucia et al., "Polycatenation, polythreading and polyknotting in coordination network chemistry" Coordination Chemistry Reviews 246, 2003, pp. 247-289.
Caskey et al., "Dramatic Tuning of CO2 Uptake via Metal Substitution in a Coordination Polymer with Cylindrical Pores," JACS 130(33):10870-10871 (2008).
Caskey et al., "Selected Applications of Metal-Organic Frameworks in Sustainable Energy Technologies," Material Matters 4.4:111 (2009).
Centrone et al., "Raman Spectra of Hydrogen and Deuterium Adsorbed on a Metal-Organic Framework," Chem. Phys. Lett. 411:516-519 (2005).
Chae et al., "Tertiary Building Units: Synthesis, Structure, and Porosity of a Metal-Organic Dendrimer Framework (MOD-1)," J. Am. Chem. Soc. 123:11482-11483 (2001).
Chae et al., "Design of Frameworks with Mixed Triangular and Octahedral Building Blocks Exemplified by the Structure of [Zn4O(TCA)2] Having the Pyrite Topology," Angew. Chem. Int. Ed. 42:3907-3909 (2003).
Chae et al., "A Route to High Surface Area, Porosity and Inclusion of Large Molecules in Crystals," Nature 427, 523-527 (2004); Featured in (1) Chemical & Engineering News magazine, Feb. 9, 2004, (2) BBC World Service, Feb. 2004, (3) New Scientist, Feb. 2004.
Chen et al., "Cu2(ATC)6H2O: Design of Open Metal Sites in Porous Metal-Organic Crystals (ATC: 1,3,5,7-adamantane tetracarboxylate)," J. Am. Chem. Soc. 122:11559-11560 (2000).
Chen et al., "Interwoven Metal-Organic Framework on a Periodic Minimal Surface with Extra-Large Pores," Science 291:1021-1023 (2001); Featured in Chemical and Engineering News, Feb. 21, 2001.
Chen et al., "Transformation of a Metal-Organic Framework from the NbO to PtS Net," Inorg. Chem. 41:181-183 (2005).
Chen et al., "High H2 Adsorption in a Microporous Metal-Organic Framework with Open-Metal Sites," Angew. Chem. Int. Ed. 44:4745-4749 (2005).
Chen et al., "A Microporous Metal-Organic Framework for Gas-Chomatographic Separation of Alkanes," Angew. Chem. Int. Ed. 45:1390-1393 (2006).
Cho et al., "A metal-organic framework material that functions as an enantioselective catalyst for olefin epoxidation," Chem. Comm. 24:2563-2565 (2006).
Choi et al., "Heterogeneity within Order in Crystals of a Porous Metal Organic Framework," J. Am. Chem. Soc. 133:11920-11923 (2011).
Czaja et al., "Industrial applications of metal-organic frameworks," Chemical Society Reviews 38(5):1284-1293 (2009).
Delgado-Friedrichs et al., "Three-Periodic Nets and Tilings: Regular and Quasiregular Nets," Acta Cryst. A59:22-27 (2003).
Delgado-Friedrichs et al., "Three-Periodic Nets and Tilings: Semiregular Nets," Acta Cryst. A59:515-525 (2003).
Delgado-Friedrichs et al., "The CdSO4, Rutile, Cooperate and Quartz Dual Nets: Interpenetration and Catenation," Solid State Sciences 5:73-78 (2003).
Delgado-Friedrichs et al., "Reticular Chemistry: Occurrence and Taxonomy of Nets, and Grammar for the Design of Frameworks," Acc. Chem. Res. 38:176-182 (2005).
Delgado-Friedrichs et al. "What Do We Know About Three-Periodic Nets?," J. Solid State Chem. 178:2533-2554 (2005).
Delgado-Friedrichs et al. "Three-Periodic Nets and Tilings: Edge-Transitive Binodal Structures," Acta Cryst. 62:350-355 (2006).
Delgado-Friedrichs et al., "Taxonomy of Periodic Nets and the Design of Materials," Phys. Chem. 9:1035-1043 (2007).
Deng et al., "Multiple Functional Groups of Varying Ratios in Metal-Organic Frameworks," Science 327:846-850 (2010).
Deng et al., "Robust dynamics" Nature Chem. 2:439-443 (2010).
Doonan et al., "Isoreticular Metalation of Metal-Organic Frameworks," J. Am. Chem. Soc. 131:9492-9493 (2009).
Doonan, C., "Hydrogen Storage in Metal-Organic Frameworks," Annual Merit Review Proceedings of DOE Hydrogen Program, May 22, 2009.

(56) References Cited

OTHER PUBLICATIONS

Duren et al., "Design of New Materials for Methane Storage," Langmuir 20:2683-2689 (2004).

Eddaoudi et al., "Design and Synthesis of Metal-Organic Frameworks with Permanent Porosity," In Topics in Catalysis, G. A. Somorjai and J. M. Thomas, Eds., 9:105 (1999).

Eddaoudi et al., "Highly Porous and Stable Metal-Organic Framework: Structure Design and Sorption Properties," J. Am. Chem. Soc. 121:1391-1397 (2000).

Eddaoudi et al., "Porous Metal-Organic Polyhedra: 25 Å Cuboctahedron Constructed from Twelve Cu2(CO2)4 Paddle-Wheel Building Blocks," J. Am. Chem. Soc. 123:4368-4369 (2001).

Eddaoudi et al., "Modular Chemistry: Secondary Building Units as a Basis for the Design of Highly Porous and Robust Metal-Organic Carboxylate Frameworks" Acc. Chem. Res. 34:319-330 (2001).

Eddaoudi et al., "Geometric Requirements and Examples of Important Structures in the Assembly of Square Building Blocks," Proc. Natl. Acad. Sci. 99:4900-4904 (2002).

Eddaoudi et al., "Systematic Design of Pore Size and Functionality in Isoreticular Metal-Organic Frameworks and Application in Methane Storage," Science 295:469-472 (2002): Featured in (1) Chemical and Engineering News, Jan. 21, 2002, and (2) Chemical Insight magazine, Nov. 15, 2002.

Eddaoudi et al., "Cu2[o-Br-C6H3(CO2)2]2(H2O)2•(DMF)8(H2O)2: A Framework Deliberately Designed to have the NbO Structure Type," J. Am. Chem. Soc. 124:376-377 (2002).

Furukawa et al., "Crystal Structure, Dissolution, and Deposition of a 5 nm Functionalized Metal-Organic Great Rhombicuboctahedron," J. Am. Chem. Soc. 128:8398-8399 (2006).

Furkawa et al., "Independent verification of the saturation hydrogen uptake in MOF-177 and establishment of a benchmark for hydrogen adsorption in metal-organic frameworks," J. Mater. Chem. 17:3197-3204 (2007).

Furukawa et al., "Control of Vertex Geometry, Structure Dimensionality, Functionality, and Pore Metrics in the Reticular Synthesis of Crystalline Metal-Organic Frameworks and Polyhedra," J. Am. Chem. Soc. 130:11650-11661 (2008).

Furukawa et al., "Ultra-High Porosity in Metal-Organic Frameworks," Science 239:424-428 (2010).

Glover et al., "MOF-74 building unit has a direct impact on toxic gas adsorption," J. Chem. Eng. Sci. 66:163-170 (2011).

Gould et al., "The Amphidynamic Character of Crystalline MOF-5: Rotational Dynamics in a Free-Volume Environment," J. Am. Chem. Soc. 130:3246-3247 (2008).

Yaghi et al., "Open-Framework Solids with Diamond-Like Structures Prepared from Clusters and Metal-Organic Building Blocks," Mater. Res. Soc. Symp. Proc., 1995, 371, 15.

Yaghi et al., "Hydrothermal Synthesis of a Metal-Organic Framework Containing Large Rectangular Channels," J. Am. Chem. Soc., 1995, 117, 10401-10402.

Yaghi et al., "Construction of Microporous Materials from Molecular Building Blocks," Fundamental Materials Research, T. J. Pinnavaia and M. F. Thorpe, eds., vol. II, Plenum: New York, p. 111 (1995).

Yaghi et al., "Construction of Porous Solids from Hydrogen-Bonded Metal Complexes of 1,3,5-Benzenetricarboxylic Acid," J. Am. Chem. Soc., 1996, 118, 9096-9101.

Yaghi et al., "Conversion of Molecules and Clusters to Extended 3-D Cage and Channel Networks," Metal Containing Polymeric Materials, C. U. Pittman, C. E. Carraher, B. M. Culbertson, M. Zeldin, J. E. Sheets, Eds., Plenum: New York, p. 219 (1996).

Yaghi et al., "Selective Guest Binding by Tailored Channels in a 3-D Porous Zinc(II)-1,3,5-Benzenetricarboxylate Network," J. Am. Chem. Soc., 1997, 119, 2861-2868.

Yaghi et al., "Crystal Growth of Extended Solids by Nonaqueous Gel Diffusion," Chem. Mater., 1997, 9, 1074-1076.

Yaghi et al., "A Molecular Railroad with Large Pores: Synthesis and Structure of Ni(4,4'-bpy)2.5(H2O)2(ClO4)2•1.5(4,4'-bpy)2(H2O)," Inorg. Chem., 1997, 36, 4292-4293.

Yaghi et al., "Construction of a New Open-Framework Solid form 1,3,5-Cyclohexanetricarboxylate and Zinc(II) Building Blocks," J. Chem. Soc. Dalton Trans. 2383-2384 (1997).

Yaghi et al., "Designing Microporosity in Coordination Solids," Modular Chemistry, J. Michl, Ed., Kluwer: Boston, p. 663 (1997).

Yaghi et al., "Synthetic Strategies, Structure Patterns, and Emerging Properties in the Chemistry of Modular Porous Solids," Acc. Chem. Res. 31:474-484 (1998).

Yaghi et al., "Design of Solids from Molecular Building Blocks: Golden Opportunities for Solid State Chemistry," J. Solid State Chem. 152, 1-2 (2000).

Yaghi et al., "T-Shaped Molecular Building Units in the Porous Structure of Ag(4,4'-bpy) NO3," J. Am. Chem. Soc., 1996, 118, 295-296.

Yaghi et al., "Synthesis and Structure of a Metal-Organic Solid Having the Cadmium (II) Sulfate Net," Mater. Res. Soc. Symp. Proc. 453:127, (1997).

Yaghi et al., "Transformation of Germanium Dioxide to 4-Connected Porous Germanate Net," J. Am. Chem. Soc., 20:10569-10570 (1998).

Yaghi et al., "A Molecular World Full of Holes," Chem. Innov. p. 3 (2000).

Yaghi et al., "Reticular Synthesis and the Design of New Materials," Nature 423:705-714 (2003).

Yaghi, Omar., "Porous Crystals for Carbon Dioxide Storage," slide presentation at the Fifth Annual Conference on Carbon Capture & Sequestration, US Department of Energy on May 10, 2006 http://www.netl.doe.gov/publications/proceedings/06/carbon-seq/Tech%20Session%20193.pdf.

Yaghi, Omar, "Hydrogen Storage in Metal-Organic Frameworks," slide presentation to DOE Hydrogen Program 2007 Annual Merit Review, US Department of Energy, on May 15, 2007 at http://www.hydrogen.energy.gov/pdfs/review07/st_10_yaghi.pdf.

Yaghi et al., "Metal-Organic Frameworks: A Tale of Two Entanglements," Nature materials 6:92-93 (2007).

Yaghi et al., "Reticular Chemistry and Metal-Organic Frameworks for Clean Energy," MRS Bulletin 34:682-690 (2009).

Young, Lee W., International Search Report and Written Opinion, Date of Mailing of Report: May 7, 2008, International Application No. PCT/US08/51859.

Young, Lee W., International search Report and Written Opinion, PCT/US08/06008, United States Patent & Trademark Office, Aug. 20, 2008.

Young, Lee W., International Search Report and Written Opinion, Date of Mailing: Dec. 2, 2008, International Application No. PCT/US08/77741.

Young, Lee W., International Search Report and Written Opinion, Date of Mailing: Jan. 12, 2009, International Application No. PCT/US08/70149.

Young, Jung Doo. International Search Report for PCT/US2010/050170. Date of Mailing: Jun. 8, 2011.

Zhang et al., "Docking in Metal-Organic Frameworks," Science 325:855-859 (2009).

Zhao et al., "Rigid-Strut-Containing Crown Ethers and [2]Catenanes for Incorporation into Metal-Organic Frameworks," Chem. Eur. J. 15:13356-13380 (2009).

Zhofu et al., "A Nearly Planar Water Sheet Sandwiched between Strontium-Imidazolium Carboxylate Coordination Polymers," Inorg. Chem. 44:5200-5202 (2005).

* cited by examiner

| Chemical Shift (ppm) | i | j | k |
|---|---|---|---|
| BORG-1 Pseudorotaxanes | 48.63 | N/A | 146.92 |
| PQT·2PF$_6$ | 48.73 | 124.22 | 147.06 |

| Chemical Shift (ppm) | a | b | c | d | e | f | g | h |
|---|---|---|---|---|---|---|---|---|
| BORG-1 Pseudorotaxanes | 174.79 | 131.83 | 127.19 | 88.32 | 95.78 | 115.20 | 153.35 | 70.31 |
| BORG-1 | 174.65 | 131.54 | 128.05 | 89.38 | 95.56 | 115.35 | 153.83 | 70.54 |

Figure 24 (cont'd)

CHEMICAL FRAMEWORK COMPOSITIONS AND METHODS OF USE

This application is a U.S. National Stage Application filed under 35 U.S.C. §371 and claims priority to International Application No. PCT/US09/46463, filed Jun. 5, 2009, which application claims priority under 35 U.S.C. §119 from Provisional Application Ser. No. 61/059,224, filed Jun. 5, 2008, the disclosures of which are incorporated herein by reference.

STATEMENT AS TO FEDERALLY SPONSORED RESEARCH

This invention was made with Government support of Grant No. W911NF-06-1-0405, awarded by the Department of the Army and Grant No. H94003-06-2-0607, awarded by the Department of Defense. The Government has certain rights in this invention.

TECHNICAL FIELD

The disclosure provides metal organic frameworks useful for sensing, gas sorption and separation, guest recognition, microelectronics and switches.

BACKGROUND

Molecular architecture is important for developing various materials both biologic and non-biologic. Biological systems use many 'architectural domains' to carry out specific tasks leading to complex functions. This concept is useful because such domains operate independently, yet they are connected.

SUMMARY

The disclosure provides a new class of organic frameworks based upon metal organic frameworks (MOFs). The new class goes beyond open reticulated geometries and are referred to herein as BORG frameworks, a new class of porous metal-organic materials. The BORG frameworks of the disclosure comprise one or more active domains that provide selective interactions with guest molecules useful for recognition and switching.

The disclosure provides a core structure comprising a MOF, wherein the struts linking monodentate or polydentate groups are modified with stereoelectronic selective groups. For example, in certain embodiments, MOFs comprising modified struts having molecule selective groups can be generated from electron donor links that recognize molecules that are electron acceptors. Furthermore, BORGs are frameworks in which active domains are placed in a regular three-dimensional array, and these domains are addressable to incoming substrates or stimuli (including chemical, electrochemical or photophysical).

The disclosure provides the design and synthesis of porous crystals composed of several architectural domains that are useful for the docking of molecules in a manner akin to the well-known molecular docking of drug molecules within protein targets.

The disclosure provides a metal organic framework comprising moieties with stereospecific and stereoelectronic control, pseudorotaxanes, rotaxanes, catenanes, chelates or cryptand structures. In one embodiment, the framework comprises a linking moiety connecting at least two monodentate of polydentate groups wherein the linking moiety is chemically bonded to a macrocycle or a functional group with stereospecific and stereoelectronic control. In yet another embodiment, the macrocycle is selected from the group consisting of: a crown ether; a cyclic macromolecule comprising C, O, N, S; and a macromolecular cyclic portion/functional group with stereospecific and stereoelectronic control of any of the foregoing. In another embodiment, a linking moiety connecting at least two monodentate or polydentate groups comprises a structure selected from the group consisting of structures I-XXX or any combination thereof. In yet another embodiment, the organic framework is a cantenane framework. In yet a further embodiment, the cantenane framework comprises linking moieties having a structure selected from the group consisting of structures XXXI-XXXIII.

The disclosure also provide an organic framework comprising a plurality of pores and a stereospecific and stereoelectronic selective group bonded to a linking moiety, wherein the stereospecific and stereoelectronic selective group comprises a macrocycle or functional group thereof extending into at least one of the plurality of pores. In one embodiment, the framework comprises a general structure M-L-M, wherein M comprises a monodentate or polydentate group and L comprise a linking moiety, wherein the linking moiety is bonded to a macrocycle or functional group. In yet a further embodiment, the macrocycle or functional group is selected from the group consisting of:

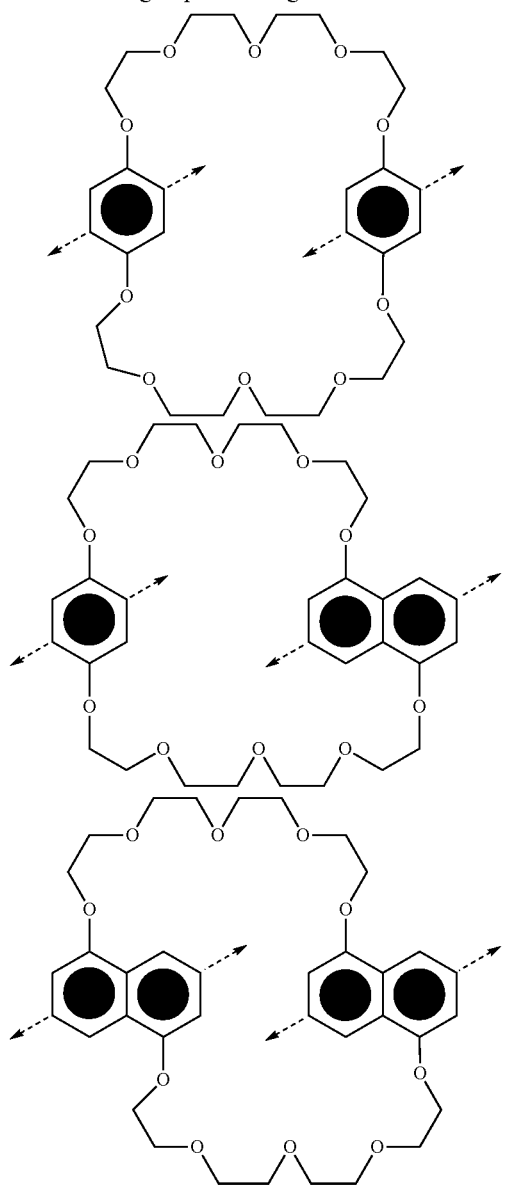

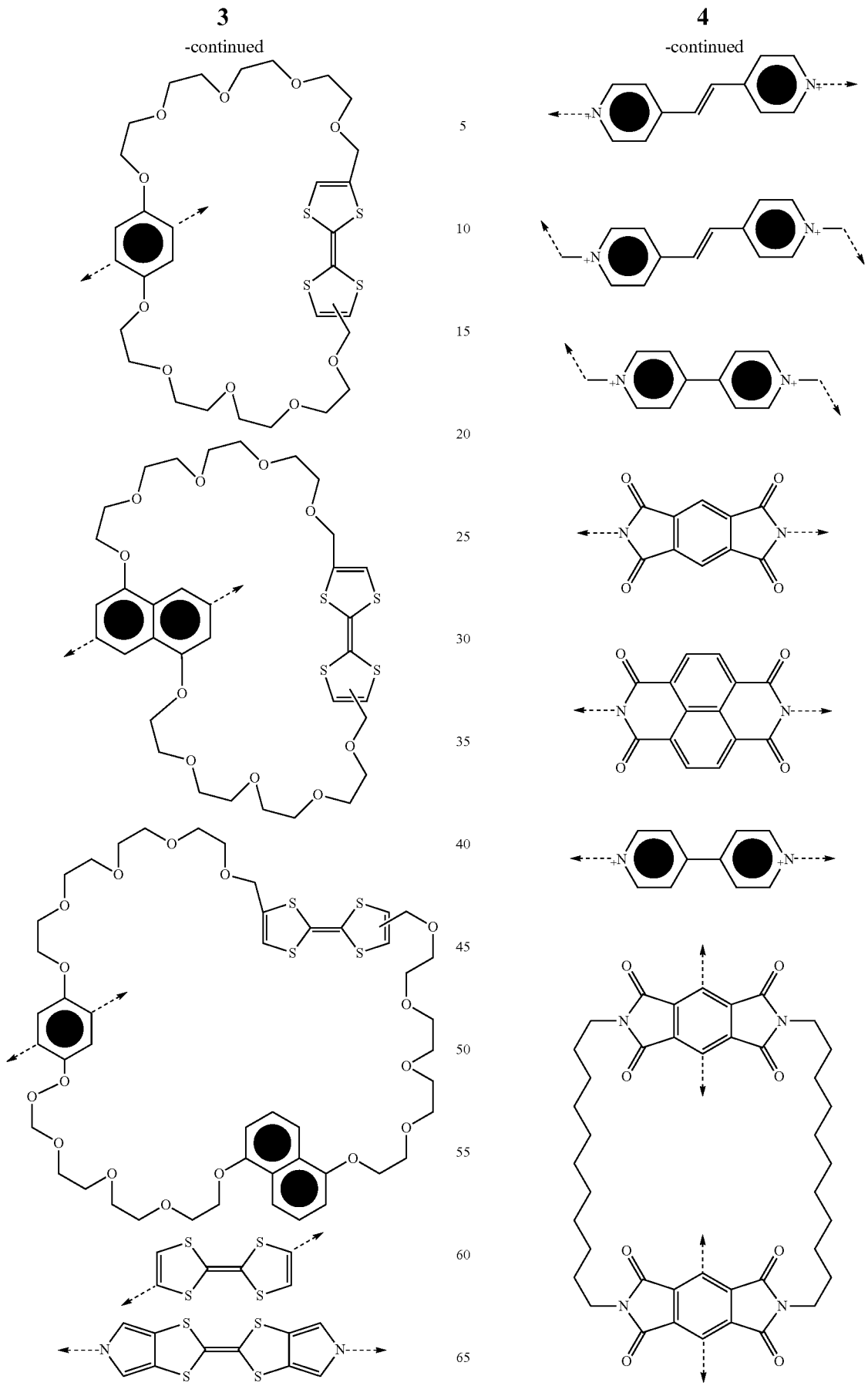

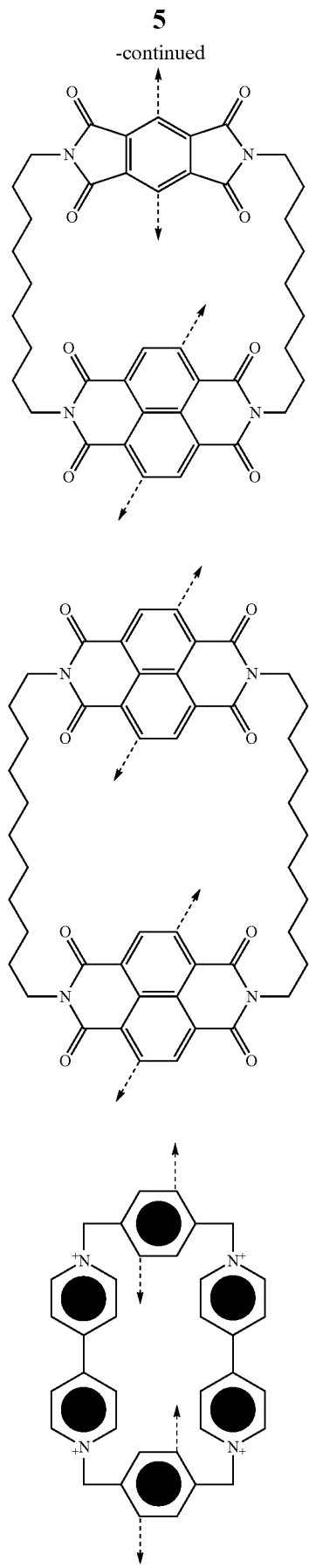
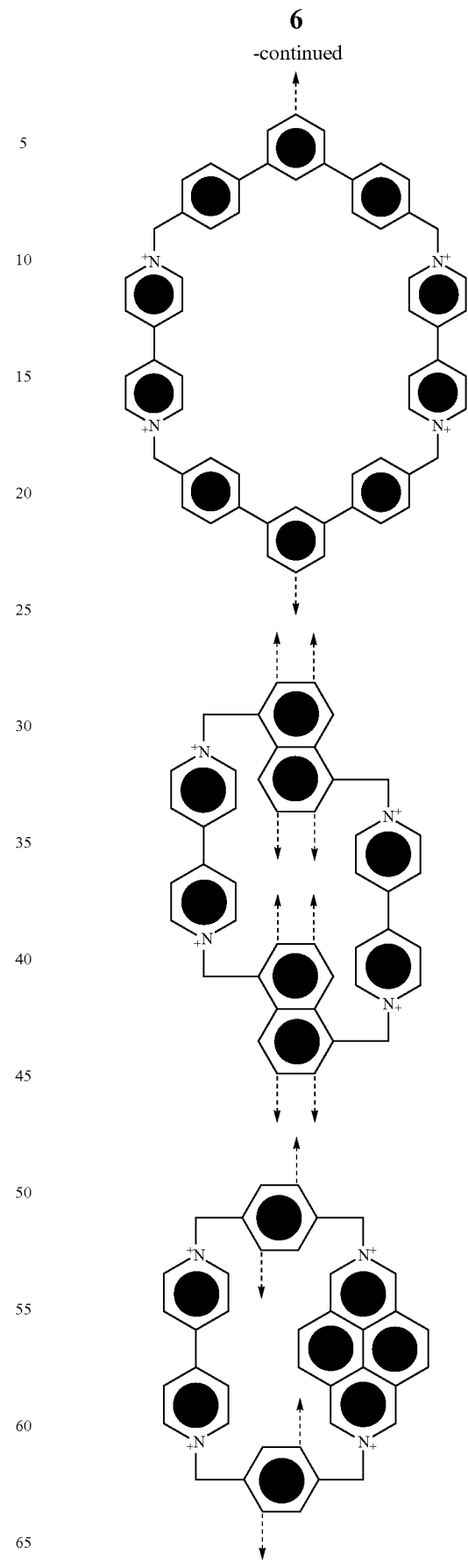

-continued

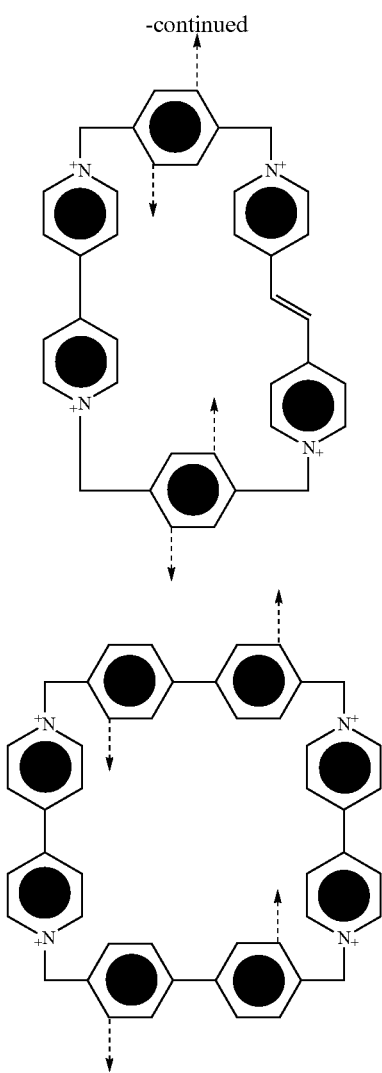

In one embodiment, the linking moiety comprises a structure selected from the group consisting of structure I-XXXII and XXXIII. The linking moieties can be homogenous or heterogenous. In another embodiment, the monodentate or polydentate group comprises a metal such as a transition metal or a metal selected from the group consisting of $Li^+$, $Na^+$, $Rb^+$, $Mg^{2+}$, $Ca^{2+}$, $Sr^{2+}$, $Ba^{2+}$, $Sc^{3+}$, $Ti^{4+}$, $Zr^{4+}$, $Ta^{3+}$, $Cr^{3+}$, $Mo^{3+}$, $W^{3+}$, $Mn^{3+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Ni^{2+}$, $Ni^+$, $Pd^{2+}$, $Pd^+$, $Pt^{2+}$, $Pt^+$, $Cu^{2+}$, $Cu^+$, $Au^+$, $Zn^{2+}$, $Al^{3+}$, $Ga^{3+}$, $In^{3+}$, $Si^{4+}$, $Si^{2+}$, $Ge^{4+}$, $Ge^{2+}$, $Sn^{4+}$, $Sn^{2+}$, $Bi^{5+}$, $Bi^{3+}$, and combinations thereof.

The disclosure also provides a microelectronic switch comprising a metal organic framework comprising a macrocycle or functional stereoselective and stereoelectronic portion thereof. In yet another embodiment, at least two monodentate or multidentate cores are linked to one another by a structure selected from the group consisting of structures I-XXXIII and any combination thereof.

The disclosure also provides sensors, gas separation devices, small molecule separation/purification devices, guest recognition devices an chiral separation medium comprising any of the organic frameworks and BORGs described herein.

In yet another embodiment, a framework of the disclosure comprises a crystal structure or refined structure as set forth in Tables 6-10.

The details of one or more embodiments of the invention are set forth in the accompanying drawings and the description below. Other features, objects, and advantages of the invention will be apparent from the description and drawings, and from the claims.

DETAILED DESCRIPTION

As used herein and in the appended claims, the singular forms "a," "and," and "the" include plural referents unless the context clearly dictates otherwise. Thus, for example, reference to "a species" includes a plurality of such species and reference to "the framework" includes reference to one or more frameworks and equivalents thereof, and so forth.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure.

Metal-organic frameworks (MOFs) are a class of crystalline porous materials whose structure is composed of metal-oxide units joined by organic linkers through strong covalent bonds. The flexibility with which these components can be varied has led to an extensive class of MOF structures with ultra-high surface areas, far exceeding those achieved for porous carbons. MOFs exhibit high thermal stability, with a decomposition between 350° C. and 400° C. in the case of MOF-5 (Eddaoudi M, et al., Science 295:469-472, 2002), ensuring their applicability across a wide temperature range. The unprecedented surface area and the control with which their pore metrics and functionality can be designed provides limitless potential for their structure to be tailored to carry out a specific application, thus suggesting the possibility of being superior to activated carbons in many applications.

Figure 1:
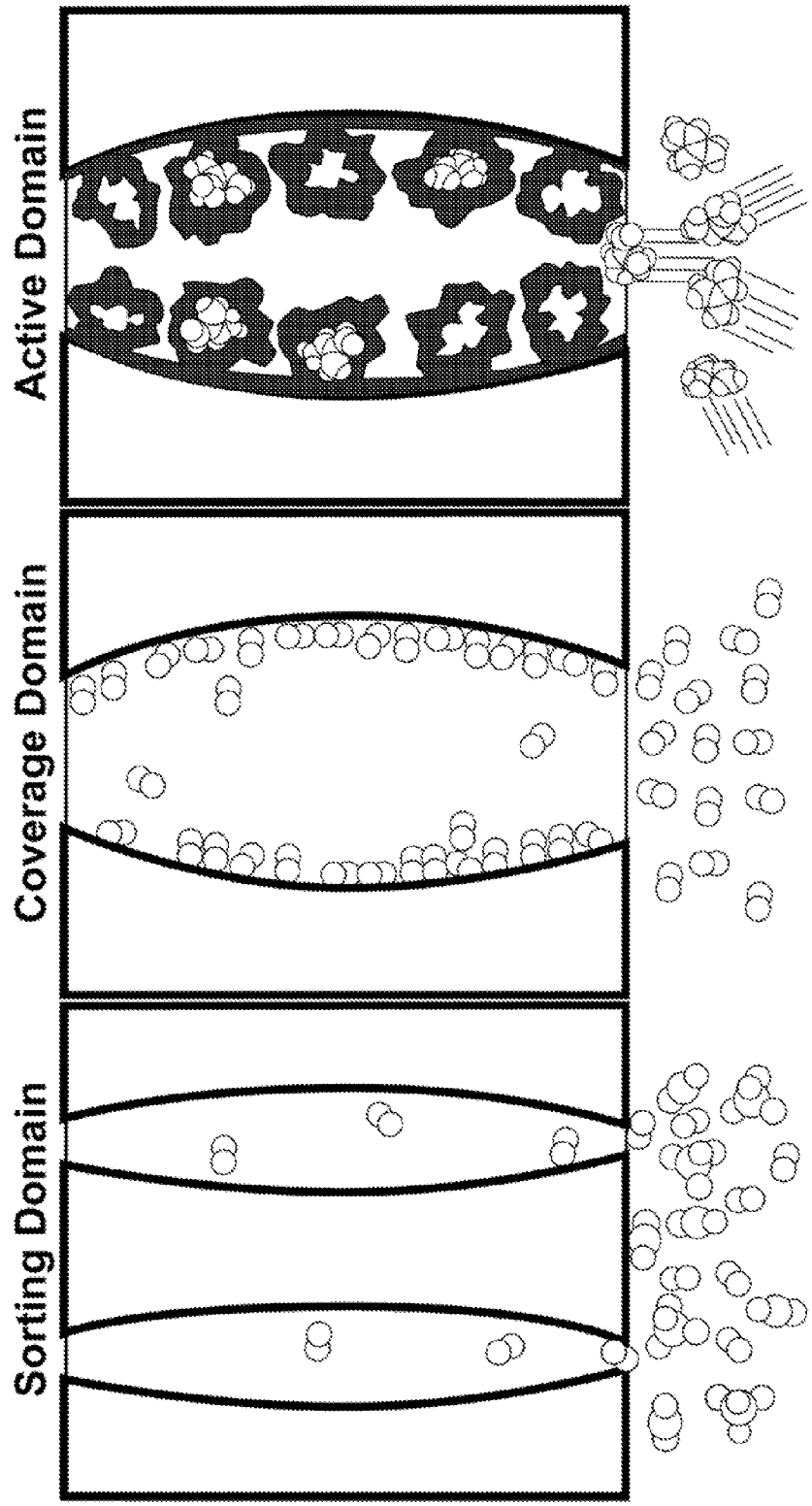
FIG. 1. Schematic illustration of sorting domain, coverage domain and active domain in porous frameworks.

The vast majority of porous MOFs prepared thus far can be regarded as having two important architectural domains: the pore aperture which is responsible for the shape- and size-selective binding of incoming molecules (sorting domain) and the internal surface of the pores onto which gases such as hydrogen and methane can be compacted and randomly distributed next to each other by virtue of their weak interactions with adsorption sites covering the struts and joints (coverage domain) (see, e.g., FIG. 1). The synthesis of more complex MOFs, however, where more than two domains are present, remains unexplored.

The disclosure shows the integration of stereoelectronic selective moieties in a modular fashion into struts of MOFs, thereby creating recognition sites into which incoming guests will dock in a highly specific manner with stereoelectronic control (active domain). The distinction between these three different domains (sorting, coverage, and selective) is depicted in FIG. 1. The disclosure thus provides frameworks in which a third functional domain is added to organic frameworks that combines shape, size and electronic elements in the recognition of incoming guests, and brings order to otherwise highly disordered guests in conventional MOFs. Accordingly, the disclosure provides new MOFs that are beyond open reticulated geometries (BORGs).

The BORGs of the disclosure are based upon an underlying metal organic frameworks having the general structure M-L-M, wherein L is a linking moiety or "strut" and M is a monodentate or multidentate linking cluster (e.g., a transition metal) and wherein L is functionalized to comprise a stereoelectronic selective group having, in one embodiment, an electron donor or acceptor capacity. In another embodiment, the underlying MOF linking moiety or strut comprises a carboxylic acid functional group that can be used in bond formation with a macrocycle. The functional group is used to bond/conjugate a stereoelectronic selective group to impart selectivity in a pore of a framework.

Figure 4:
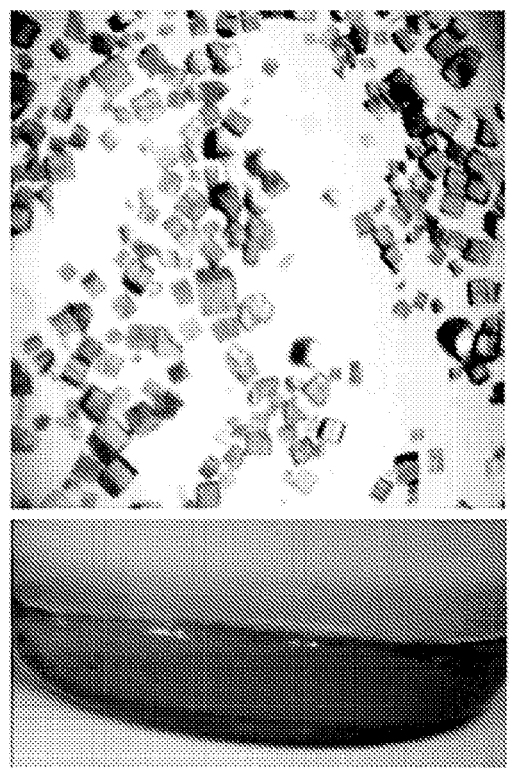
FIG. 4. X-ray diffraction and solid-state NMR spectroscopic studies on BORG-1, BORG-1 pseudorotaxanes, and their analogous molecular struts. Optical images of uncomplexed BORG-1 crystals (A) and complexed BORG-1 crystals (C) under the same optical view showed the single-crystal-to-single-crystal transformation. The resulting BORG-1 pseudorotaxanes remain the original high crystallinity, which was confirmed by X-ray diffraction (B). Structures of BORG-1 (D) and BORG-1 pseudorotaxanes (F) are illustrated in ball-and-stick models. Docking of $PQT^{2+}$ in BORG-1 resulted in the upfield shifts of $^{15}N$ CP/MAS signals (E). The same upfield shift trend was also found in the $^{15}N$ CP/MAS spectroscopic studies (H) on the $PQT^{2+}$ inclusion in strut 2 (G). The spectrum of free $PQT^{2+}$ had a $^{15}N$ signal centered at 207.0 ppm, while that of the $[PQT \subset 2].2PF_6$ (I) showed a mean shift of 202.1 ppm. Color schemes: $Zn_4O$ $(COO)_6$ polyhedra, gold; organic strut, gray; BPP34C10, red; $PQT^{2+}$, blue. All hydrogen atoms and counter ions have been omitted for clarity.
Figure 4:
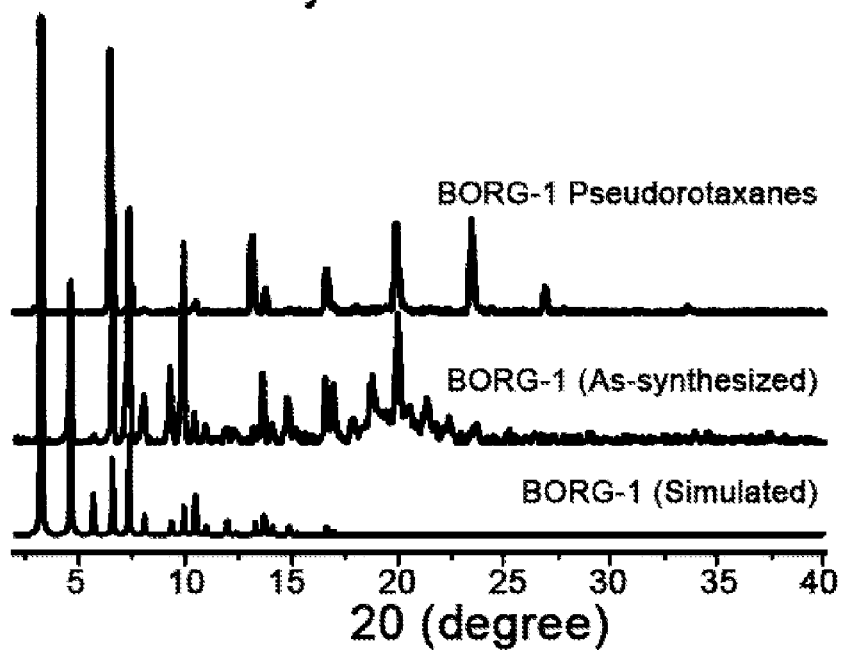
Figure 4:
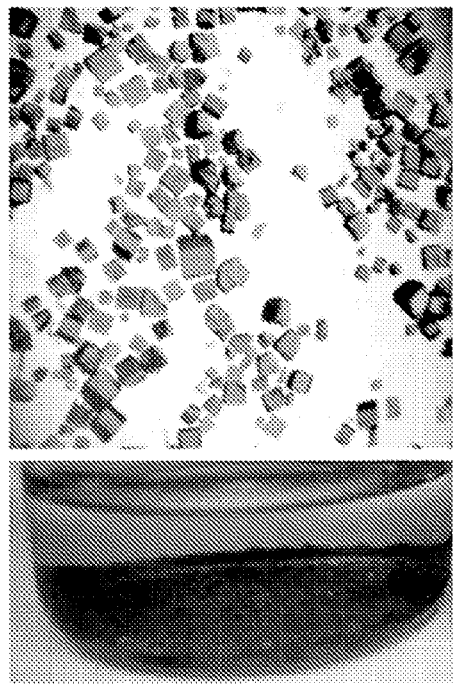
Figure 4:
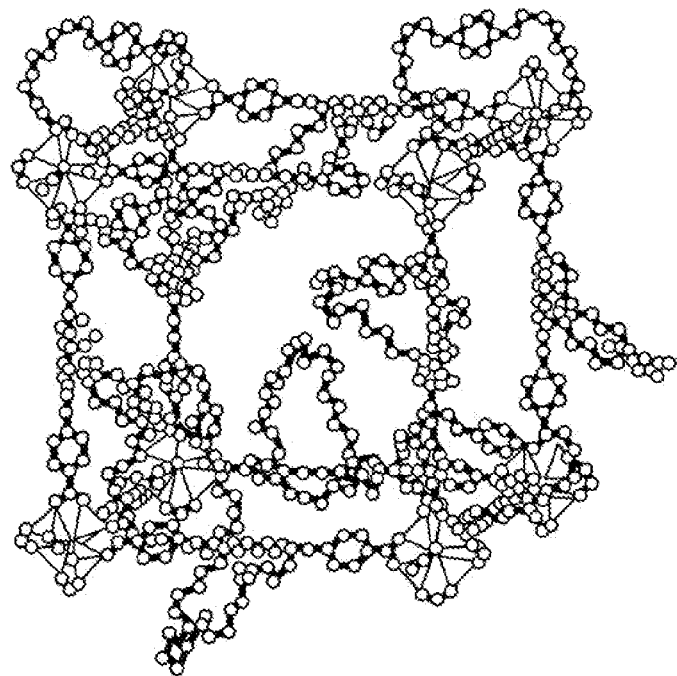
Figure 4:
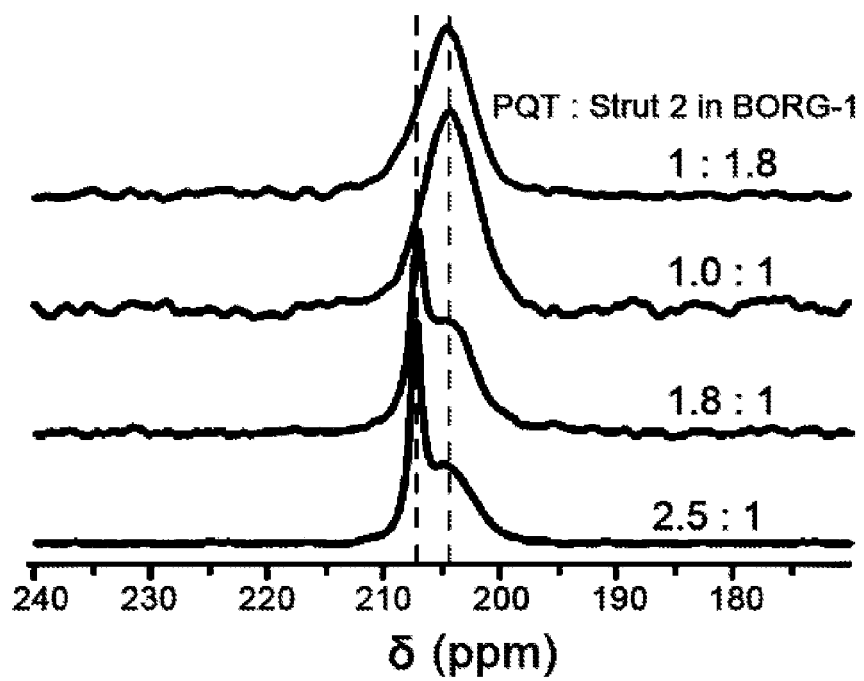
Figure 4:
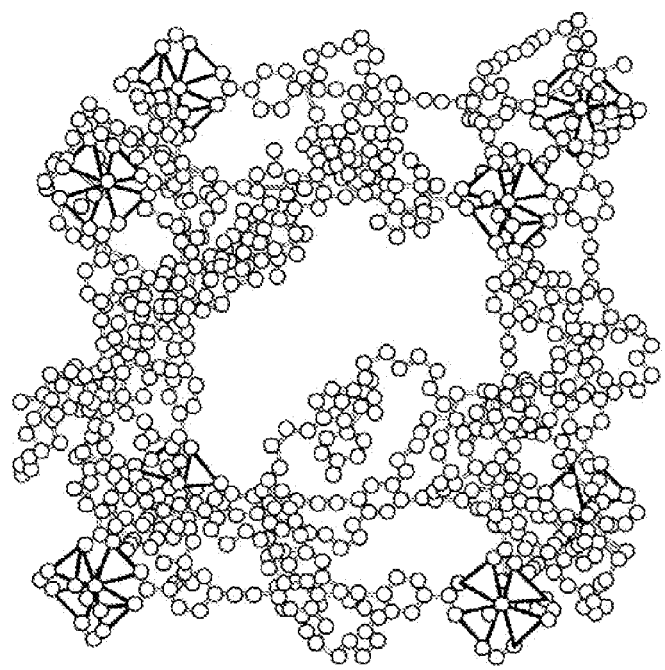
Figure 4:
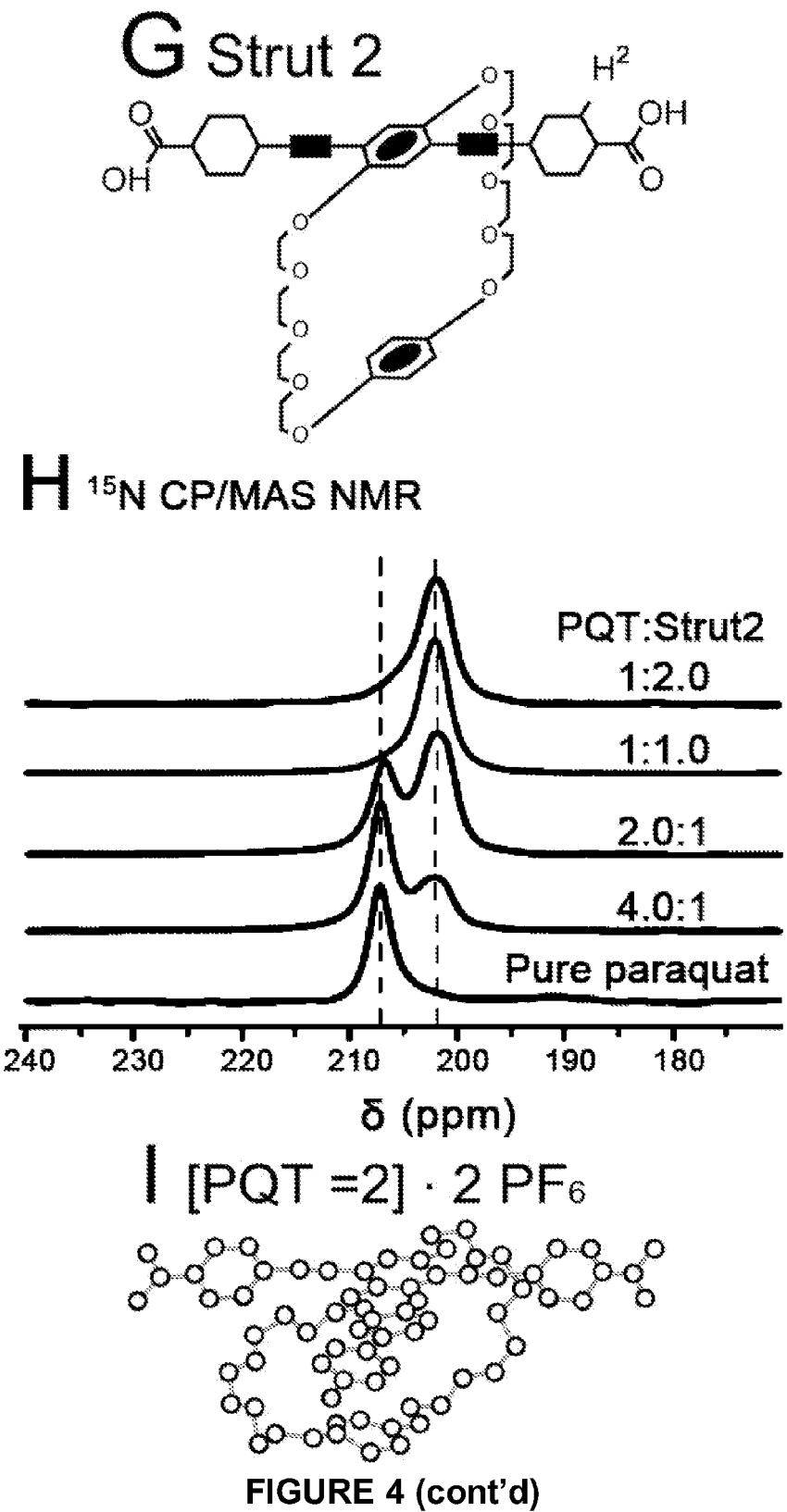

The BORGs presented here combine the precise positioning of the active domains with docking as an expression of molecular recognition. This property can be exemplified through the molecular recognition behavior of the macrocyclic polyethers (structures 2 and 3) as docking sites. For example, when BORG-1 crystals were introduced into a saturated solution of $PQT.2PF_6$ in $Me_2CO$, the crystals immediately turned red (FIG. 4, A and C)—a typical behavior for this binding event that indicates significant charge-transfer interactions between the $PQT^{2+}$ dications and crown ether rings. This observation points to the formation of BORG-1 pseudorotaxanes by threading of the $PQT^{2+}$ dication through the middle of the crown ether. The reversibility of such process was evidenced by the reappearance of the original light yellow color upon rinsing with $Me_2CO$. Furthermore, the complexed BORG-1 maintained the original high crystallinity of the parent framework, as confirmed by their coincident powder X-ray diffraction (PXRD) patterns (FIG. 4B). The BORG constructs represent a significant advance towards bringing order in three-dimensions to the otherwise random placement of active molecules either on surfaces or at interfaces.

As used herein, a "core" refers to a repeating unit or units found in a framework. Such a framework can comprise a homogenous repeating core or a heterogeneous repeating core structure. A core comprises a monodentate or multidentate group (e.g., a transition metal or cluster of transition metals) and a linking moiety. A plurality of cores linked together defines a framework.

The term "cluster" refers to identifiable associations of 2 or more atoms. Such associations are typically established by some type of bond—ionic, covalent, Van der Waals, and the like.

A "linking cluster" refers to one or more reactive species capable of condensation comprising an atom capable of forming a bond between a linking moiety and a metal group or between a linking moiety and another linking moiety or between a linking moiety and a molecule selective group. In some embodiments, the linking cluster may comprise one or more different reactive species capable of forming a link with, for example, a bridging oxygen atom. For example, a linking cluster can comprise $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $CH(RSH)_2$, $C(RSH)_3$, $CH(RNH_2)_2$, $C(RNH_2)_3$, $CH(ROH)_2$, $C(ROH)_3$, $CH(RCN)_2$, $C(RCN)_3$, $CH(SH)_2$, $C(SH)_3$, $CH(NH_2)_2$, $C(NH_2)_3$, $CH(OH)_2$, $C(OH)_3$, $CH(CN)_2$, and $C(CN)_3$, wherein R is an alkyl group having from 1 to 5 carbon atoms, or an aryl group comprising 1 to 2 phenyl rings.

Generally a linking moiety comprises a substructure covalently linked to an alkyl or cycloalkyl group, comprising 1 to 20 carbon atoms, an aryl group comprising 1 to 5 phenyl rings, or an alkyl or aryl amine comprising alkyl or cycloalkyl groups having from 1 to 20 carbon atoms or aryl groups comprising 1 to 5 phenyl rings, and in which a linking cluster (e.g., a multidentate function groups) can become covalently bound to the substructure. A cycloalkyl or aryl substructure may comprise 1 to 5 rings that comprise either of all carbon or a mixture of carbon with nitrogen, oxygen, sulfur, boron, phosphorus, silicon and/or aluminum atoms making up the ring. Typically the linking moiety will comprise a substructure having one or more carboxylic acid linking clusters covalently attached.

As used herein, a line in a chemical formula with an atom on one end and nothing on the other end means that the formula refers to a chemical fragment that is bonded to another entity on the end without an atom attached. Sometimes for emphasis, a wavy line will intersect the line.

Transition metals useful in the formation of a BORG comprise any one or more of the following: Sc, Ti, V, Cr, Mn, Fe, Co, Ni, Cu, Zn, Y, Zr, Nb, Mo, Tc, Ru, Rh, Pd, Ag, Cd, Lu, Hf, Ta, W, Re, Os, Ir, Pt, Au, Hg, Lr, Rf, Db, Sg, Bh, Hs, Mt, Ds, Rg, and Uub. In a specific embodiment, the transition metal is Zn or Co.

A BORG can comprise a MOF substructure wherein the framework comprises a plurality of metal clusters comprising a metal ion and a linking moiety having a general structure selected from the group consisting of:

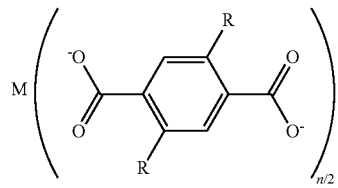

A

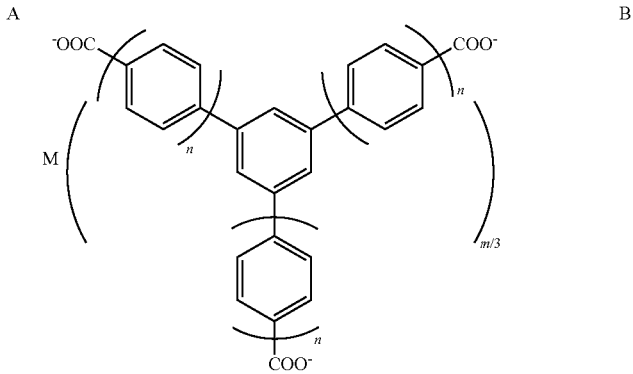

B

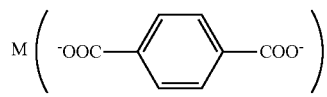

C

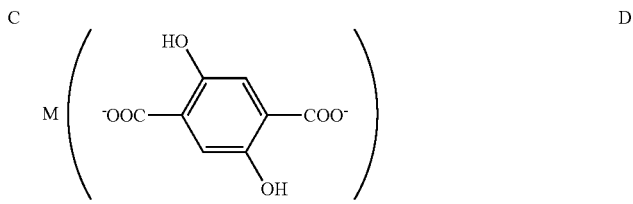

D

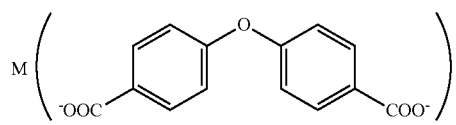

E

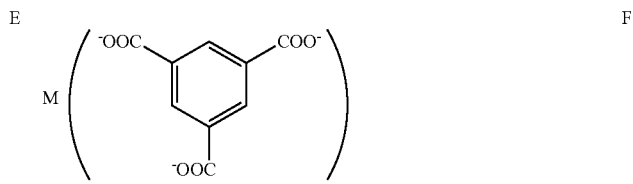

F

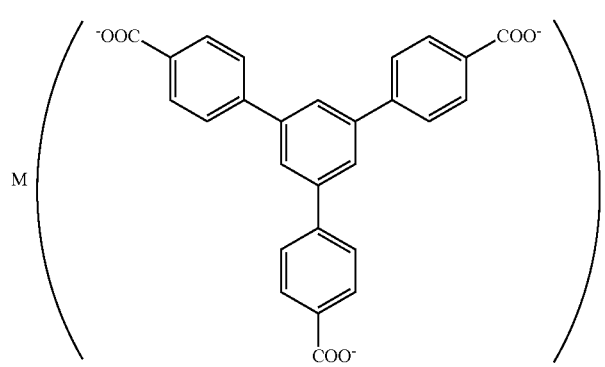

G

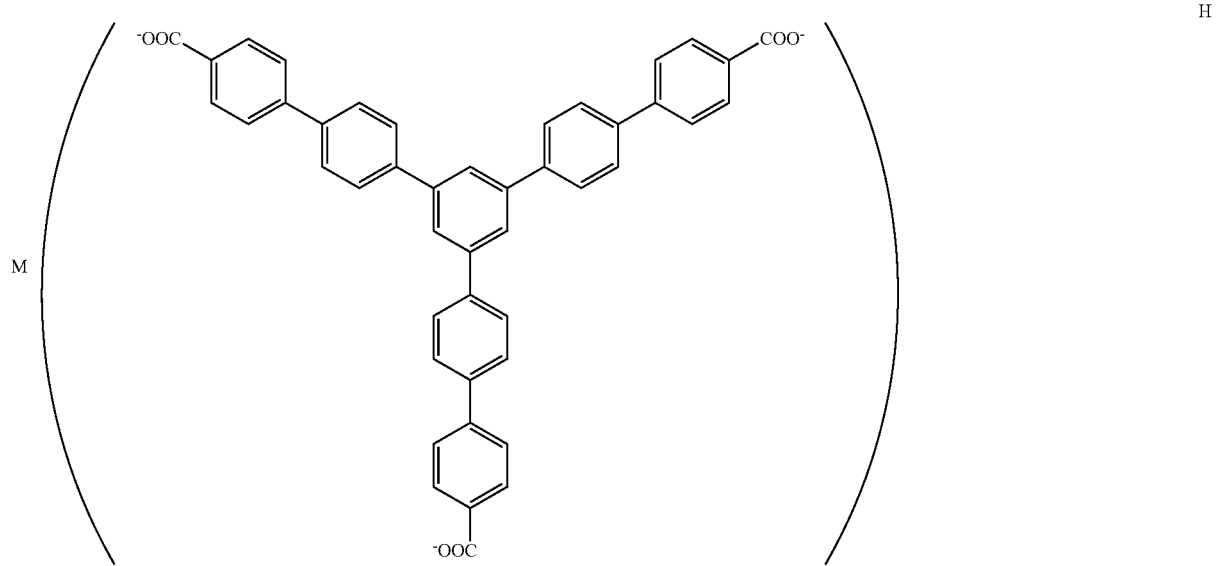

wherein M is a metal and wherein a benzene ring of the linking ligand is bonded to a macrocycle such as, for example, a crown ether.

It will be recognized that the linking moieties or struts of the disclosure can comprise any number of known linking moieties for existing MOFs. Furthermore, one of skill with recognize that that linking moieties may be generalized or derivatized so long as they comprise a functional group capable of bonding to a macrocycle or stereoelectonic selective group and a linking cluster that can bind to a monodentate or mutidentate cluster. For example, a linking moiety may comprise:

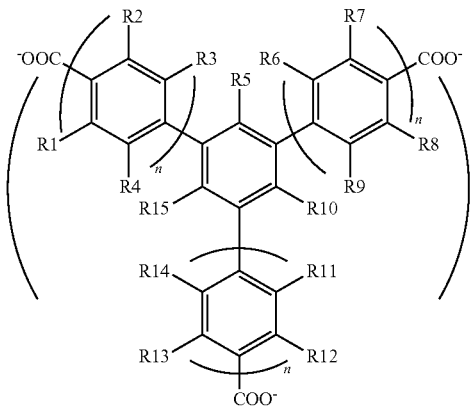

wherein each of R1-15 are independently selected from the group consisting of —H, —OH, —OR$^{16}$, aryl, substituted aryl, alkyl, substituted alkyl, carboxyl, aminocarbonyl, alkylsulfonylaminocarboxyl, alkoxycarbonyl, and halo, wherein R$^{16}$ can be —H, and aryl, substituted aryl, alkyl, substituted alkyl, carboxyl, aminocarbonyl, alkylsulfonylaminocarboxyl, alkoxycarbonyl, and halo.

The term "alkyl" refers to a saturated monovalent chain of carbon atoms, which may be optionally branched; the term "cycloalkyl" refers to a monovalent chain of carbon atoms, a portion of which forms a ring; the term "alkenyl" refers to an unsaturated monovalent chain of carbon atoms including at least one double bond, which may be optionally branched; the term "cycloalkenyl" refers to an unsaturated monovalent chain of carbon atoms, a portion of which forms a ring; the term "heterocyclyl" refers to a monovalent chain of carbon and heteroatoms, wherein the heteroatoms are selected from nitrogen, oxygen, and sulfur, a portion of which, including at least one heteroatom, form a ring; the term "aryl" refers to an aromatic mono or polycyclic ring of carbon atoms, such as phenyl, naphthyl, and the like; and the term "heteroaryl" refers to an aromatic mono or polycyclic ring of carbon atoms and at least one heteroatom selected from nitrogen, oxygen, and sulfur, such as pyridinyl, pyrimidinyl, indolyl, benzoxazolyl, and the like. It is to be understood that each of alkyl, cycloalkyl, alkenyl, cycloalkenyl, and heterocyclyl may be optionally substituted with independently selected groups such as alkyl, haloalkyl, hydroxyalkyl, aminoalkyl, carboxylic acid and derivatives thereof, including esters, amides, and nitriles, hydroxy, alkoxy, acyloxy, amino, alkyl and dialkylamino, acylamino, thio, and the like, and combinations thereof. It is further to be understood that each of aryl and heteroaryl may be optionally substituted with one or more independently selected substituents, such as halo, hydroxy, amino, alkyl or dialkylamino, alkoxy, alkylsulfonyl, cyano, nitro, and the like.

A framework (e.g., a BORG) of the disclosure can take any framework/structure. For example, using the methods of the disclosure, BORGs having any of the following framework codes can be obtained: ABW, ACO, AEI, AEL, AEN, AET, AFG, AFI, AFN, AFO, AFR, AFS, AFT, AFX, AFY, AHT, ANA, APC, APD, AST, ASV, ATN, ATO, ATS, ATT, ATV, AWO, AWW, BCT, BEA, BEC, BIK, BOG, BPH, BRE, CAN, CAS, CDO, CFI, CGF, CGS, CHA, CHI, CLO, CON, CZP, DAC, DDR, DFO, DFT, DOH, DON, EAB, EDI, EMT, EON, EPI, ERI, ESV, ETR, EUO, EZT, FAR, FAU, FER, FRA, GIS, GIU, GME, GON, GOO, HEU, IFR, IHW, ISV, ITE, ITH, ITW, IWR, IWV, IWW, JBW, KFI, LAU, LEV, LIO, LIT, LOS, LOV, LTA, LTL, LTN, MAR, MAZ, MEI, MEL, MEP, MER, MFI, MFS, MON, MOR, MOZ, MSE, MSO, MTF, MTN, MTT, MTW, MWW, NAB, NAT, NES, NON, NPO, NSI, OBW, OFF, OSI, OSO, OWE, PAR, PAU, PHI, PON, POZ, RHO, RON, RRO, RSN, RTE, RTH, RUT, RWR, RWY, SAO, SAS, SAT, SAV, SBE, SBS, SBT, SFE, SFF, SFG, SFH, SFN, SFO, SGT, SIV, SOD, SOS, SSY, STF, STI, STT, SZR, TER, THO, TON, TSC, TUN, UEI, UFI, UOZ, USI, UTL, VET, VFI, VNI, VSV, WEI, WEN, YUG, and ZON.

Various molecule selective groups (e.g., stereoelectronic groups) can be used to modify the strut or linking moiety of an underlying MOF structure to generate a BORG. In one embodiment, various macrocycles can be conjugated or bonded to the MOF strut to generate a BORG. Numerous macrocycles are known in the art. A macrocycle is, as defined by IUPAC, "a cyclic macromolecule or a macromolecular cyclic portion of a molecule." In the chemical literature, organic chemists may consider any molecule containing a ring of seven or more atoms to be a macrocyle. For example, modifications to the underlying strut in a MOF with a macrocycle can generate pseudorotaxanes, rotaxanes, catenane, chelates and cryptands structures. Such modified frameworks are useful in various compositions and systems including, but not limited to, gas separation and purification, sensors, and microelectronic switches.

A rotaxane is a mechanically-interlocked molecular architecture consisting of a "dumbbell shaped molecule" which is threaded through a "macrocycle". The two components of a rotaxane are kinetically trapped since the ends of the dumbbell (often called stoppers) are larger than the internal diameter of the ring and prevent disassociation (unthreading) of the components since this would require significant distortion of the covalent bonds. Examples of rotaxane have been found in biological systems including: cystine knot peptides, cyclotides or lasso-peptides such as microcin J25 are protein, and a variety of peptides with rotaxane substructure.

Other mechanically-interlocked molecular architectures, such as catenanes, can also be generated and are provided by the disclosure. A catenane is a mechanically-interlocked molecular architecture comprising two or more interlocked macrocycles. Typically the interlocked rings cannot be separated without breaking the covalent bonds of the macrocycles. As mentioned elsewhere herein, catenane structures are conceptually related to other mechanically-interlocked molecular architectures, such as rotaxanes, molecular knots or molecular Borromean rings.

Borromean rings are an example of a mechanically-interlocked molecular architecture in which three macrocycles are interlocked in such a way that breaking any macrocycle allows the others to disassociate.

The BORG frameworks comprising any of the foregoing general structural descriptions can be used for a multitude of purposes including, but not limited to, molecular electronics as logic molecular switching elements and as molecular shuttles. Controlling the position of the macrocycle allows the BORG to function as molecular switch with each possible location of the macrocycle corresponding to a different state. These BORG-based machines can be manipulated both by chemical and photochemical inputs. The BORG frameworks of the disclosure comprising, for example, pseudorotaxanes, rotaxanes, and catenane structures can be used in molecular purification, reactions, catalysts, molecular switches, electronic devices and molecular sensors.

The BORG frameworks of the disclosure can be designed to includes redox-active groups (e.g. viologen, TTF=tetrathiafulvalene), photoisomerizable groups (e.g. azobenzene), fluorescent groups and chiral groups.

Exemplary molecule selective groups can include, but are not limited to, ethers, crown ethers and their substituents and derivatives. Oxygen atoms in ethers or crown ethers can be replaced by S, $CR_1R_2$ or $NR_1$, wherein $R_1$, $R_2$ can be H or any organic group; this includes, for example, derivatives of EDTA (Diaminoethanetetraacetic acid). In the exemplary list of macrocycles below, it will be recognized that the length of the chain/cycle can be any length as will be recognized in the art. Furthermore, a BORG structure of the disclosure may comprise a homogenous or heterogeneous (i.e., combination) of the structures below. The dashed arrows are positions for connectivity to the underlying strut of a MOF. Exemplary macrocycles that can be linked to a MOF strut include molecules (or combinations thereof) selected from the group consisting of:

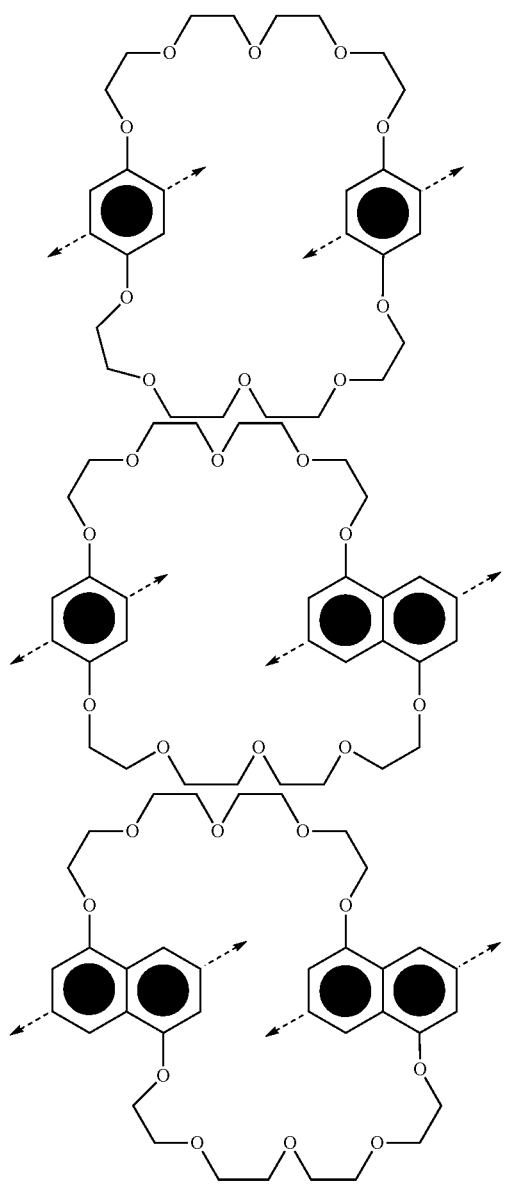

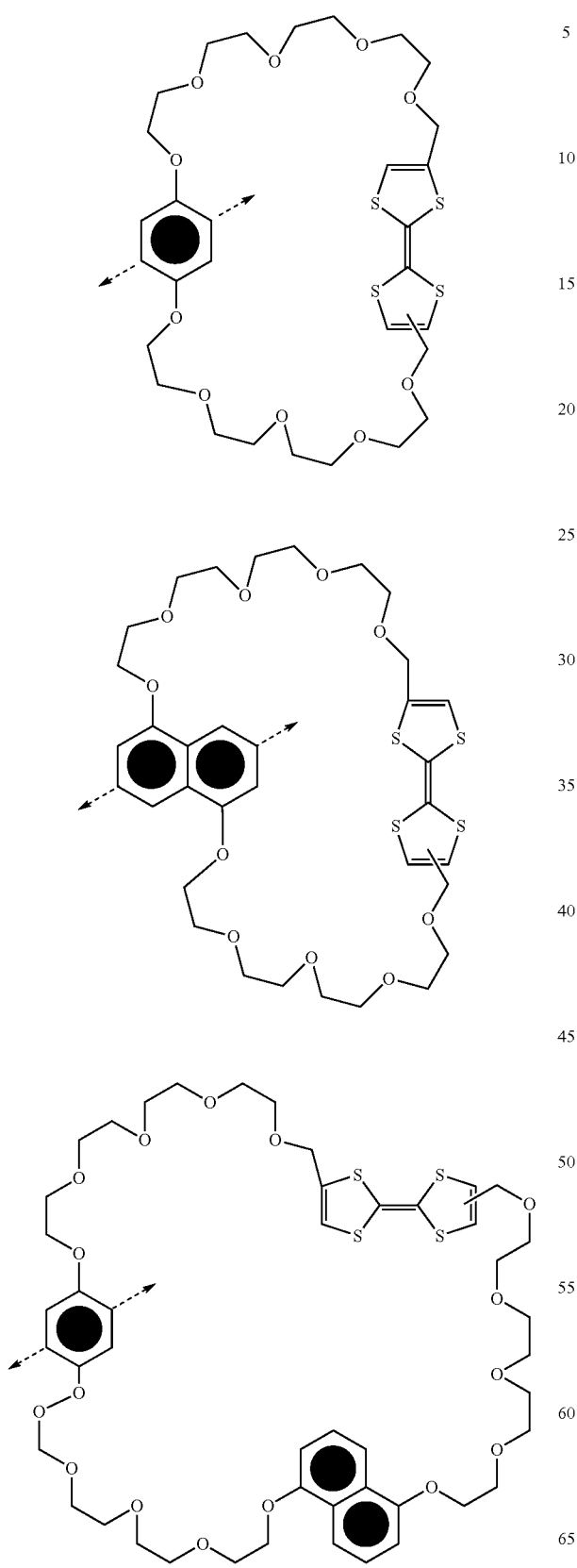
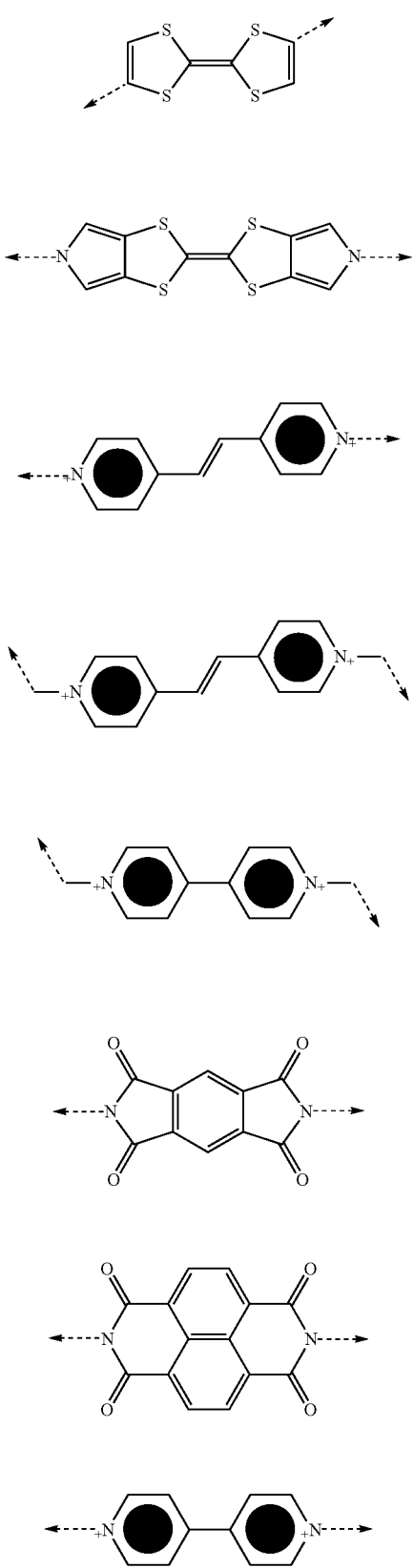

21
-continued
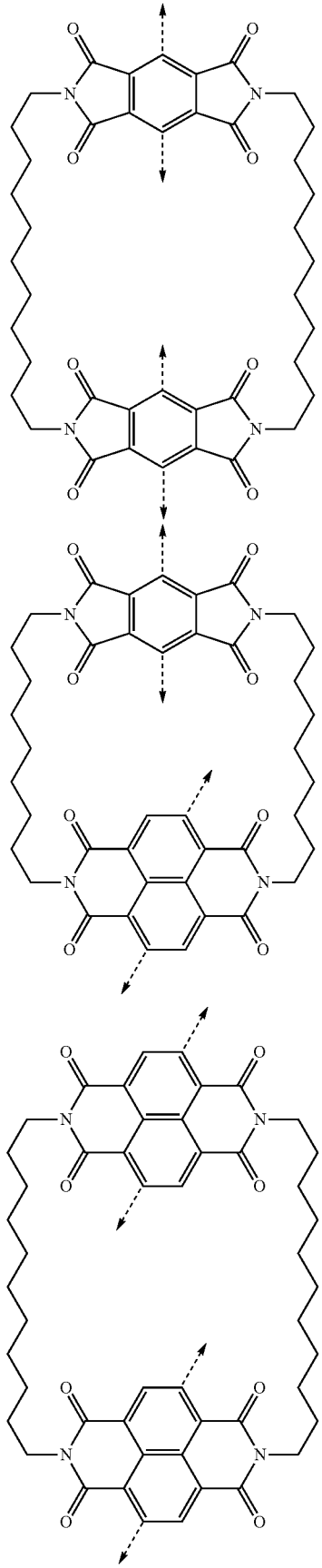
22
-continued
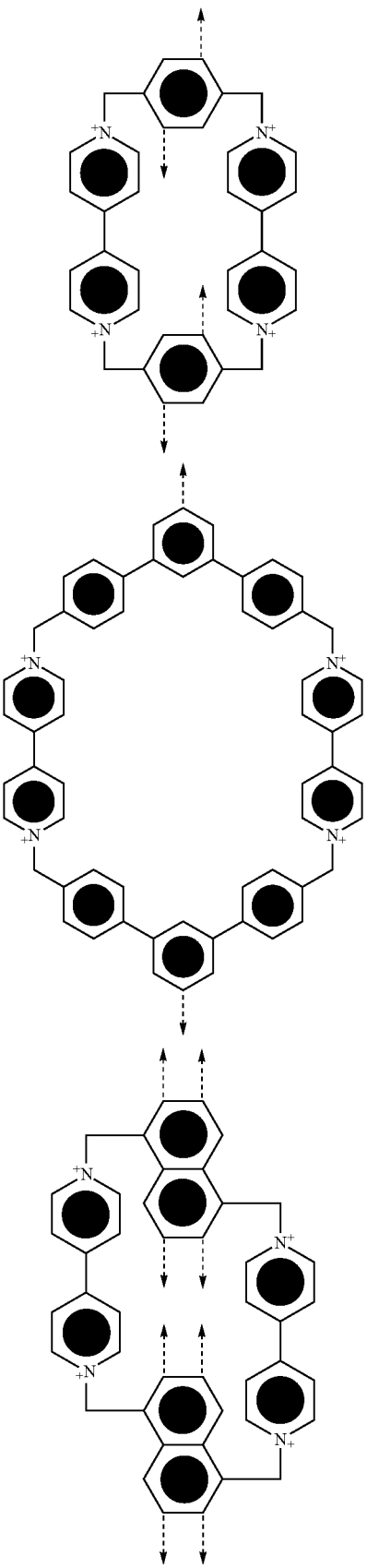

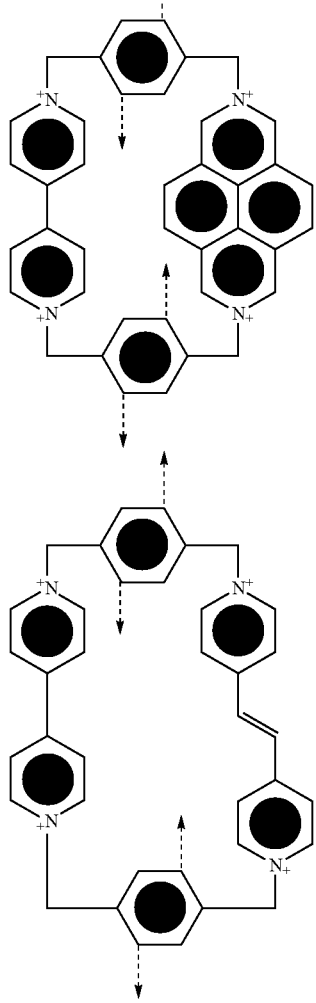
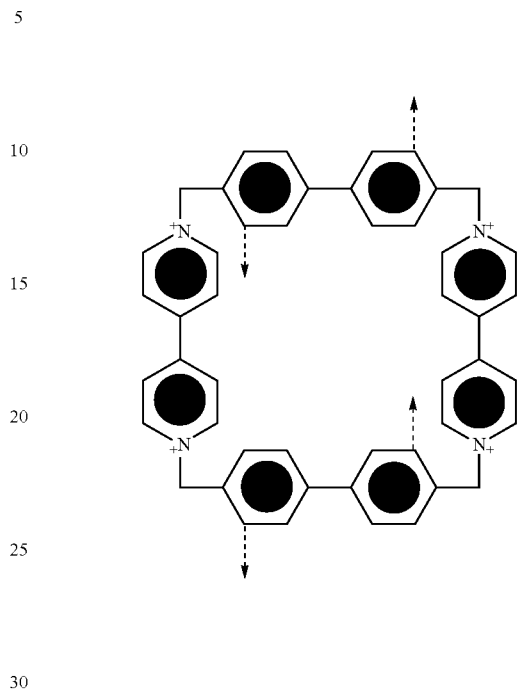
For example, macrocycles above can be covalently linked to a strut of an underlying MOF to generate a BORG. Exemplary struts comprising a macrocycle or polyether that can be used in the generation of BORGs can be selected from the group below (including combinations thereof):
I
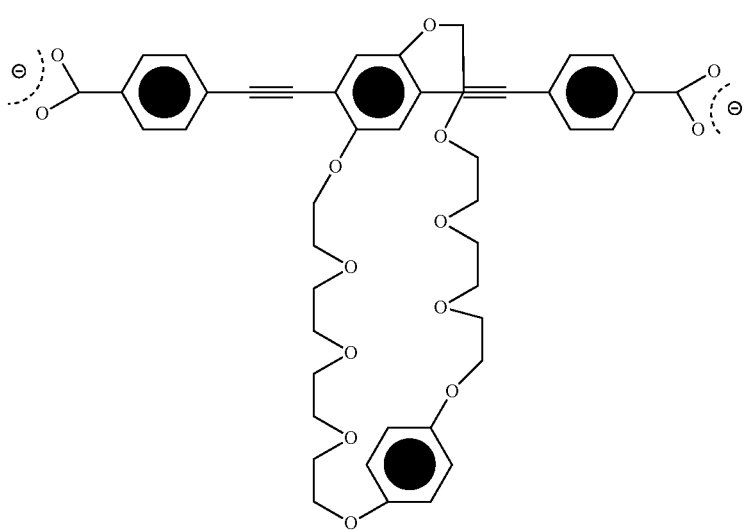

II
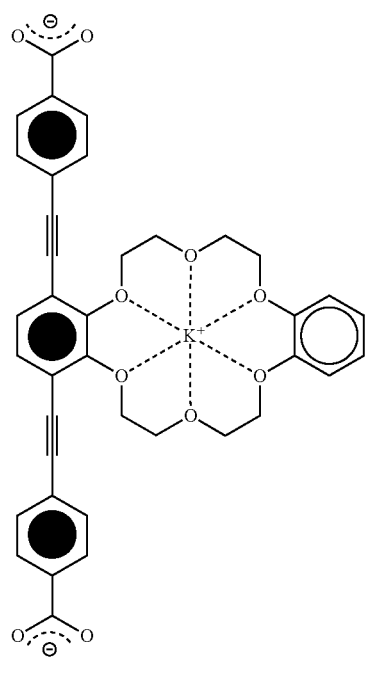
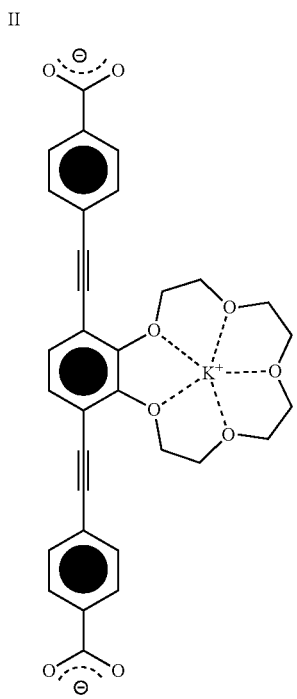
III
IV
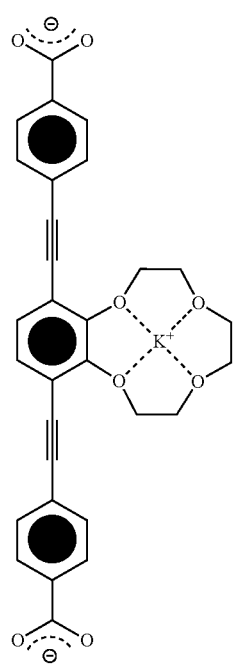
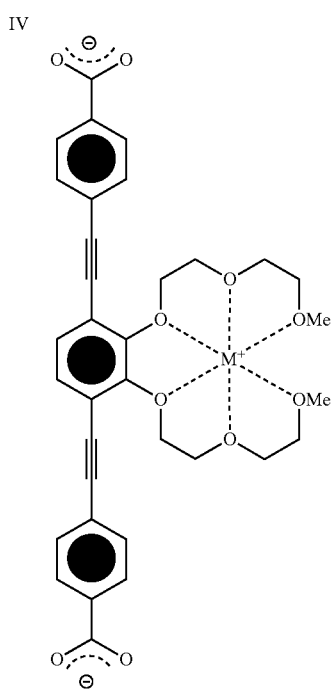
V

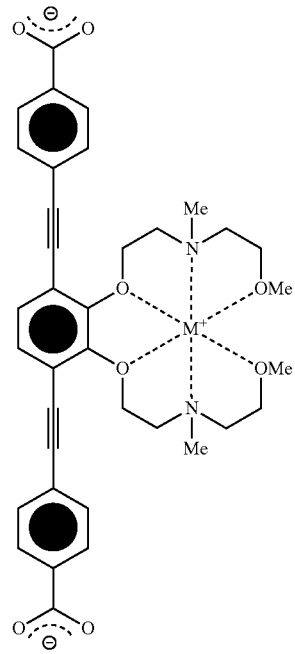
VI
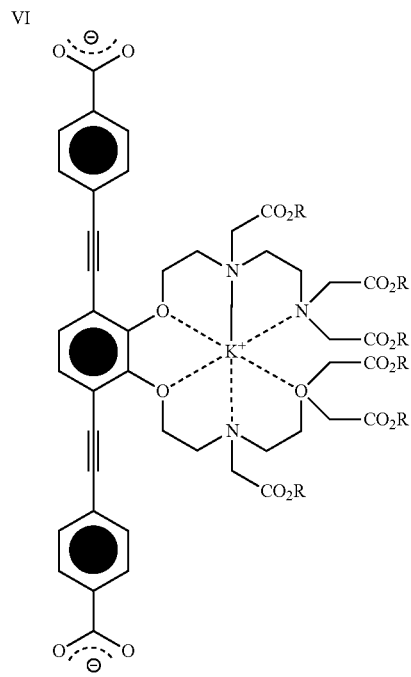
VII
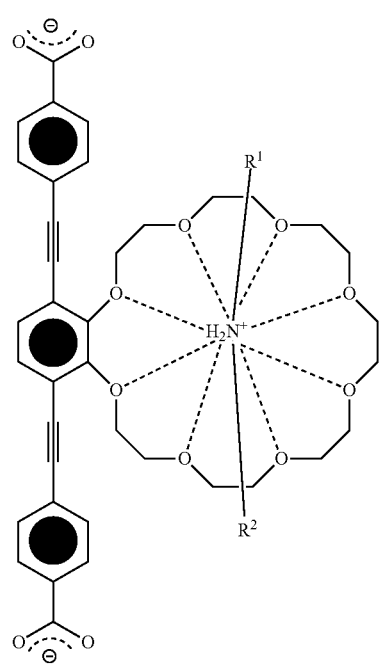
VIII
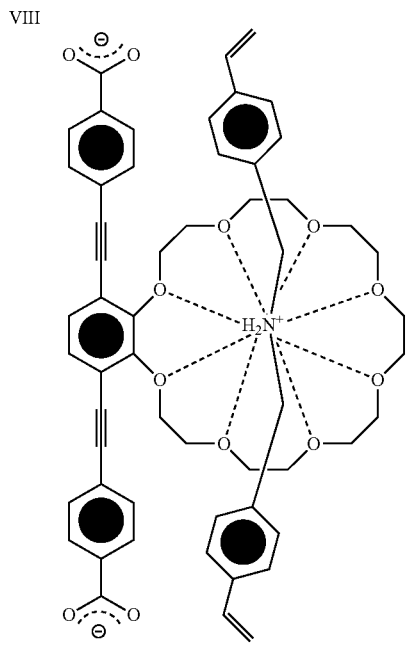
IX

X
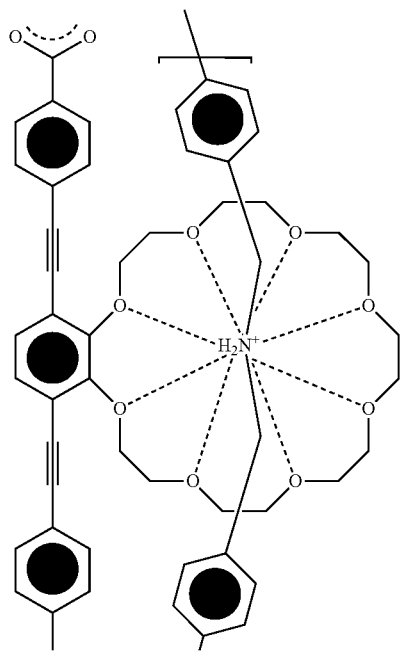
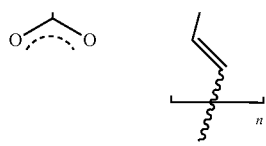
XI
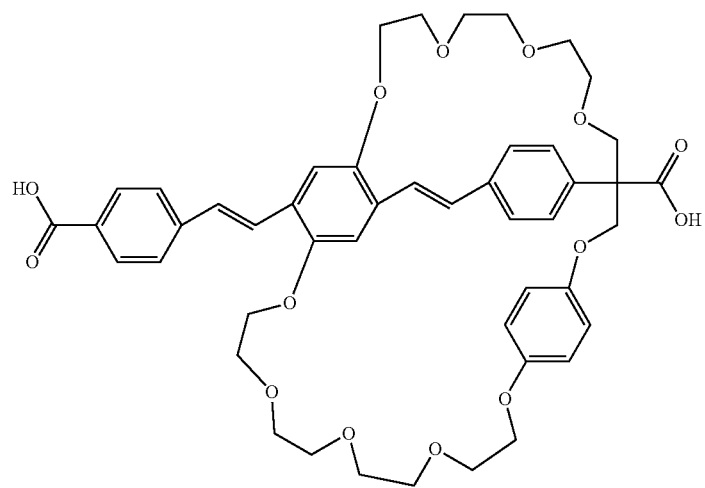

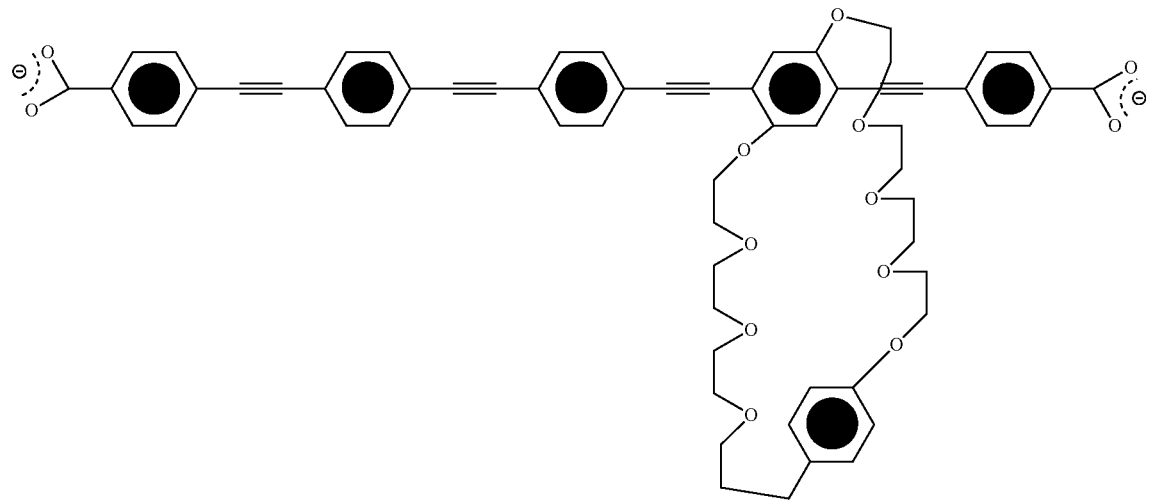
XII
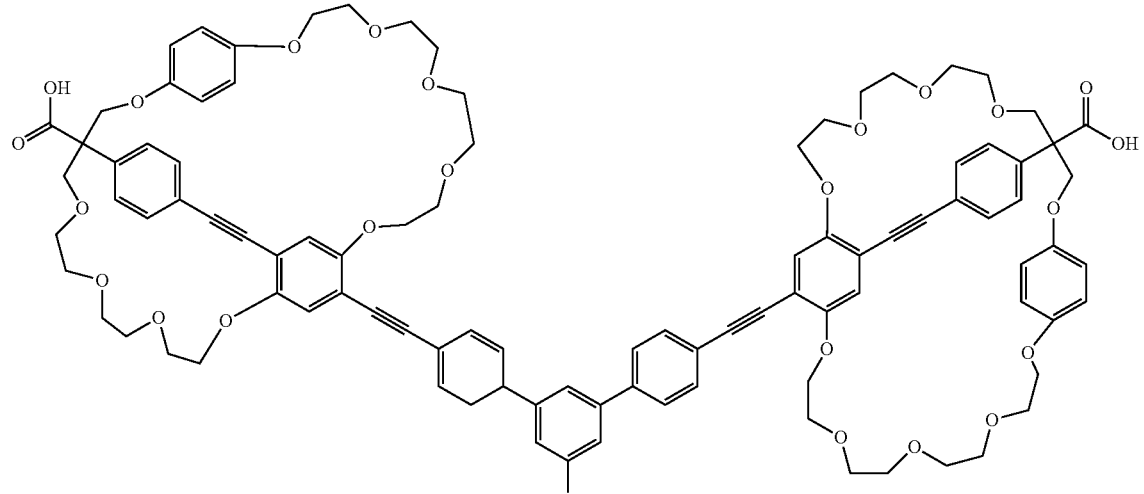
XIII
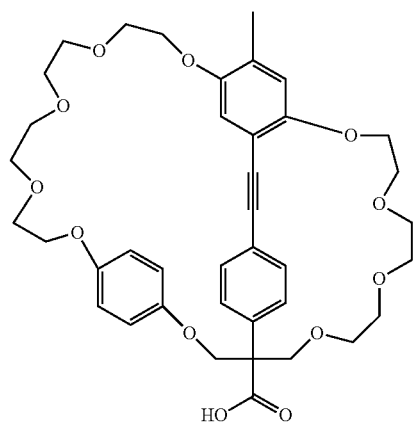

-continued
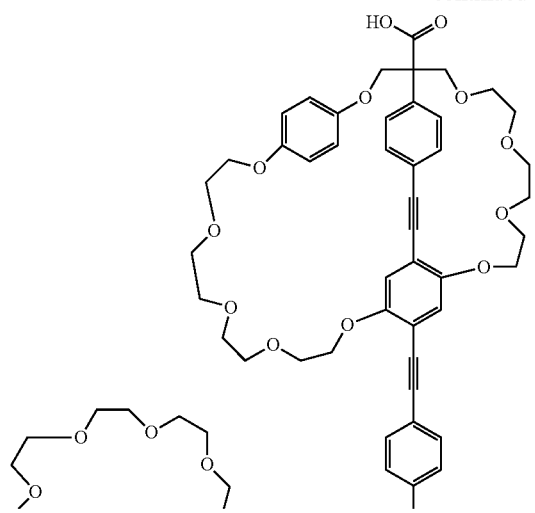
XIV
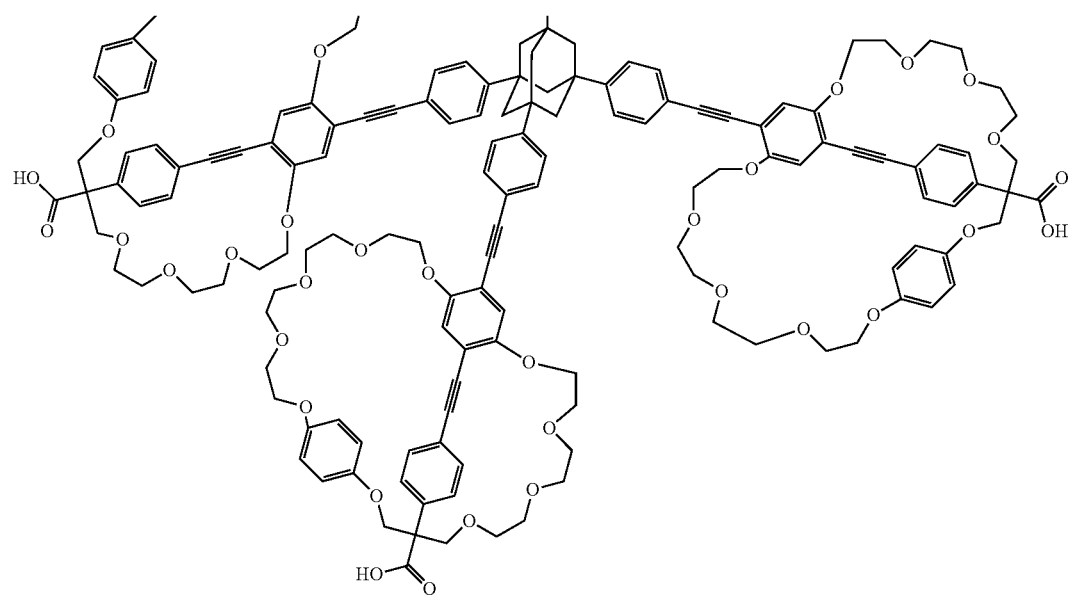
XV
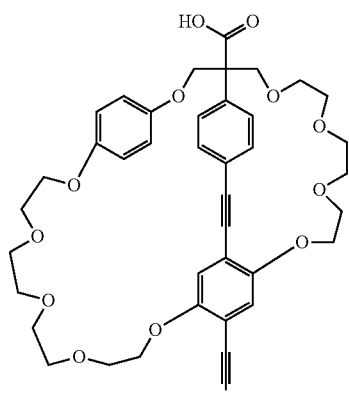

35
36
-continued
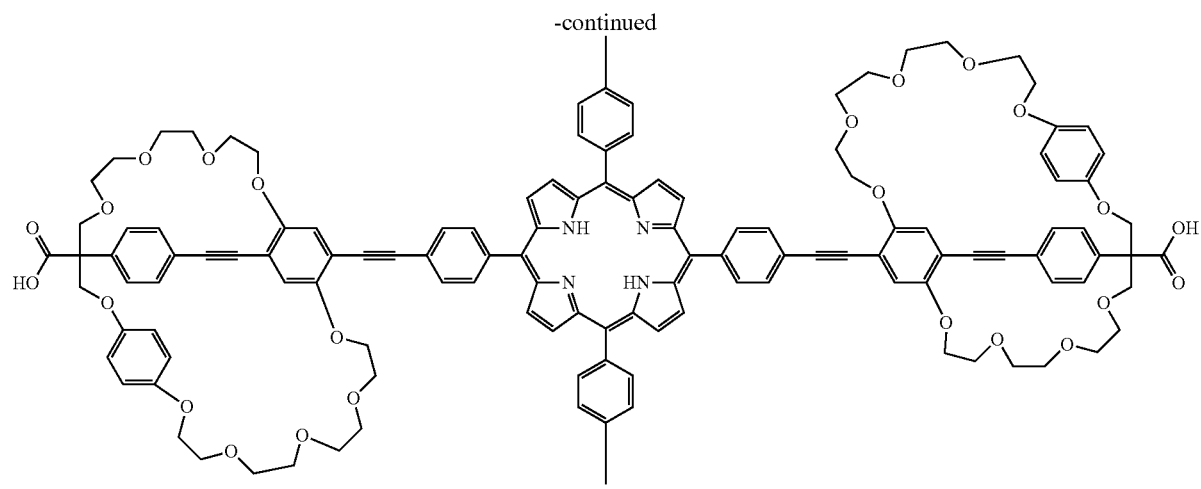
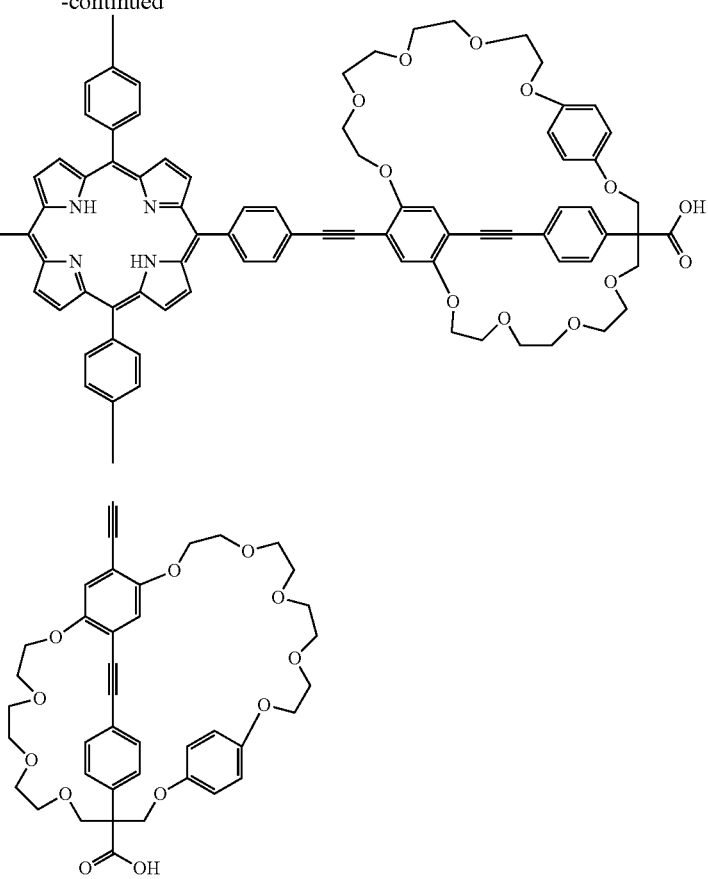
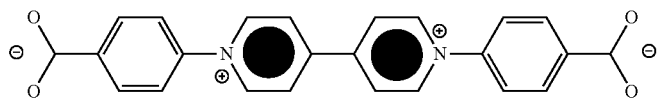
XVI
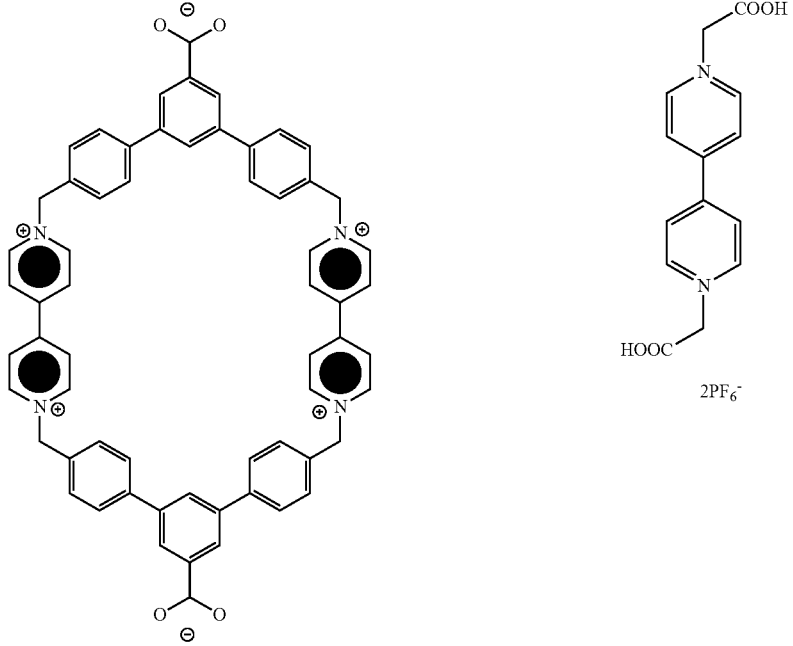
XVII
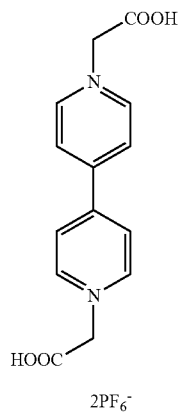
XVIII
2PF$_6^-$

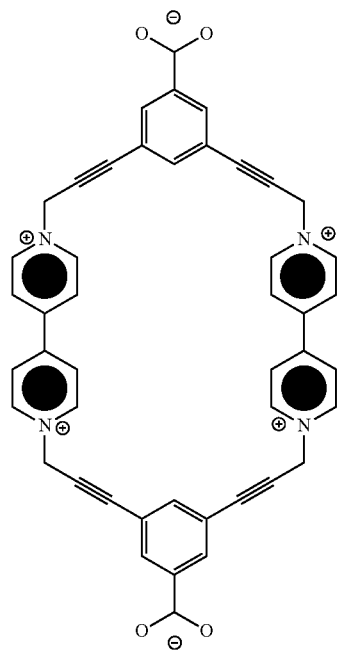
XIX
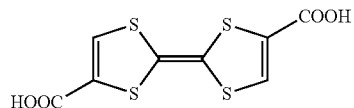
XX
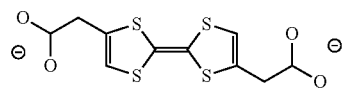
XXI
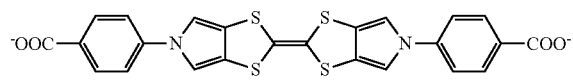
XXII
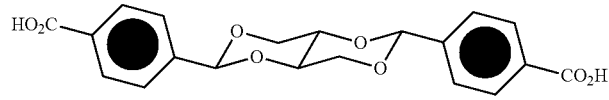
XXIII
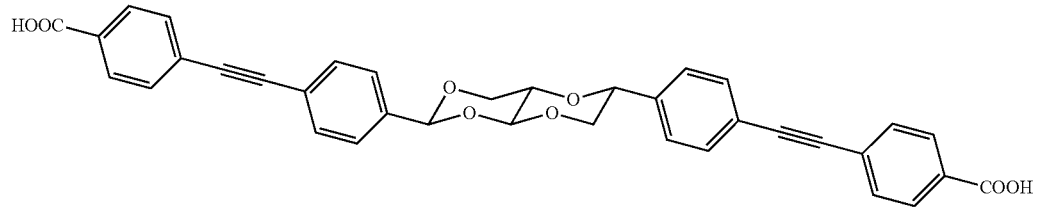
XXIV
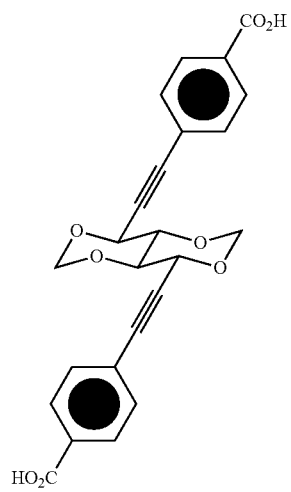
XXV Exemplary BORG switches can comprise a strut with a macrocycle as set forth below:
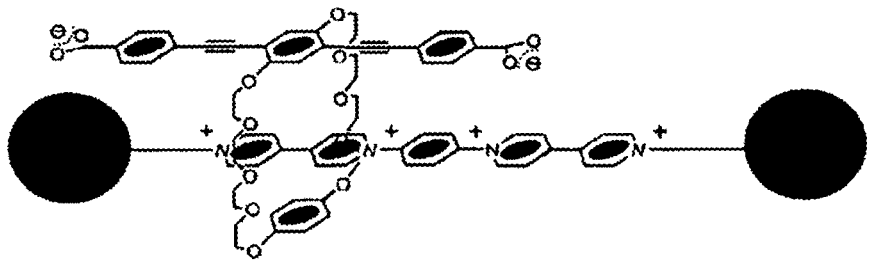
XXVI
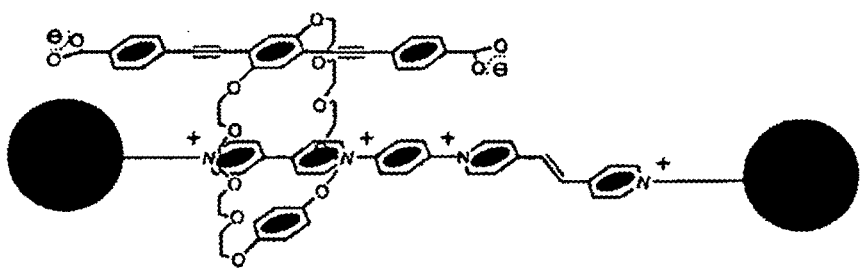
XXVII
Exemplary switchable BORGs comprising a macrocycle 40 with at least two different moieties or catenanes include, but are not limited to, struts comprising the structures below:
XXVIII
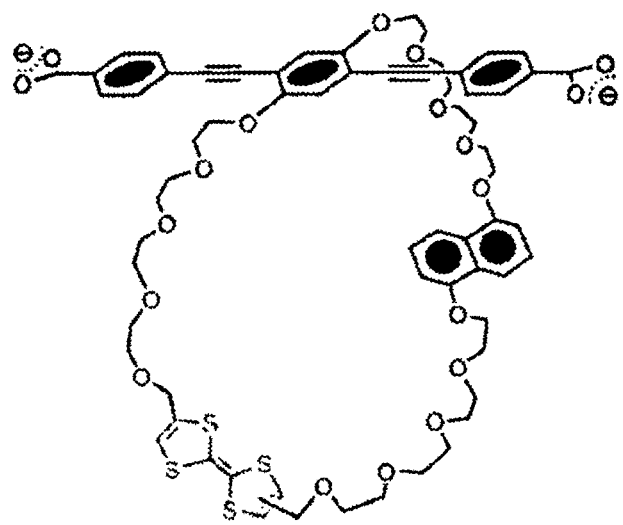

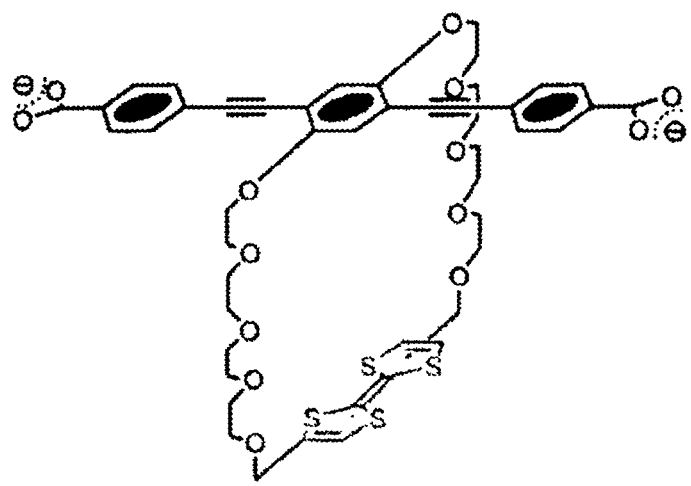
XXIX
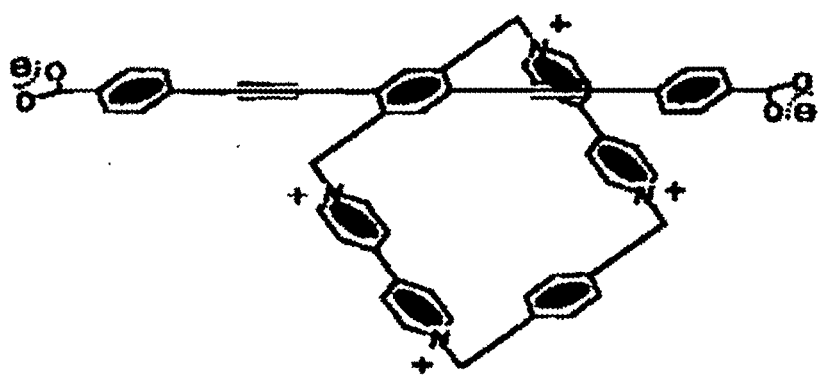
XXX
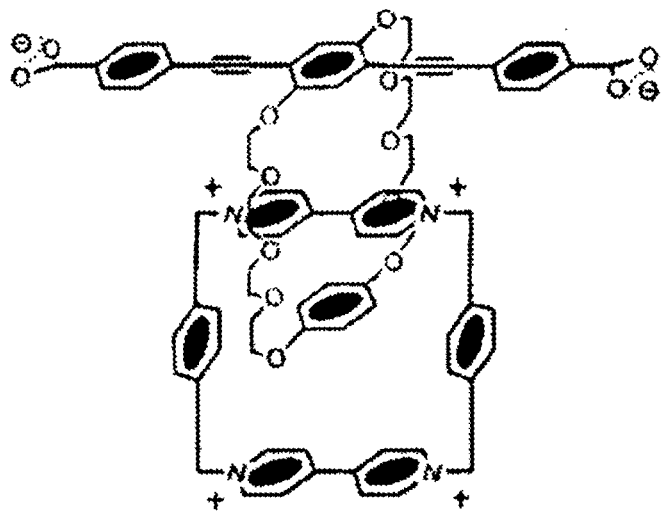
XXXI

-continued

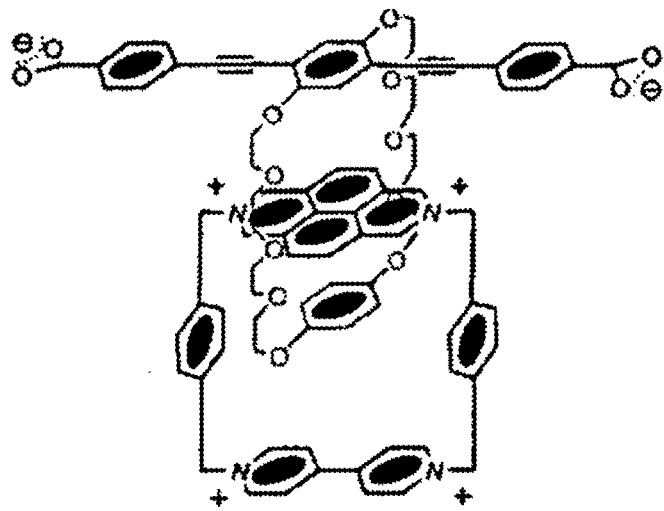

XXXII

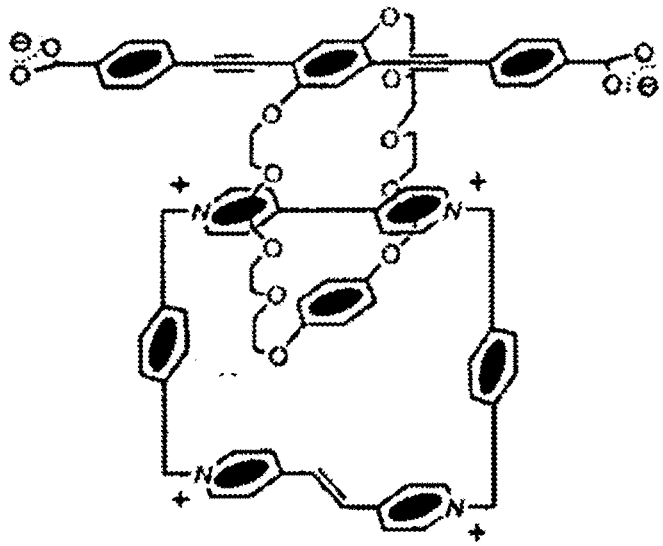

XXXIII

A framework of the disclosure can be synthesized by using solvothermal methods. For example, BORG-1 can be synthesized using metal ions having distinctly different coordination geometries, in combination with a linking moiety/strut possessing linking cluster function groups, and a suitable templating agent.

Metal ions that can be used in the synthesis of BORGs of the disclosure include $Li^+$, $Na^+$, $Rb^+$, $Mg^{2+}$, $Ca^{2+}$, $Sr^{2+}$, $Ba^{2+}$, $Sc^{3+}$, $Ti^{4+}$, $Zr^{4+}$, $Ta^{3+}$, $Cr^{3+}$, $Mo^{3+}$, $W^{3+}$, $Mn^{3+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Ni^{2+}$, $Ni^+$, $Pd^{2+}$, $Pd^+$, $Pt^{2+}$, $Pt^+$, $Cu^{2+}$, $Cu^+$, $Au^+$, $Zn^{2+}$, $Al^{3+}$, $Ga^{3+}$, $In^{3+}$, $Si^{4+}$, $Si^{2+}$, $Ge^{4+}$, $Ge^{2+}$, $Sn^{4+}$, $Sn^{2+}$, $Bi^{5+}$, $Bi^{3+}$, and combinations thereof, along with corresponding metal salt counter-anions.

The preparation of the BORGs of the disclosure can be carried out in either an aqueous or non-aqueous system. The solvent may be polar or non-polar as the case may be. The solvent can comprise the templating agent or the optional ligand containing a monodentate functional group. Examples of non-aqueous solvents include n-alkanes, such as pentane, hexane, benzene, toluene, xylene, chlorobenzene, nitrobenzene, cyanobenzene, aniline, naphthalene, naphthas, n-alcohols such as methanol, ethanol, n-propanol, isopropanol, acetone, 1,3-dichloroethane, methylene chloride, chloroform, carbon tetrachloride, tetrahydrofuran, dimethylformamide, dimethylsulfoxide, N-methylpyrollidone, dimethylacetamide, diethylformamide, thiophene, pyridine, ethanolamine, triethylamine, ethlenediamine, and the like. Those skilled in the art will be readily able to determine an appropriate solvent based on the starting reactants and the choice of solvent is not believed to be crucial in obtaining the materials of the disclosure.

Templating agents can be used in the methods of the disclosure. Templating agents employed in the disclosure are added to the reaction mixture for the purpose of occupying the pores in the resulting crystalline base MOF structure or BORG. In some variations of the disclosure, space-filling agents, adsorbed chemical species and guest species increase the surface area of the metal-organic framework. Suitable space-filling agents include, for example, a component selected from the group consisting of: (i) alkyl amines and their corresponding alkyl ammonium salts, containing linear, branched, or cyclic aliphatic groups, having from 1 to 20 carbon atoms; (ii) aryl amines and their corresponding aryl ammonium salts having from 1 to 5 phenyl rings; (iii) alkyl phosphonium salts, containing linear, branched, or cyclic aliphatic groups, having from 1 to 20 carbon atoms; (iv) aryl phosphonium salts, having from 1 to 5 phenyl rings; (v) alkyl organic acids and their corresponding salts, containing linear, branched, or cyclic aliphatic groups, having from 1 to 20 carbon atoms; (vi) aryl organic acids and their corresponding salts, having from 1 to 5 phenyl rings; (vii) aliphatic alcohols, containing linear, branched, or cyclic aliphatic groups, having from 1 to 20 carbon atoms; or (viii) aryl alcohols having from 1 to 5 phenyl rings.

Crystallization can be carried out by leaving the solution at room temperature or in isothermal oven for up to 300° C.; adding a diluted base to the solution to initiate the crystallization; diffusing a diluted base into the solution to initiate the crystallization; and/or transferring the solution to a closed vessel and heating to a predetermined temperature.

Typically, the precursor MOF or BORG is heated to a temperature from about 30° C. to about 300° C. In another variation, the one or more templating agents are removed by exposing the precursor MOF or BORG to a vacuum. Typically, the vacuum is characterized by having a pressure less than $10^{-3}$ torr. In other variations, from about $10^{-5}$ torr to about 700 torr. In still another variation of the disclosure, the one or more ligands are removed by simultaneously heating the precursor MOF or BORG and by exposing the precursor MOF or BORG to a vacuum. In still another variation, the solution used in the method of the disclosure may also include space-filling agents. Examples of suitable space-filling agents are set forth above. In a refinement of each of these variations, one or more ligands of the precursor MOF or BORG may be exchanged with another agent or agents that are more easily removed by subsequent heating and/or exposure to a vacuum.

In another embodiment, the framework set forth above may include an interpenetrating framework that increases the surface area of the framework. Although the frameworks of the disclosure may advantageously exclude such interpenetration, there are circumstances when the inclusion of an interpenetrating framework may be used to increase the surface area. An exemplary interpenetrating framework includes MOF-1000 described herein.

The frameworks of the disclosure can be used as sorption devices. Sorption is a general term that refers to a process resulting in the association of atoms or molecules with a target material. Sorption includes both adsorption and absorption. Absorption refers to a process in which atoms or molecules move into the bulk of a porous material, such as the absorption of water by a sponge. Adsorption refers to a process in which atoms or molecules move from a bulk phase (that is, solid, liquid, or gas) onto a solid or liquid surface. The term adsorption may be used in the context of solid surfaces in contact with liquids and gases. Molecules that have been adsorbed onto solid surfaces are referred to generically as adsorbates, and the surface to which they are adsorbed as the substrate or adsorbent. Adsorption is usually described through isotherms, that is, functions which connect the amount of adsorbate on the adsorbent, with its pressure (if gas) or concentration (if liquid). In general, desorption refers to the reverse of adsorption, and is a process in which molecules adsorbed on a surface are transferred back into a bulk phase.

The metal-organic frameworks used in the embodiments of the disclosure include a plurality of pores for adsorption of a biological molecule or gas. In one variation, the plurality of pores has a unimodal size distribution. In another variation, the plurality of pores have a multimodal (e.g., bimodal) size distribution. In the case of a BORG the pore comprises a selective group capable of specifically binding a particular size, shape or charged entity. The BORG can be designed to be selective by incorporating a particular macrocycle or other stereoselective molecular entity into the underlying MOF. Such designing conjugates or links the stereoselective molecular entity to a strut of the underlying MOF, wherein the molecular entity extends into at least one pore of the MOF.

Advantageously, the BORG framework includes one or more sites for binding or storing a biological molecule or gas. Thus the BORGs of the disclosure can serve as gas storage materials. Gases that may be stored in the gas storage material of the disclosure include gas molecules comprising available electron density for attachment to the one or more sites for storing gas. Suitable examples of such gases include, but are not limited to, the gases comprising a component selected from the group consisting of ammonia, argon, carbon dioxide, carbon monoxide, hydrogen, and combinations thereof. In one variation of this embodiment, the accessible metal site is an open metal site.

Furthermore, the BORGs of the disclosure may be used as sensing materials. For example, interaction of a BORG with a particular analyte can cause a change in the composition, electronics or optics of the BORG. Such changes can be detected using an appropriate transducing agent (e.g., a current flowing through the material to detect conductivity changes, an acoustic tranducer or balance to detect mass changes, or an optical detector to detect changes in color). An example of the sensing of such BORGs is illustrated by BORG-1 upon absorption and desportion of $PQT^{2+}$.

The following examples are intended to illustrate but not limit the disclosure. While they are typical of those that might be used, other procedures known to those skilled in the art may alternatively be used.

EXAMPLES

Chemicals were purchased from commercial suppliers and used as received, unless otherwise noted. Dry solvents were obtained from an EMD Chemicals DrySolv® system. Thin-layer chromatography (TLC) was carried out using glass plates, precoated with silica gel 60 with fluorescent indicator (Whatman LK6F). The plates were inspected by UV light (254 nm). Column chromatography was carried out using silica gel 60F (230-400 mesh). $^1H$, $^{13}C$, and $^{15}N$ NMR spectra were recorded on ARX500 (500 MHz), DRX500 (500 MHz) or AV600 (600 MHz) spectrometers with the residual solvent as the internal standard. The chemical shifts were listed in ppm on the S scale and coupling constants were recorded in Hertz (Hz). The following abbreviations were used to explain the multiplicities: s, singlet; d, doublet; t, triplet; q, quartet; b, broad peaks; m, multiplet or overlapping peaks. High-resolution electrospray ionization (ESI) mass spectra were measured on a Micromass Q-T of Ultima (SCS, University of Illinois).

As a demonstration of the BORG frameworks of the disclosure, three long organic struts (19.3 Å) incorporating 34- and 36-membered macrocyclic polyethers as recognition modules were used in the construction of several crystalline primitive cubic frameworks. BORG-1, for example, is capable of docking paraquat dications ($PQT^{2+}$) into each of the macrocyclic polyethers units located within its struts in a highly specific and stereoelectronically controlled fashion. This act of specific complexation yields the corresponding BORG-1 pseudorotaxanes, as confirmed by X-ray diffraction and solid-state/solution NMR spectroscopic studies performed on BORG-1, its pseudorotaxanes, and their molecular strut analogues. A control experiment involving the attempted inclusion of $PQT^{2+}$ inside a framework (MOF-177) devoid of polyether struts showed negligible uptake of $PQT^{2+}$ dications, indicating the macrocyclic polyether docking of $PQT^{2+}$. Fundamentally, BORG constructs place active units (e.g., macrocyclic polyether docking sites) in a regular three-dimensional array, making them fully addressable in a selective, cohesive, and reproducible manner.

Figure 2:
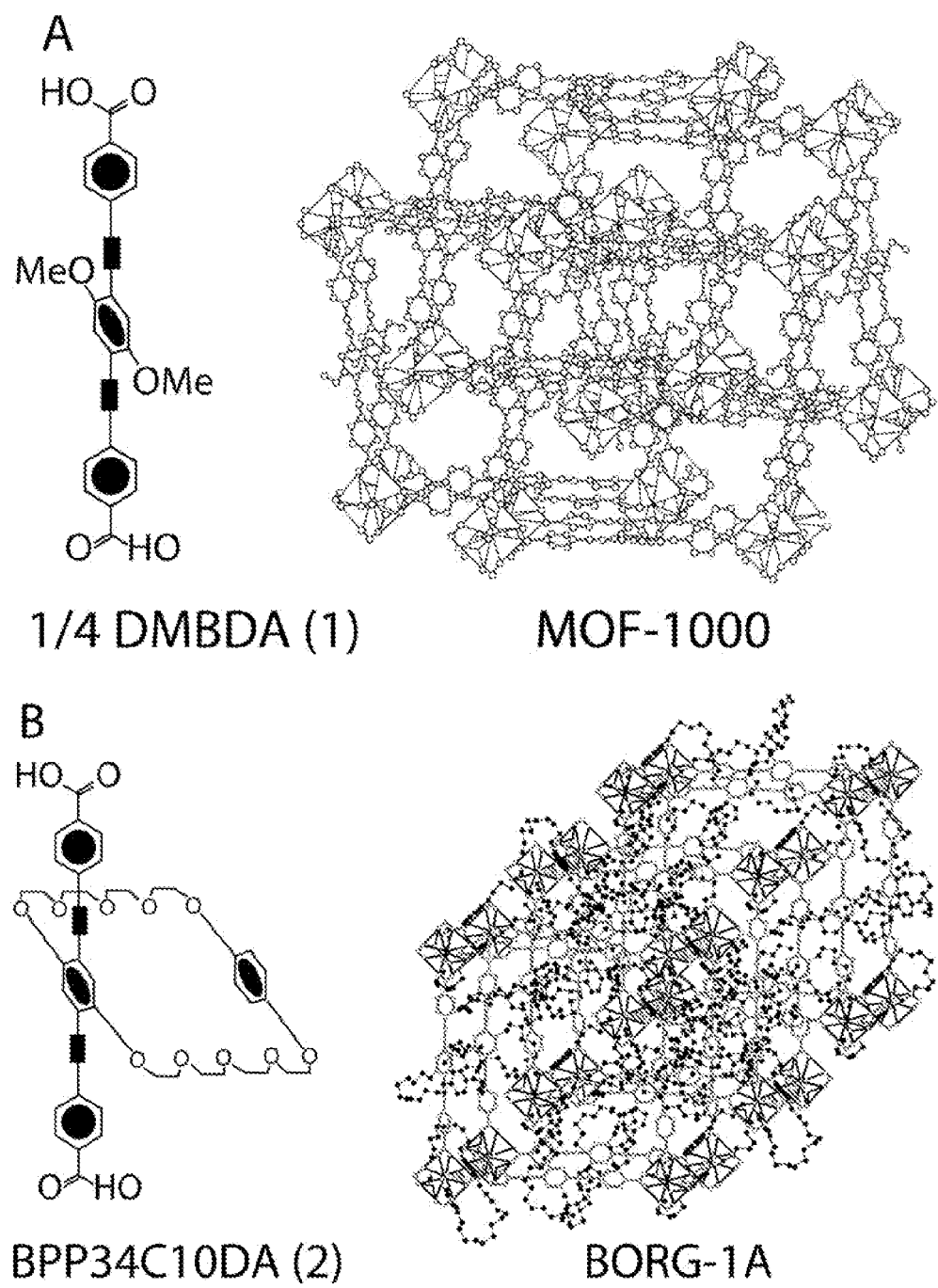
FIG. 2. Ball-and-stick drawings of crystal structures of MOF-1000, BORG-1A, BORG-1, BORG-2, and their corresponding organic struts. MOF-1000 (A) is a four-fold interpenetrating structure with different nets shown in four different colors. Single X-ray crystallography revealed BORG-1A (B) as a triply interpenetrating cubic structure (shown in blue, gold and gray), with polyethers represented by red balls and wires. BORG-1 (C) and BORG-2 (D) share the identical cubic framework backbone, and different crown ethers are placed precisely throughout the whole network ($Zn_4O$ $(COO)_6$ polyhedra, blue; organic struts, gray; crown ethers, red). Crown ethers in all the structures were modeled by $Cerius^2$. All hydrogen atoms have been omitted for clarity.
Figure 2:
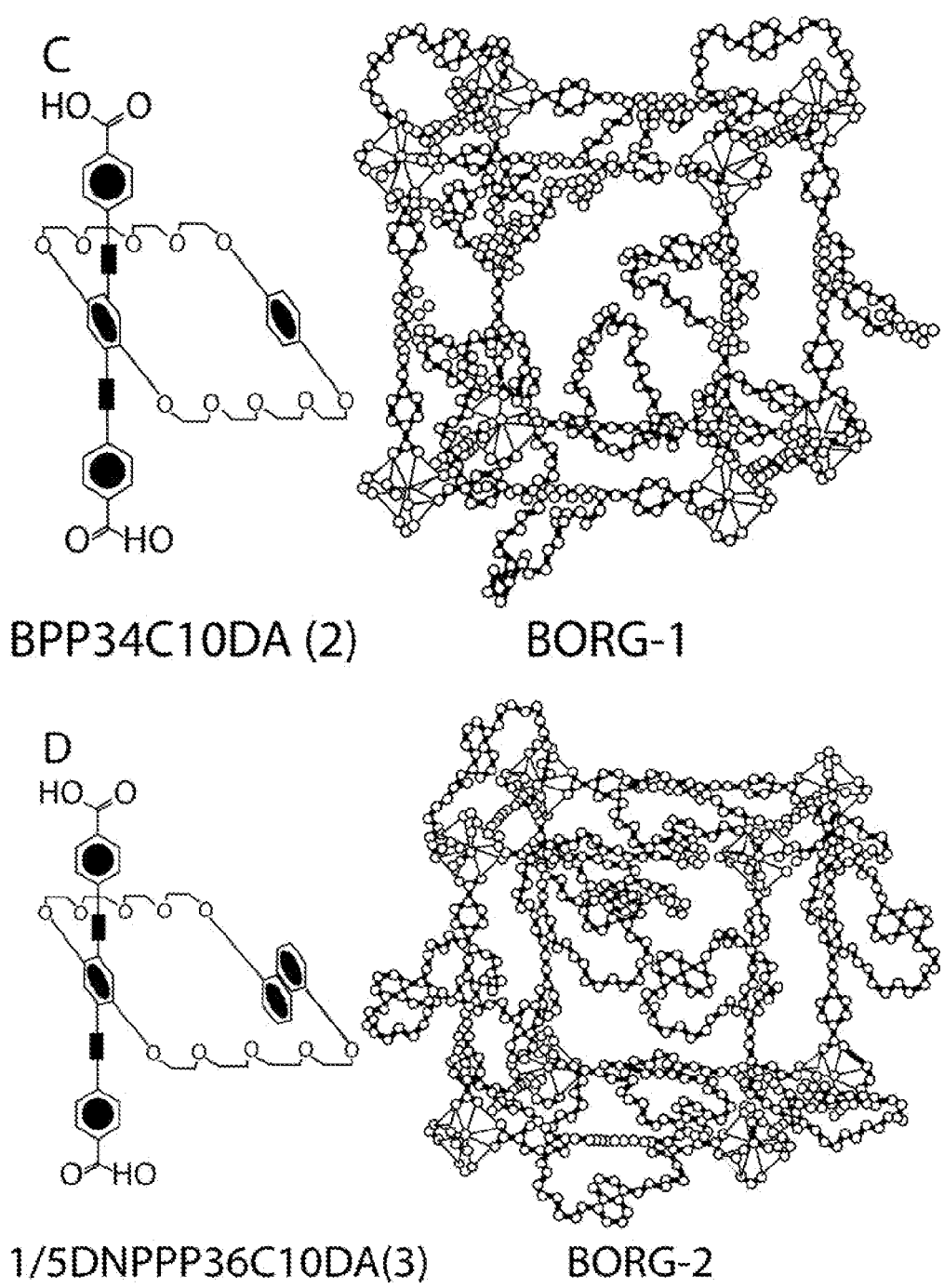

Primitive cubic topology of the archetypical MOF-5 was used, in which benzene struts are joined by $Zn_4O(CO_2)_6$ cluster joints. Initially, the feasibility of using the long 1/4DMBDA to make MOF-1000, which has the MOF-5 topology, albeit quadruply interpenetrated was demonstrated (FIG. 2A). This approach was extended to the more complex struts, BPP34C10DA and 1/5DNPPP36C10DA, which are known to act as electron-rich receptors for electron-deficient substrates, to make the corresponding BORG-1A, BORG-1 and BORG-2 (FIG. 2, B to D). Indeed each of the crown ether receptors in BORG-1 is addressable as evidenced by the docking of the paraquat dication ($PQT^{2+}$) at every one of the receptor sites. In contrast to known MOFs where the frameworks are used mainly as passive platforms for the adsorption of gases and molecules, BORG-1 not only has active components in precise recognition sites but also, by virtue of the openness of its structure, allows substrates to diffuse freely from solution, through the pores, and finally dock at these active domains.

Figure 5:
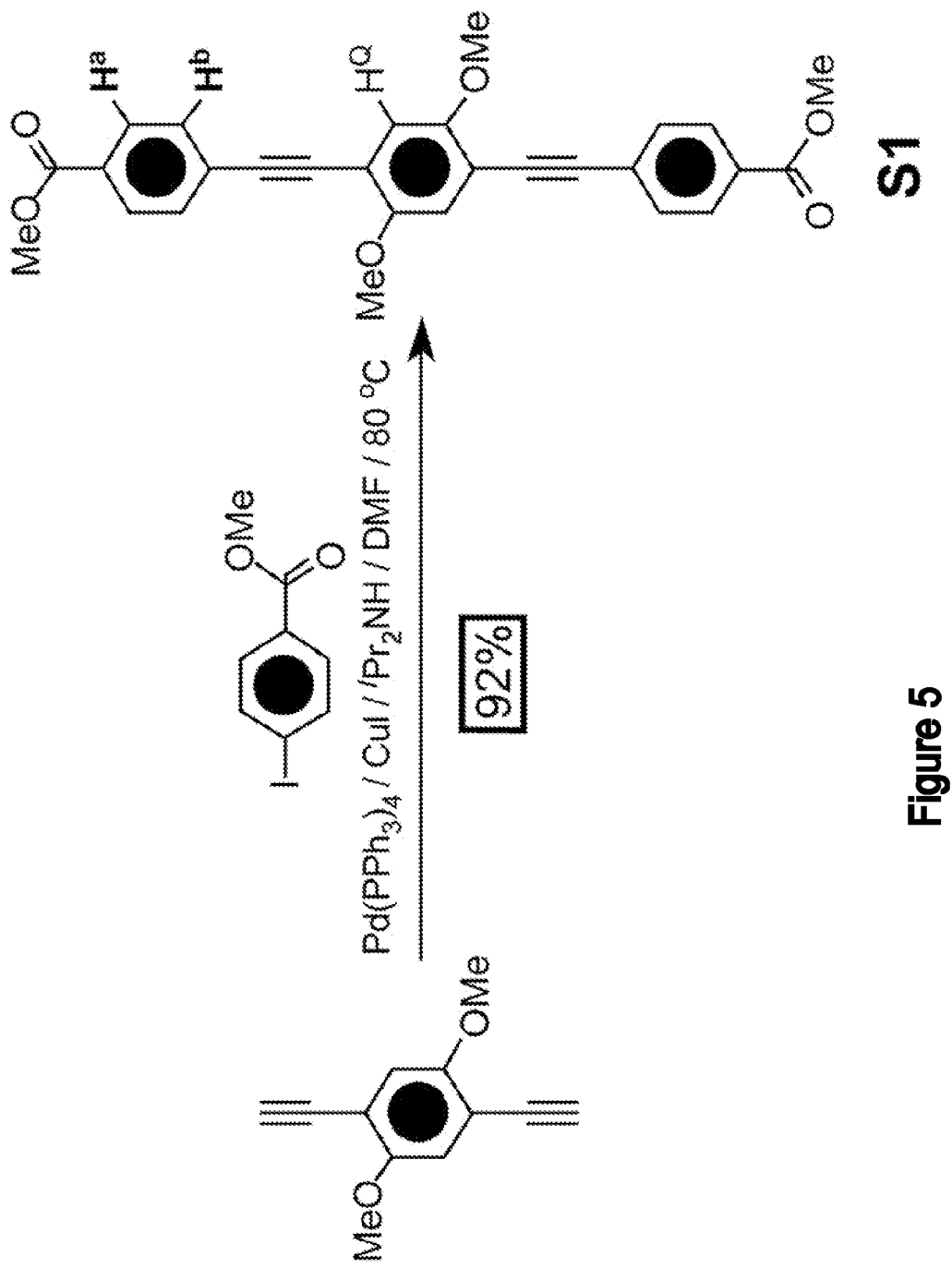
FIG. 5. Shows a scheme for the synthesis of intermediate S1.
Figure 6:
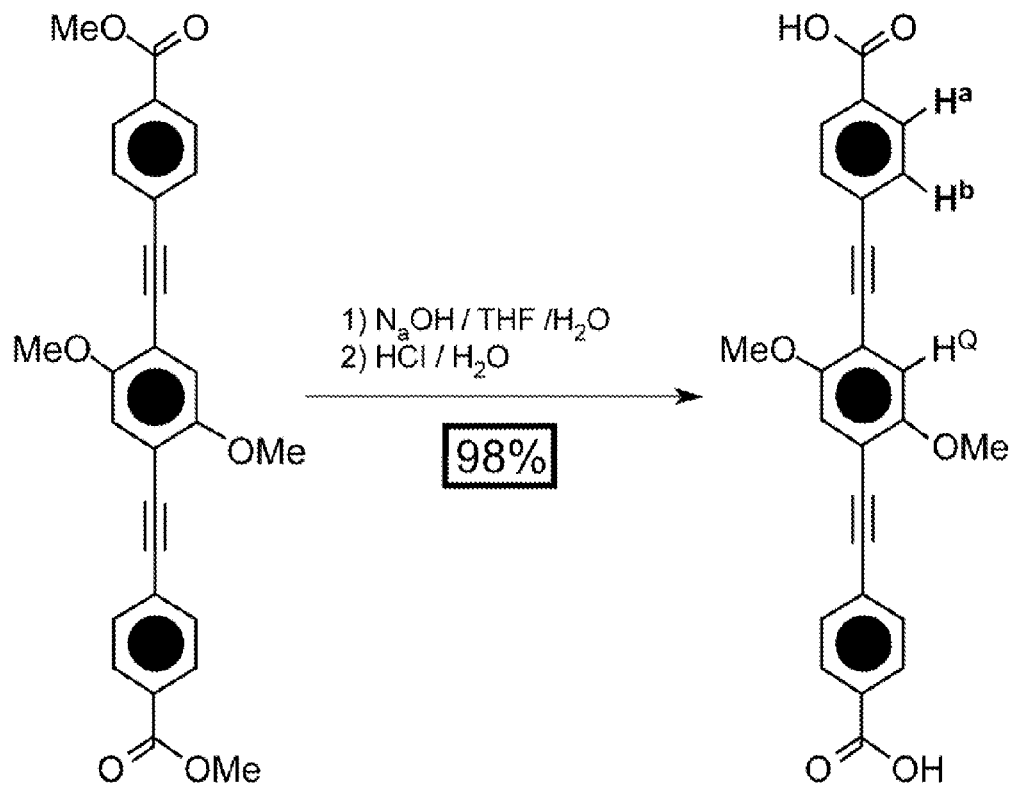
FIG. 6. Shows a scheme for the synthesis of intermediate S1.

Strut synthesis. Strut 1 (S1) was synthesized by the attachment of 4-(carboxyphenyl)ethynyl groups to the 2- and 5-positions of a central 1,4-dimethoxybenzene ring using the Pd-catalyzed alkyne-aromatic Sonogashira coupling (see FIGS. 5 and 6). Methyl 4-iodobenzoate (10.5 g, 40 mmol), $Pd(PPh_3)_4$ (0.46 g. 0.4 mmol), and CuI (0.16 g, 0.8 mmol) were added to a mixture of $iPr_2NH$ (15 mL) and DMF (100 mL). The mixture was purged with Ar while stirring for 30 min before a solution of 1,4-diethynyl-2,5-dimethoxybenzene (3.70 g, 20 mmol) (1) in DMF (40 mL) was slowly added. The mixture was stirred for 8 h at 80° C. After cooling to room temperature, the insoluble material was collected by filtration, and then washed with $H_2O$ (350 mL) and MeOH (100 mL). The yellow solid was dissolved in $CHCl_3$ (1200 mL) and washed with $H_2O$ (300 mL) and dried ($MgSO_4$). The solvent was removed in vacuo to afford the product S3 (8.38 g, 92%) which was employed in the next step without further purification. $^1$H NMR (500 MHz, $CDCl_3$): δ=8.02 (d, 4H, Ar—H$^a$, $^3J$=8.4 Hz), 7.62 (d, 4H, Ar—H$^b$, $^3J$=8.4 Hz), 7.04 (s, 2H, Ar—HQ), 3.93 (s, 6H, $COOCH_3$), 3.91 (s, 6H, $OCH_3$). $^{13}$C NMR (125 MHz, $CDCl_3$): δ=166.4, 153.9, 131.5, 129.5, 129.4, 127.7, 115.5, 113.2, 94.3, 88.4, 56.4, 52.1. HiRes MS (ESI-TOF): Calcd. for [M+H]$^+$ $C_{28}H_{23}O_6^+$ m/z=455.1489; found m/z=455.1492. S1 (1.00 g, 2.20 mmol) and NaOH (0.35 g, 8.80 mmol) were dissolved in a mixture of THF (50 mL) and H2O (50 mL). The solution was stirred at room temperature overnight. The pH of the solution was then adjusted to 2 with aqueous HCl solution (1 M) while a precipitate formed. The precipitate was collected by filtration, washed with $H_2O$, and dried in air to afford the product 1 (0.920 g, 98%). $^1$H NMR (500 MHz, CD3SOCD3): δ=13.18 (s, 2H, COOH), 7.98 (d, 4H, Ar—H$^a$, $^3J$=8.5 Hz), 7.66 (d, 4H, Ar—H$^b$, $^3J$=8.5 Hz), 7.25 (s, 2H, Ar—HQ), 3.87 (s, 6H, OCH3). $^{13}$C NMR (125 MHz, CD3SOCD3) δ=167.9, 154.0, 131.8, 131.0, 129.9, 127.0, 116.0, 112.8, 94.4, 89.0, 56.7. HiRes MS (ESI-TOF): Calcd. for [M+H]$^+$ $C_{26}H_{19}O_6^+$ m/z=427.1176; found m/z=427.1176.

Figure 7:
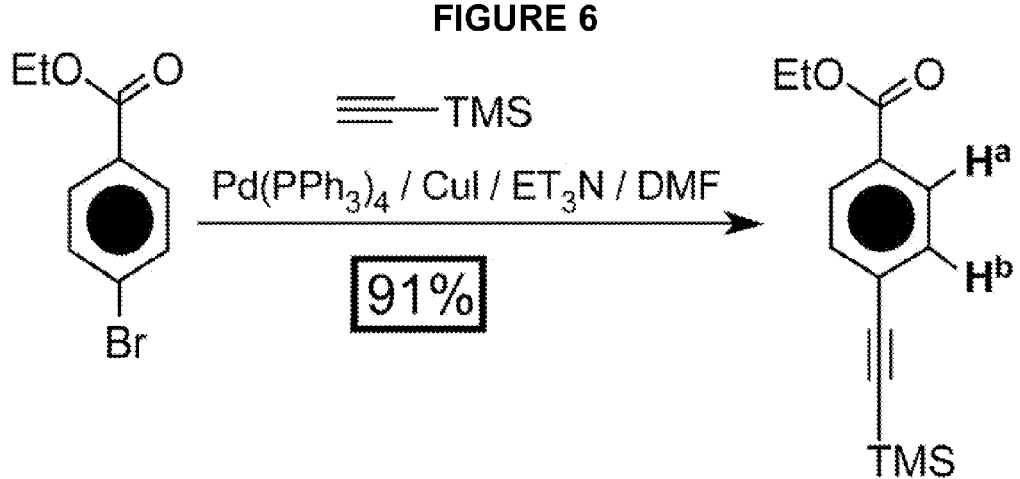
FIG. 7. Shows a scheme for the synthesis of S2.

S2: Ethyl 4-bromobenzoate (2.00 g, 8.73 mmol) was dissolved in DMF (80 mL) and $iPr_2NH$ (20 mL). Under Ar protection, TMS acetylene (1.29 g, 13.1 mmol), $Pd(PPh_3)_4$ (0.504 g, 0.437 mmol), and CuI (0.0430 g, 0.437 mmol) were added to the solution. The mixture was then stirred under Ar at 80° C. for 48 h. The solvent was then removed in vacuo. The residue was then dissolved in $CH_2Cl_2$ (50 mL) before being washed with $H_2O$ (20 mL×2) and brine (20 mL). The organic phase was then dried ($Na_2SO_4$). The solvent was removed in vacuo. Column chromatography ($SiO_2$: Hexanes/CH2Cl2=3:1) provided the product S2 as a yellow solid (2.03 g, 94%). $^1$H NMR (500 MHz, $CDCl_3$): δ=7.77 (d, 2H, Ar—H$^a$, $^3J$=8.7 Hz), 7.51 (d, 2H, Ar—H$^b$, $^3J$=8.7 Hz), 4.37 (q, 2H, $OCH_2CH_3$, $^3J$=7.1 Hz), 1.39 (t, 3H, $OCH_2CH_3$, $^3J$=7.1 Hz), 0.26 (s, 9H, $Si(CH_3)_3$). $^{13}$C NMR ($CDCl_3$, 125 MHz): δ=166.4, 132.2, 130.4, 129.7, 128.0, 104.5, 98.0, 61.5, 14.7, 0.20. HiRes MS (ESI-TOF): Calcd. for [M+H]$^+$ $C_{14}H_{19}O_2Si^+$ m/z=247.1149; found m/z=247.1147. (see, e.g., FIG. 7).

Figure 8:
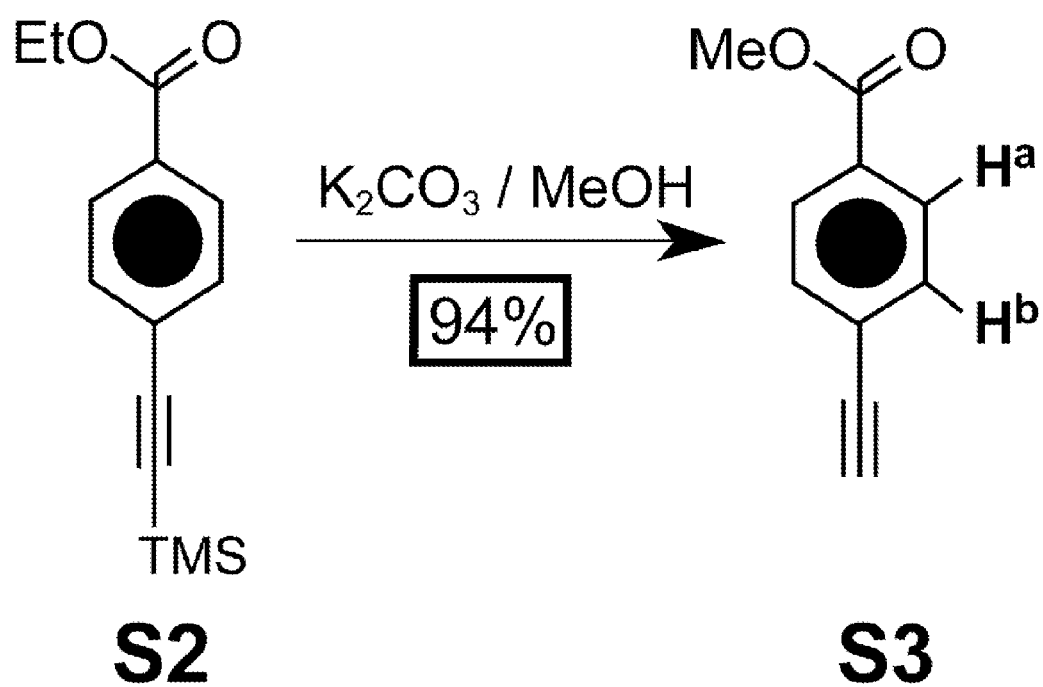
FIG. 8. Shows a scheme for the synthesis of S3.

S3: $K_2CO_3$ (0.426 g, 3.044 mmol) was added to a solution of S2 (0.250 g, 1.01 mmol) in MeOH (10 mL) and stirred at room temperature for 2 h. The solid material was isolated by filtration and the solvent was removed in vacuo. The residue was then dissolved in $CH_2Cl_2$ (5 mL) before being washed with $H_2O$ (3 mL×2) and brine (3 mL). The organic phase was then dried (Na2SO4). The solvent was removed in vacuo. Column chromatography ($SiO_2$: Hexanes/$CH_2Cl_2$=3:1) afforded the product S3 as a white solid (0.180 g, 94%). 1H NMR (500 MHz, $CDCl_3$): δ=7.97 (d, 2H, Ar—H$^a$, $^3J$=8.7 Hz), 7.54 (d, 2H, Ar—H$^b$, $^3J$=8.7 Hz), 3.92 (s, 3H, $OCH_3$), 3.23 (s, 1H, C☐CH). $^{13}$C NMR ($CDCl_3$, 125 MHz): δ=166.3, 131.9, 130.0, 129.3, 126.6, 82.7, 79.9, 52.1. HiRes MS (ESI-TOF): Calcd. for [M+H]$^+$ $C_{10}H_9O_2^+$=161.0597; found m/z=161.0590. (see, e.g., FIG. 8).

Figure 9:
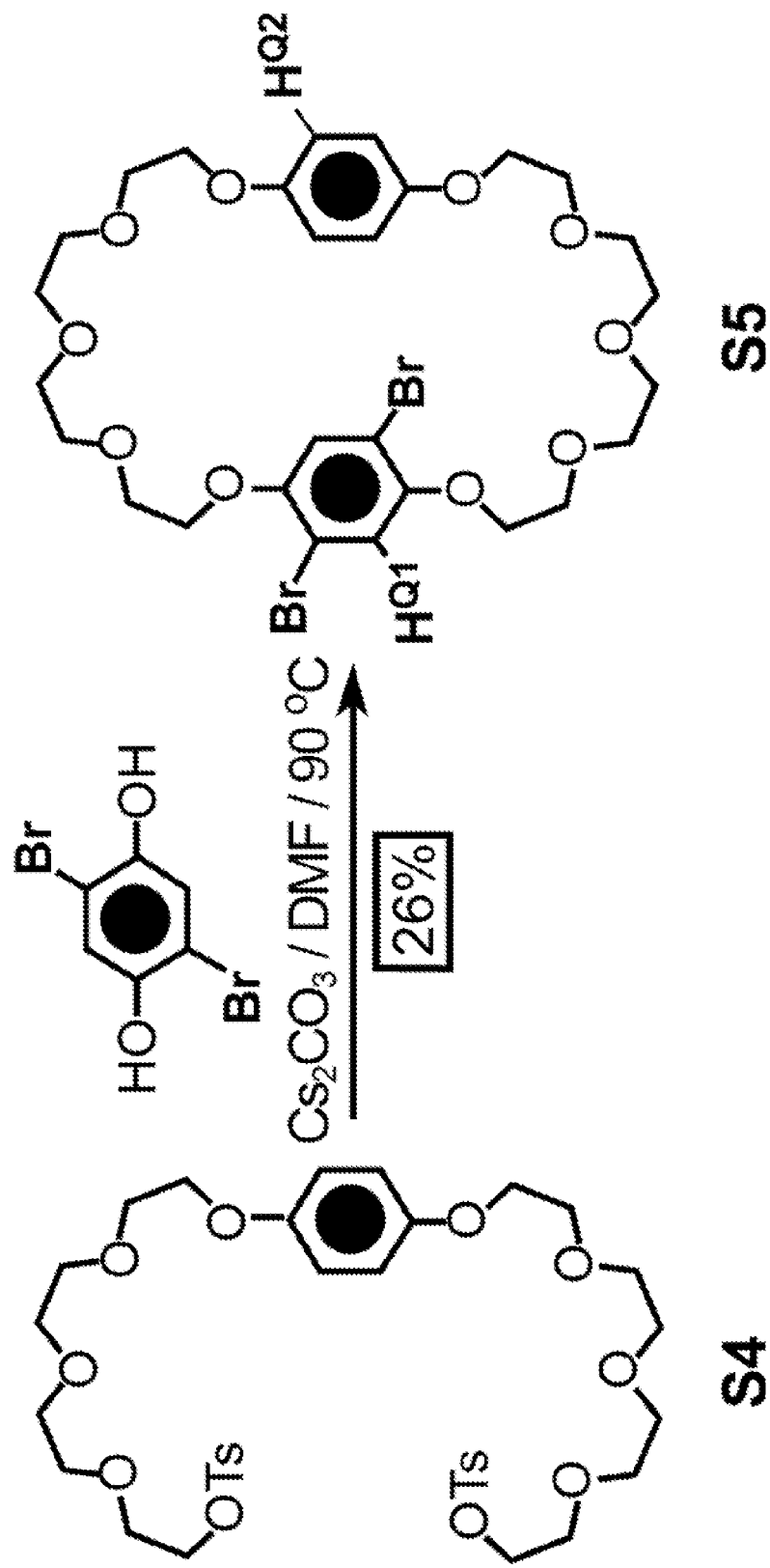
FIG. 9. Shows a step in the synthesis of strut 2 comprising a macrocycle.

S5: In a flame-dried, 3-neck, round bottom flask, S4 (2) (2.80 g, 3.62 mmol) and 2,5-dibromohydroquinone (0.973 g, 3.63 mmol) were dissolved in DMF (180 mL). $Cs_2CO_3$ (2.37 g, 7.26 mmol) was added to the solution. The mixture was stirred under Ar at 90° C. for 3 days. The solvent was then removed in vacuo. The residue was \dissolved in $CH_2Cl_2$ (100 mL) before being washed with brine (50 mL×3). The organic phase was dried ($Na_2SO_4$) and the solvent was then removed in vacuo. Column chromatography ($SiO_2$: Et2O/$CH_2Cl_2$=2:1) provided the product S5 as a white solid (0.650 g, 26%). $^1$H NMR (500 MHz, $CDCl_3$): δ=7.07 (s, 2H, Ar—HQ1), 6.74 (s, 4H, Ar—HQ2), 4.05-3.68 (m, 32H, $OCH_2O$). $^{13}$C NMR ($CDCl_3$, 125 MHz): δ=153.1, 150.3, 119.1, 115.6, 111.4, 71.1, 71.0, 70.9, 70.9, 70.8, 70.3, 69.8, 69.6, 68.2. HiRes MS (ESI-TOF): Calcd. for [M+H]$^+$ $C_{28}H_{39}Br_2O_{10}^+$ m/z=693.0904; found m/z=693.0902. (see, e.g., FIG. 9).

Figure 10:
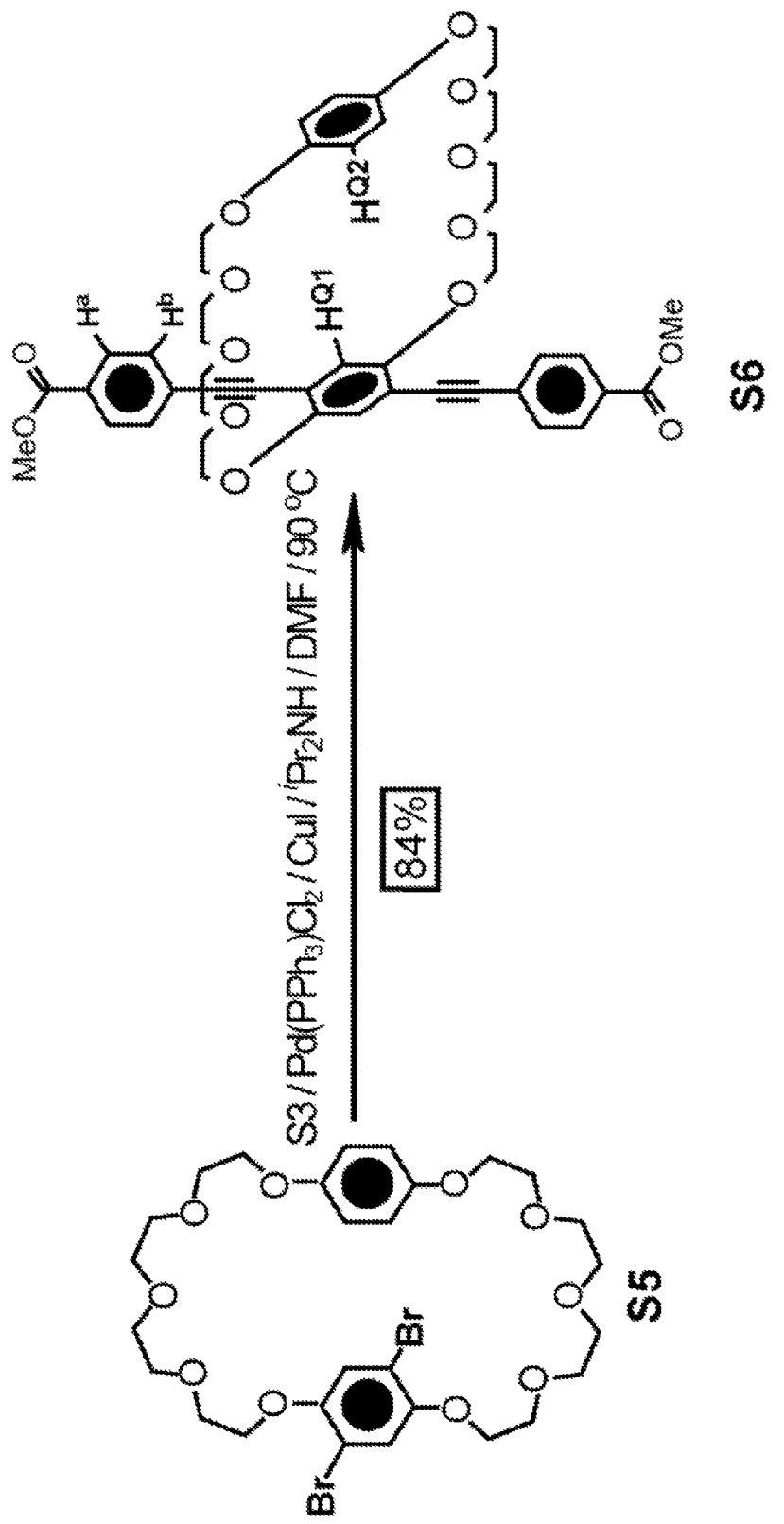
FIG. 10. Shows a scheme for the synthesis of a strut useful in a BORG of the disclosure.

S6: S5 (0.100 g, 0.144 mmol) and S3 (0.0510 g, 0.317 mmol) were dissolved in a mixture of DMF (3 mL) and iPr2NH (1 mL). Under Ar protection, $Pd(PPh_3)_2Cl_2$ (0.010 g, 0.014 mmol) and CuI (0.003 g, 0.014 mmol) were added to the solution. The mixture was stirred under Ar at 90° C. for 48 h before the solvent was removed in vacuo. The residue was then dissolved in $CH_2Cl_2$ (5 mL) before being washed with $H_2O$ (3 mL×2) and brine (3 mL). The organic phase was dried ($Na_2SO_4$) and the solvent was then removed in vacuo. Column chromatography ($SiO_2$: Et$_2$O/CH$_2$Cl2=2:1) provided product S6 as a yellow fluorescent solid (0.101 g, 84.0%). $^1$H NMR (500 MHz, CDCl3): δ=8.02 (d, 4H, Ar—H$^a$, $^3J$=8.2 Hz), 7.60 (d, 4H, Ar—H$^b$, $^3J$=8.2 Hz), 7.00 (s, 2H, Ar—HQ1), 6.68 (s, 4H, Ar—HQ2), 4.13-3.64 (m, 32H, $OCH_2O$), 3.94 (s, 3H, $OCH_3$). $^{13}$C NMR (CDCl3, 125 MHz): δ=166.4, 153.7, 152.9, 131.4, 129.4, 129.4, 127.9, 117.0, 115.3, 94.5, 88.7, 71.0, 70.9, 70.7, 70.6, 69.6, 69.6, 69.5, 68.0, 52.1. HiRes MS (ESI-TOF): Calcd. for [M+H]$^+$ C$_{48}$H$_{53}$O$_{14}$+ m/z=853.3430; found m/z=853.3433. (see, e.g., FIG. 10).

Figure 11:
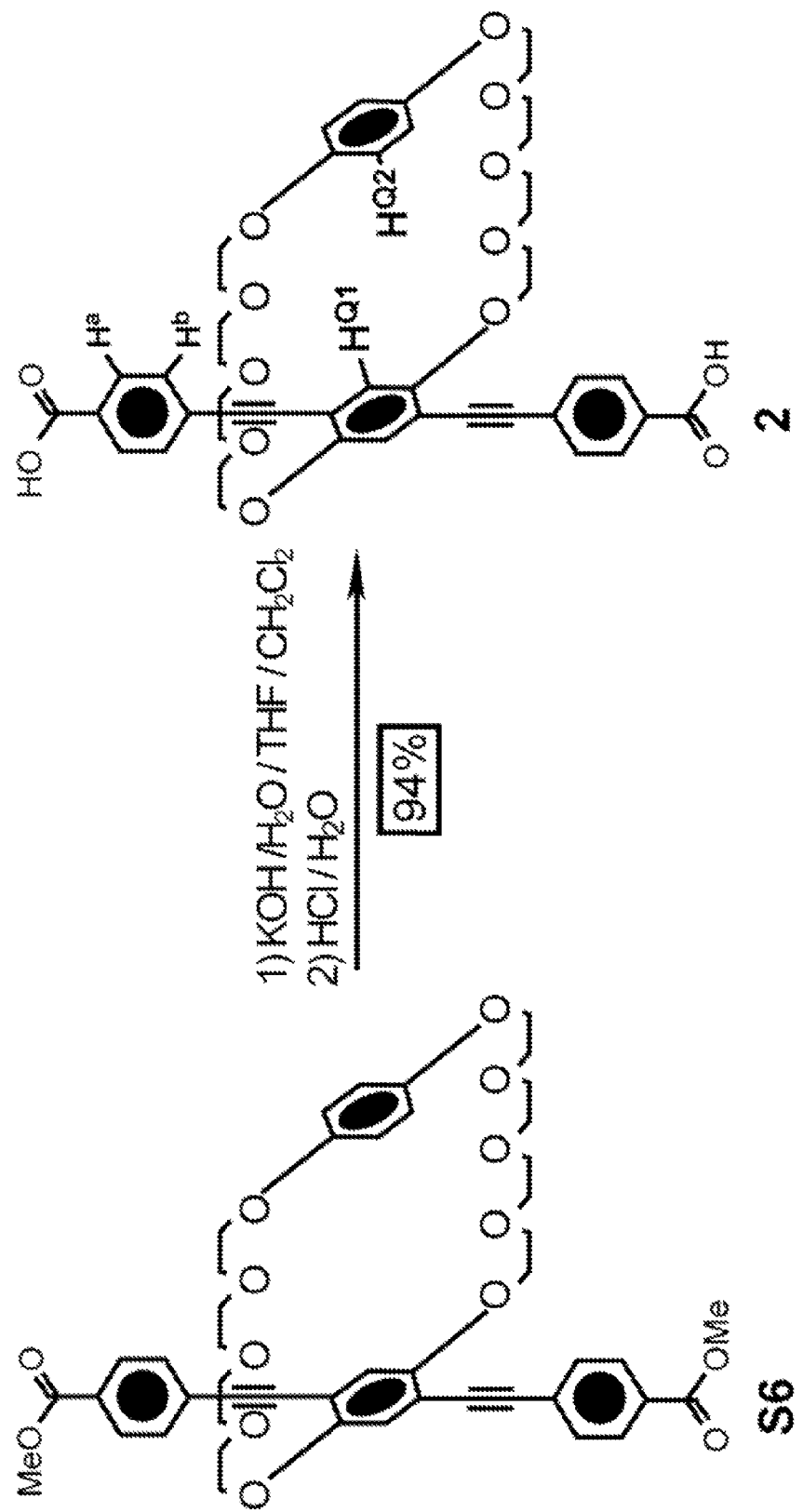
FIG. 11. Shows a scheme for the synthesis of struts 2 of a BORG of the disclosure.

2: S6 (200 mg, 0.235 mmol) and KOH (52.6 mg, 0.939 mmol) were dissolved in a mixture of MeOH (10 mL), CH$_2$Cl$_2$ (10 mL), and THF (10 mL). The following reaction and purification procedures are identical with those for 1. Product 2 is a yellow solid (181 mg, 94%). 1H NMR (500 MHz, CDCl3): δ=13.24 (b, 2H, COOH), 8.04 (d, 4H, Ar—H$^a$, $^3$J=8.3 Hz), 7.58 (d, 4H, Ar—H$^b$, $^3$J=8.3 Hz), 6.99 (s, 2H, Ar—HQ1), 6.67 (s, 4H, Ar—HQ2), 4.13-3.63 (m, 32H, OCH2O). $^{13}$C NMR (CDCl$_3$, 125 MHz): δ=170.2, 153.9, 153.0, 131.6, 130.1, 128.8, 128.7, 117.2, 115.5, 94.6, 89.2, 71.1, 71.0, 70.8, 70.7, 69.8, 69.7, 69.6, 68.1. HiRes MS (ESI-TOF): Calcd. for [M+H]$^+$ C$_{46}$H$_{49}$O$_{14}$$^+$ m/z=825.3117; found m/z=825.3115. (see, e.g., FIG. 11).

Figure 12:
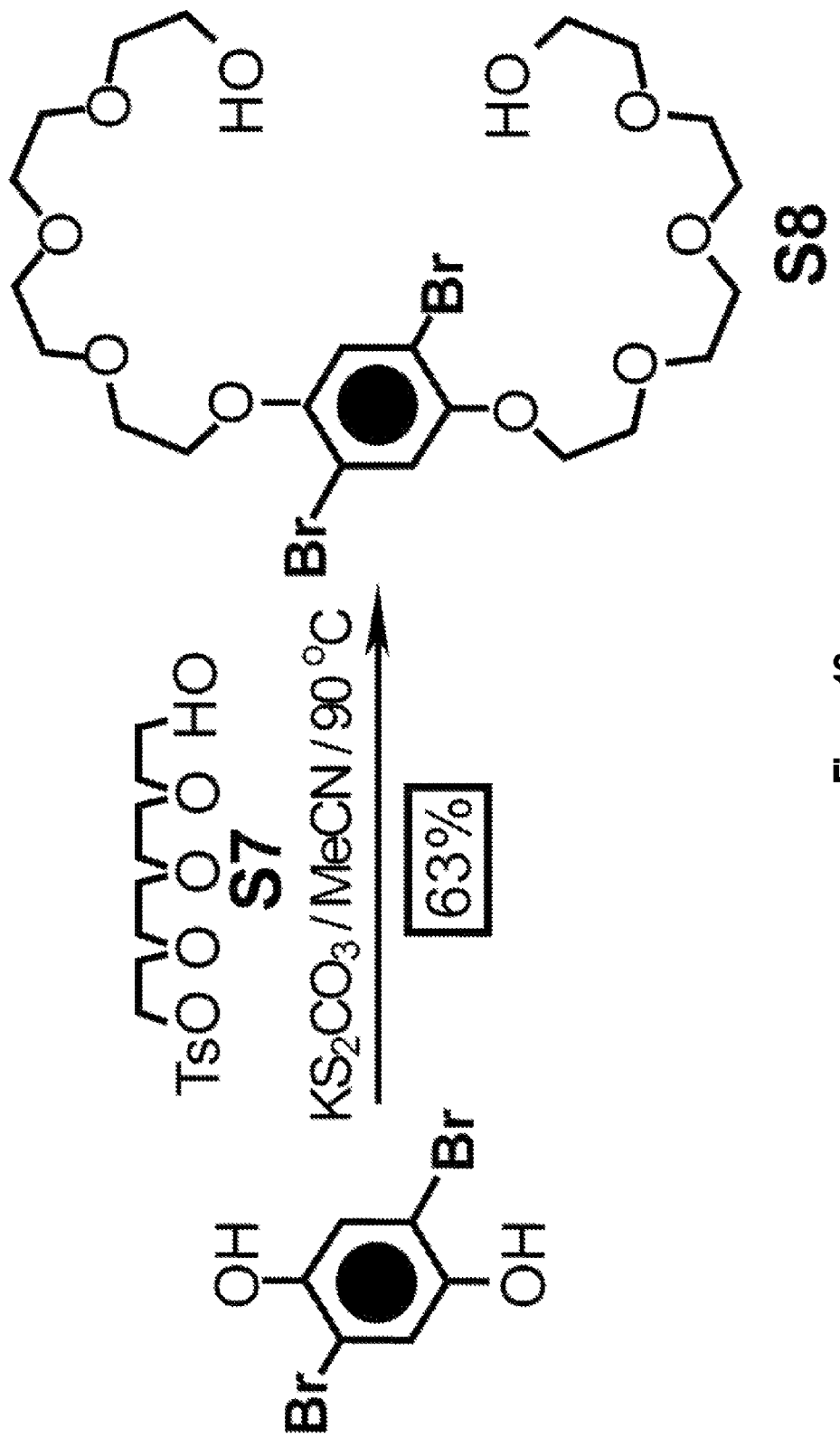
FIG. 12. Shows a scheme for the synthesis of macromolecule S8.

S8: A solution of 2,5-dibromohydroquinone (9.38 g, 35.0 mmol) and K$_2$CO$_3$ (19.34 g, 140 mmol) in MeCN (400 mL) was heated under reflux in an inert atmosphere for 30 min. A solution of S7 (26.9 g, 77.0 mmol) in MeCN (40 mL) was added to the mixture dropwise over 30 min. Stirring and heating were continued for 3 days. The reaction mixture was then filtered and solvent was removed in vacuo. The residue was purified by column chromatography (SiO$_2$: MeOH/CH$_2$Cl$_2$=1:9) to yield compound S8 as a white solid (13.7 g, 63%). $^1$H NMR (500 MHz, CDCl$_3$): δ=7.14 (s, 2H, Ar—H), 4.13-3.57 (m, 32H, OCH$_2$O), 2.72 (b, 2H, OH). $^{13}$C NMR (CDCl$_3$, 125 MHz): δ=150.4, 119.3, 111.6, 72.7, 71.3, 70.8, 70.8, 70.5, 70.3, 69.8, 61.9. HiRes MS (ESI-TOF): Calcd. for [M+H]$^+$ C$_{22}$H$_{37}$Br$_2$O$_{10}$$^+$ m/z=619.0748; found m/z=619.0753. (see, e.g., FIG. 12).

Figure 13:
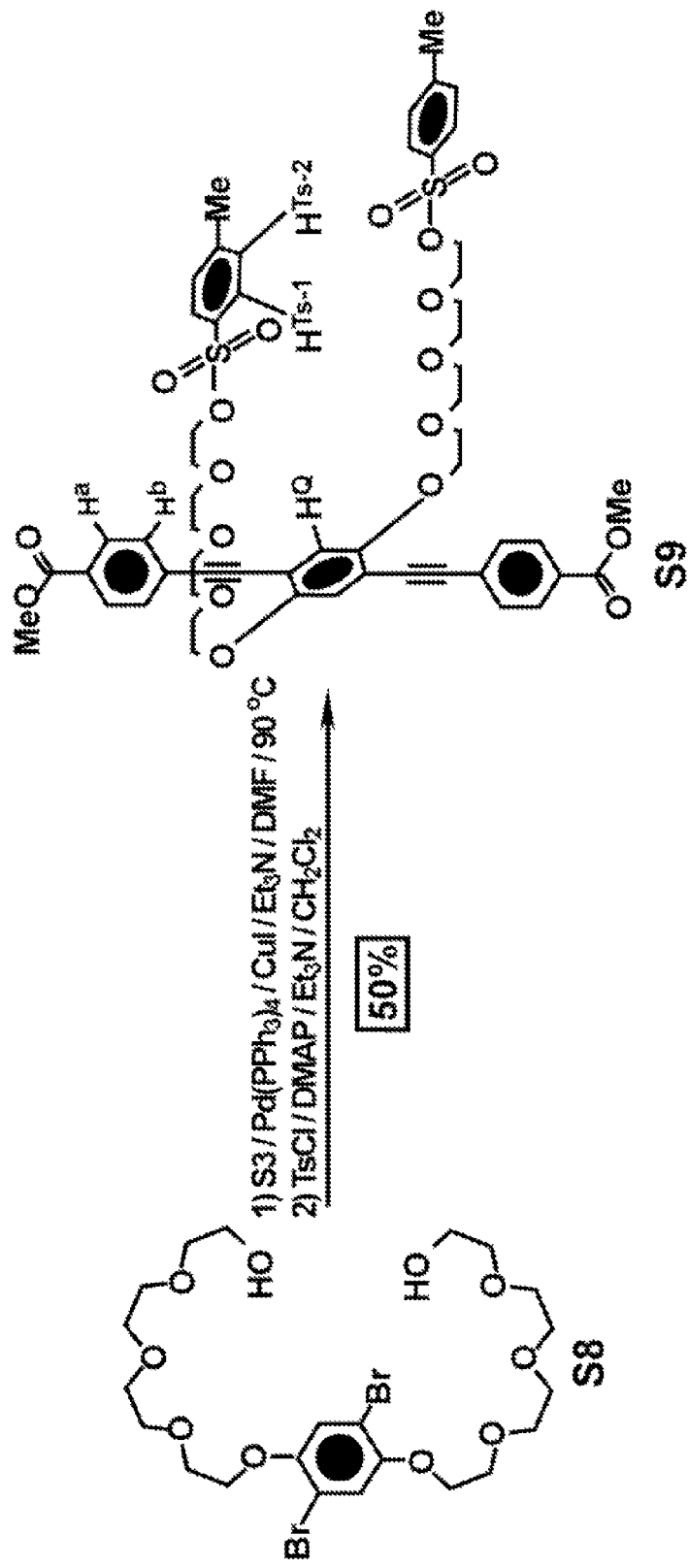
FIG. 13. Shows a scheme for the synthesis of a strut linked to S8.

S9: S8 (3.10 g, 5.00 mmol), S3 (1.76 g, 11.0 mmol), Pd(PPh$_3$)$_4$ (289 mg, 0.250 mmol), and CuI (47.5 mg, 0.25 mmol) were added to Et3N (50 mL) and DMF (50 mL). The mixture was stirred at 80° C. for three days before solvents were removed in vacuo. The residue was then dissolved in CH$_2$Cl$_2$ (50 mL), Et$_3$N (7.0 mL, 50 mmol), and 4-dimethylaminopyridine (122 mg, 1.0 mmol), and a solution of p-toluenesylfonyl chloride (2.29 g, 12.0 mmol) in CH$_2$Cl$_2$ (5 mL) was added. The solution was stirred for 3 h, washed with 1M HCl (100 mL) and H$_2$O (100 mL×2), and then dried (MgSO4). The solvent was then removed in vacuo and the residue was purified by column chromatography (SiO$_2$: EtOAc/CH$_2$Cl$_2$=1:2) to yield S9 as a yellow solid (2.72 g, 50%). NMR (500 MHz, CDCl3): δ=8.02 (d, 4H, Ar—H$^a$, $^3$J=8.4 Hz), 7.78 (d, 4H, Ar—H$^{Ts-1}$, $^3$J=8.2 Hz), 7.58 (d, 4H, Ar—H$^b$, $^3$J=8.3 Hz), 7.31 (d, 4H, Ar—HTs-2, 3J=8.2 Hz), 7.06 (s, 2H, Ar—H$^Q$), 4.22-3.56 (m, 32H, OCH$_2$O), 3.93 (s, 6H, COOCH$_3$), 2.42 (s, 6H, Ts-CH$_3$). $^{13}$C NMR (CDCl3, 125 MHz): δ=165.5, 152.7, 143.8, 131.9, 130.4, 128.8, 128.6, 128.5, 126.9, 126.9, 116.2, 113.0, 93.5, 87.7, 70.1, 69.7, 69.7, 69.5, 68.7, 68.5, 68.2, 67.6, 51.3, 20.6. HiRes MS (ESI-TOF): Calcd. for [M+H]$^+$ C$_{56}$H$_{63}$O$_{18}$S$_2$$^+$ m/z=1087.3450; found m/z=1087.3477. (see, e.g., FIG. 13).

Synthesis of BPP34C10DME S10: A solution of S8 (1.09 g, 1.0 mmol), hydroquinone (110 mg, 1.0 mmol), and Cs2CO$_3$ (1.3 g, 4.0 mmol) in DMF (100 mL) was stirred and refluxed under inert atmosphere for 5 days. The reaction mixture was filtered and the solvent was removed. The residue was purified by column chromatography (SiO$_2$:Et$_2$O/CH$_2$Cl$_2$=1:1) to yield S10 as a yellow solid (200 mg, 24%). (see, e.g., FIG. 14).

Figure 15:
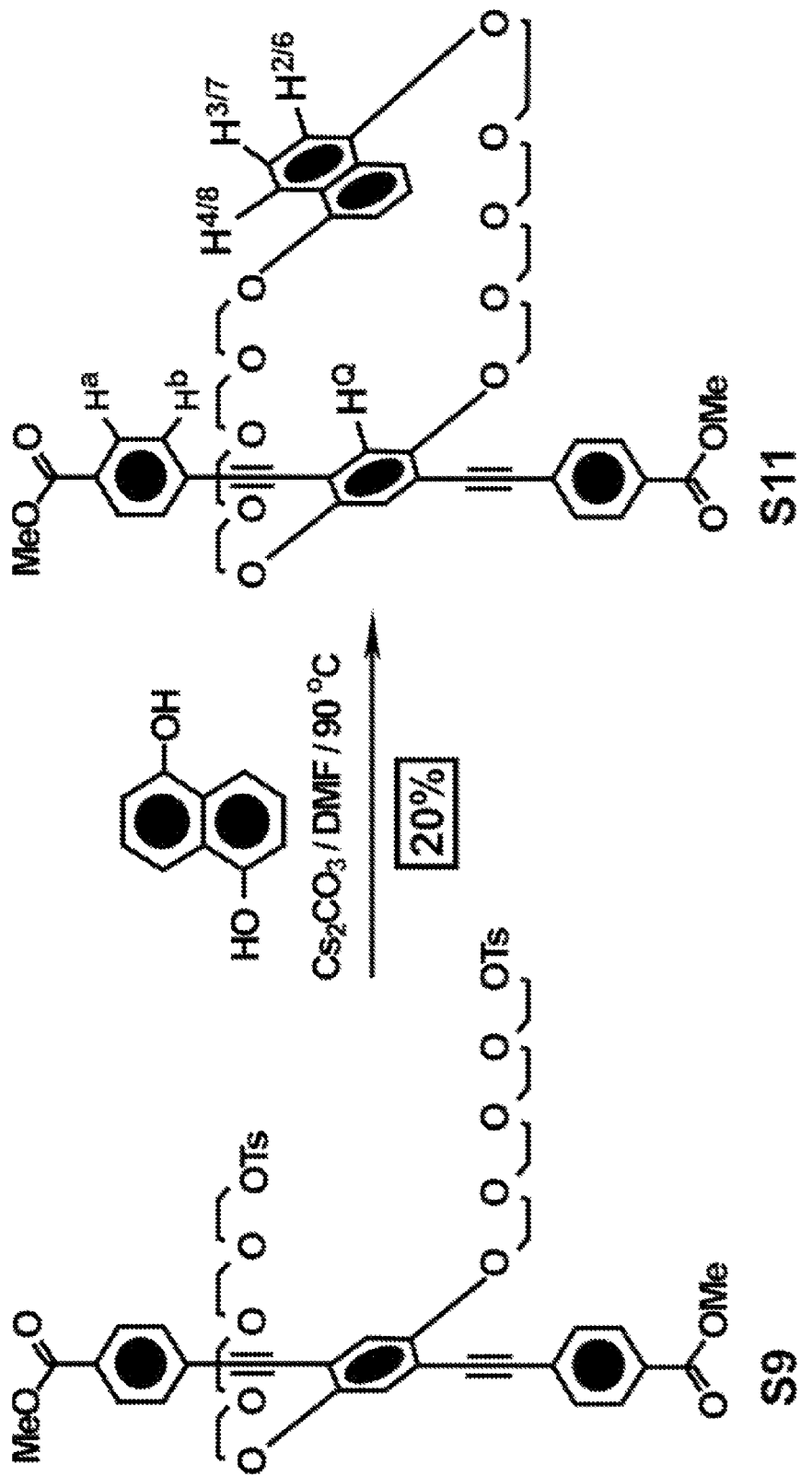
FIG. 15. Shows a scheme for the synthesis of structure S11.

S11: A solution of S9 (820 mg, 0.755 mmol), 1,5-dihydroxynaphthalene (121 mg, 0.755 mmol), and Cs$_2$CO$_3$ (984 mg, 3.02 mmol) were dissolved in DMF (80 mL). The solution was heated under reflux and stirred in an inert atmosphere for 3 days. The reaction mixture was filtered and the solvent was removed. The residue was purified by column chromatography (SiO$_2$: Et$_2$O/CH$_2$Cl$_2$=1:1) to yield S11 as a bright yellow solid (136 mg, 20%). $^1$H NMR (500 MHz, CDCl$_3$): δ=8.01 (d, 4H, Ar—H$^a$, $^3$J=8.4 Hz), 7.78 (d, 2H, Ar—H$^{4/8}$, $^3$J=8.4 Hz), 7.57 (d, 4H, Ar—H$^b$, $^3$J=8.4 Hz), 7.23 (t, 2H, Ar—H$^{3/7}$, $^3$J=8.4 Hz), 6.84 (s, 2H, Ar—H$^Q$), 6.66 (d, 2H, Ar—H$^{2/6}$, $^3$J=8.4 Hz), 4.18-3.69 (m, 32H, OCH$_2$O), 3.94 (s, 6H, CH$_3$). $^{13}$C NMR (CDCl3, 125 MHz): δ=166.6, 154.2, 153.5, 131.5, 129.5, 129.4, 128.0, 126.6, 125.0, 116.6, 114.5, 113.7, 105.5, 94.4, 88.9, 71.0, 71.0, 70.9, 70.8, 69.7, 69.6, 68.2, 67.8, 52.3. HiRes MS (ESI-TOF): Calcd. for [M+H]$^+$ C$_{52}$H$_{55}$O$_{14}$$^+$=903.3586; found m/z=903.3604. (see, e.g., FIG. 15).

Figure 16:
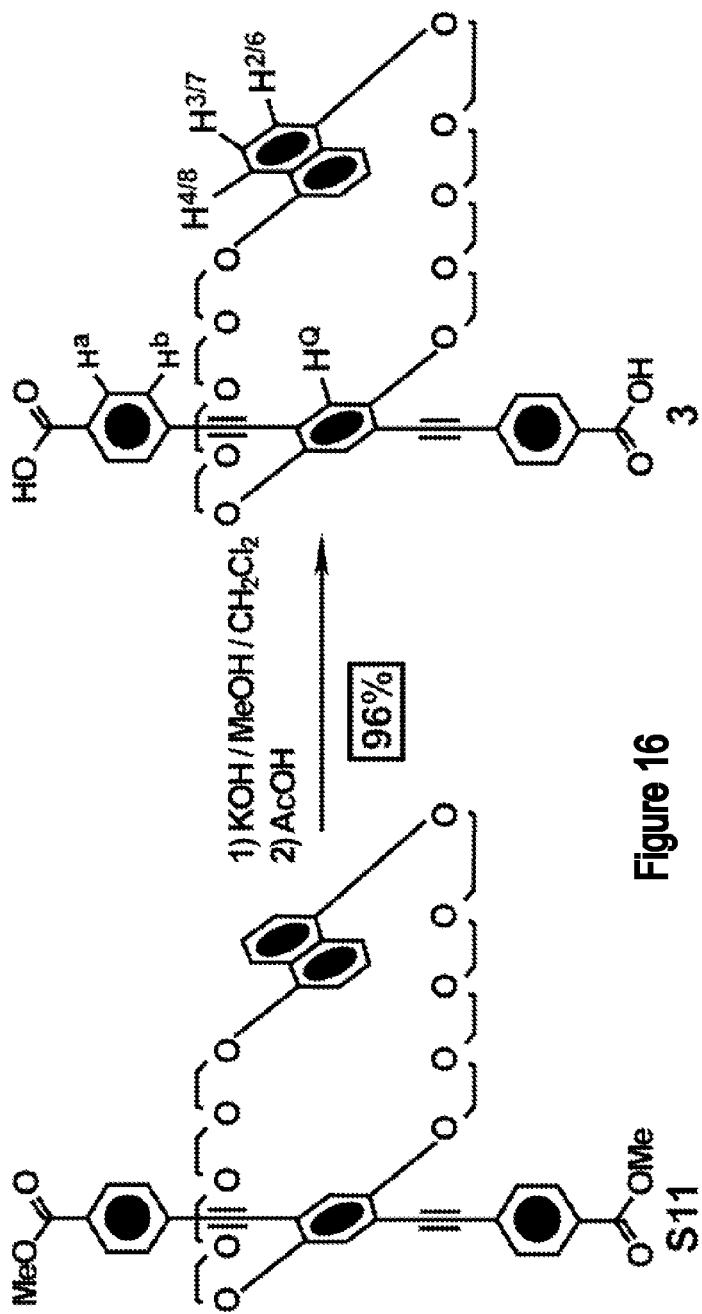
FIG. 16. Shows a scheme for the synthesis of strut 3 useful in a BORG framework of the disclosure.

3: S11 (130 mg, 0.144 mmol) and KOH (80 mg, 1.4 mmol) were dissolved in a mixture of MeOH (2.5 mL) and CH$_2$Cl$_2$ (2.5 mL). The solution was stirred overnight. The reaction mixture was then filtered and the solvent was removed. The residue was purified by column chromatography (SiO$_2$: CH$_2$Cl$_2$/MeOH/AcOH=9:1:0.01) to yield strut 3 as a bright yellow solid (121 mg, 96%). $^1$H NMR (500 MHz, CD$_3$SOCD$_3$): δ=12.8 (b, 2H, COOH), 7.94 (d, 4H, Ar—H$^a$, $^3$J=8.4 Hz), 7.61 (d, 2H, Ar—H$^{418}$, $^3$J=8.3 Hz), 7.60 (d, 4H, Ar—H$^b$, $^3$J=8.4 Hz), 7.22 (t, 2H, Ar—H$^{3/7}$, $^3$J=8.3 Hz), 7.09 (s, 2H, Ar—H$^Q$), 6.72 (d, 2H, Ar—H$^{2/6}$, $^3$J=8.3 Hz), 4.10-3.53 (m, 32H, OCH$_2$O). $^{13}$C NMR (CD3SOCD3, 125 MHz): δ=172.3, 154.1, 153.5, 131.7, 130.9, 129.9, 127.2, 126.3, 125.5, 116.8, 114.1, 113.4, 106.1, 94.7, 89.2, 70.6, 70.5, 70.4, 70.3, 69.3, 69.3, 69.2, 68.1. HiRes MS (ESI-TOF): Calcd. for [M+H]$^+$ C$_{50}$H$_{51}$O$_{14}$$^+$ m/z=875.3273; found m/z=875.3250. (see, FIG. 16).

Figure 17:
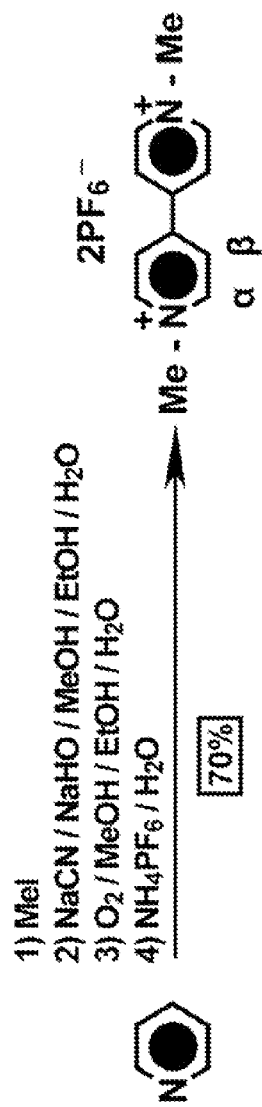
FIG. 17. Shows a scheme for the synthesis of $^{15}$N-labeled PQT-2PF$_6$.
Figure 18:
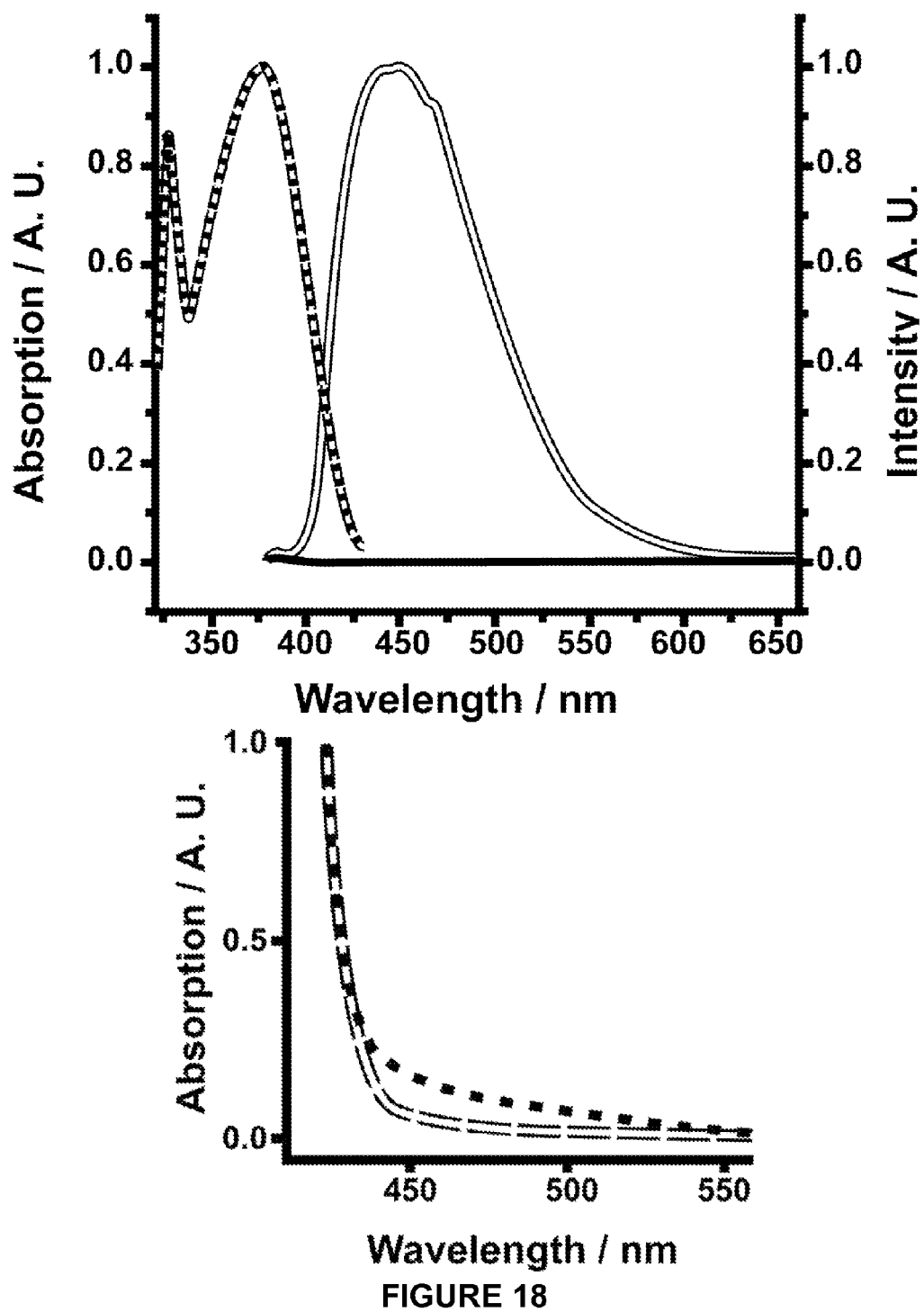
FIG. 18. UV/vis (dashed lines) and emission (solid lines) spectra of strut 2 (20.0 μM, orange) and the pseudorotaxane [PQT ⊂ 2].2PF$_6$ (20.0 μM, orange) in Me$_2$CO at room temperature, absorption $\lambda_{max}$=377 nm. Insert: UV/vis spectra of strut 2 (0.500 mM, orange) and the pseudorotaxane [PQT ⊂ 2].2PF$_6$ (0.500 mM, orange). The charge-transfer absorption (λ=430-450 nm) of [PQT ⊂ 2].2PF$_6$ overlaps with the emission (λ=458 nm) of strut 2. The fluorescence is thus quenched upon formation of the pseudorotaxane.

$^{15}$N-Labeled PQT.2PF6: Under inert atmosphere, CH$_3$I (4.67 g, 32.9 mmol) was added dropwise to $^{15}$N-labeled C$_6$H$_5$N (2.00 g, 25.3 mmol). The mixture was stirred at 50° C. for 12 h before MeOH (0.5 mL) was added. The mixture was stirred for another 10 min before the solvents were removed in vacuo. The resulting white solid was dissolved in a mixture of EtOH (8 mL), MeOH (8 mL) and H$_2$O (8 mL) together with NaCN (3.05 g, 63.2 mmol) and NaOH (1.21 g, 30.3 mmol). The solution was heated under reflux for 30 min. A dark blue solution resulted. After the solution had cooled to room temperature, ZnSO$_4$.7H$_2$O (10.2 g, 35.4 mmol) was added. A precipitate started to form. The mixture was kept at room temperature without stirring for 1 h before the precipitate was removed by filtration. The pH of the filtrate was then adjusted to 5 with H$_2$SO$_4$. O$_2$ was then bubbled into the solution for 12 h while the temperature of the solution was controlled under 50° C. The color of the solution turned from violet to tan. A saturated aqueous solution of NH$_4$PF$_6$ was then added until no more precipitate formed. The precipitate was collected by filtration, washed with H2O, EtOH and Et$_2$O, and then dried in air. The product (3.90 g, 70%) is a white solid. $^1$H NMR (500 MHz, CD3COCD3): δ=9.39 (d, 4H, α-H, $^3$J=6.5 Hz), 8.86 (d, 4H, β-H, $^3$J=6.5 Hz), 4.76 (s, 6H, CH$_3$). $^{13}$C NMR (CD3COCD3, 125 MHz): δ=151.5, 146.5, 126.7, 52.2. HiRes MS (ESI-TOF): Calcd. for [M.PF6]$^+$ C$_{12}$H$_{14}$F$_6$N$_2$P$^+$ m/z=331.079; found m/z=331.082. (see, e.g., FIG. 17).

[PQT⊂2].2PF$_6$ single crystal: Strut 2 (9.01 mg) and PQT.2PF$_6$ (3.54 mg) were dissolved in Me$_2$CO (5 mL) in a 20-mL vial. n-Pentane was added to the solution until some precipitate was observed. The mixture was filtered to obtain a saturated solution. The solution was left at room temperature for 3 days. Red block-shaped crystals were observed on the wall of the vial.

MOF-1000: A solid mixture of strut 1 (17.00 mg, 3.99× 10$^{-5}$ mol) and Zn(NO$_3$)$_2$.4H$_2$O (12.00 mg, 4.59×10$^{-5}$ mol) was dissolved in N,N-diethylformamide (DEF, BASF Corporation) (1 mL) in a 4-mL vial. The vial was capped and placed in an isothermal oven at 85° C. for 48 h. The vial was then removed from the oven and allowed to cool to room temperature naturally. Colorless block crystals were collected and rinsed with fresh DEF (4×1 mL). Elemental Analysis (evacuated): $Zn_4O(C_{26}H_{16}O_6)_3$: Calcd.: C, 60.41%; H, 3.12%. Found: C, 59.39%; H, 3.43%.

BORG-1: Methylamine solution (40 wt. % in $H_2O$, Aldrich Chemical Co.) (50 μL) was mixed with N,N-dimethylformamide (DMF, Fisher Scientific International Inc) (2 mL) as stock solution A. A solid mixture of strut 2 (3.60 mg, 4.36×$10^{-6}$ mol) and $Zn(NO_3)_2 \cdot 4H_2O$ (5.25 mg, 2.01×$10^{-5}$ mol, EM Science) was dissolved in DMF (1.0 mL) in a 4-mL vial. Stock solution A (20 μL) was added to the vial. The vial was capped and placed in an isothermal oven at 65° C. for 24 h. The vial was then removed from the oven and allowed to cool to room temperature naturally. After removal of mother liquor from the mixture, fresh DMF was added to the vial. Light yellow cubic crystals of BORG-1 were collected and rinsed with DMF (4×1 mL). Elemental Analysis (evacuated): $Zn_4O(C_{46}H_{46}O_{14})_3$: Calcd.: C, 60.36%; H, 5.07%. Found: C, 59.49%; H, 5.07%. BORG-1A: A solid mixture of strut 2 (3.30 mg, 4.00×$10^{-6}$ mol) and $Zn(NO_3)_2 \cdot 4H_2O$ (5.25 mg, 2.01×$10^{-5}$ mol, EM Science) was dissolved in DMF (1.0 mL) in a 4-mL vial. Stock solution A (20 μL) was added to the vial. The vial was capped and placed in an isothermal oven at 65° C. for 24 h. The vial was then removed from the oven and allowed to cool to room temperature naturally. After removal of mother liquor from the mixture, fresh DMF was added to the vial. Occasionally, a mixture of light yellow cubic crystals and light yellow hexagonal crystals was collected. The hexagonal shaped crystals were picked and single crystal X-ray diffraction determined the structure of BORG-1A. (Adding less than 2 mg PQT.2PF6 could avoid the formation of BORG-1A under these conditions.)

BORG-2: A methylamine solution (40 wt. % in H2O) (50 μL) was mixed with 2 mL DMF as stock solution A. A solid mixture of strut 3 (3.82 mg, 4.36×$10^{-6}$ mol) and $Zn(NO_3)_2 \cdot 4H_2O$ (5.25 mg, 2.01×$10^{-5}$ mol) was dissolved in DMF (1.0 mL) in a 4-mL vial. Stock solution A (20 μL) was added to the vial. The vial was capped and placed in an isothermal oven at 65° C. for 24 h. The vial was then removed from the oven and allowed to cool to room temperature naturally. After removal of mother liquor from the mixture, fresh DMF was added to the vial. Light yellow cubic crystals of BORG-2 were collected and rinsed with DMF (4×1 mL). Elemental Analysis (evacuated): $Zn_4O(C_{50}H_{48}O_{14})_3$: Calcd.: C, 62.20%; H, 5.01%. Found: C, 63.21%; H, 4.98%. BORG-1 Pseudorotaxanes: BORG-1 crystalline solid (approximately 20 mg) in fresh. DMF was exchanged with fresh $Me_2CO$ (10 mL) for 3 days, three times every day, to remove unreacted starting material. After decanting the $Me_2CO$, saturated $PQT.2PF_6$ solution in $Me_2CO$ (5 mL) was added. The color of the crystals immediately turned red. After sitting for 6 h, the mixture was filtered and the red solids were flush-washed with $Me_2CO$ (10 mL). The solid was dried under vacuum ($10^{-2}$ Torr) for 24 h at room temperature. Elemental Analysis (evacuated): $Zn_4O(C_{46}H_{46}O_{14})_3(C_{12}H_{14}N_2P_2F_{12})_3$: Calcd.: C, 50.06%; H, 4.45%; N, 2.01%; F, 16.38%. Found: C, 49.46%; H, 4.50%; N, 1.83%; F, 14.46%.

Figure 3:
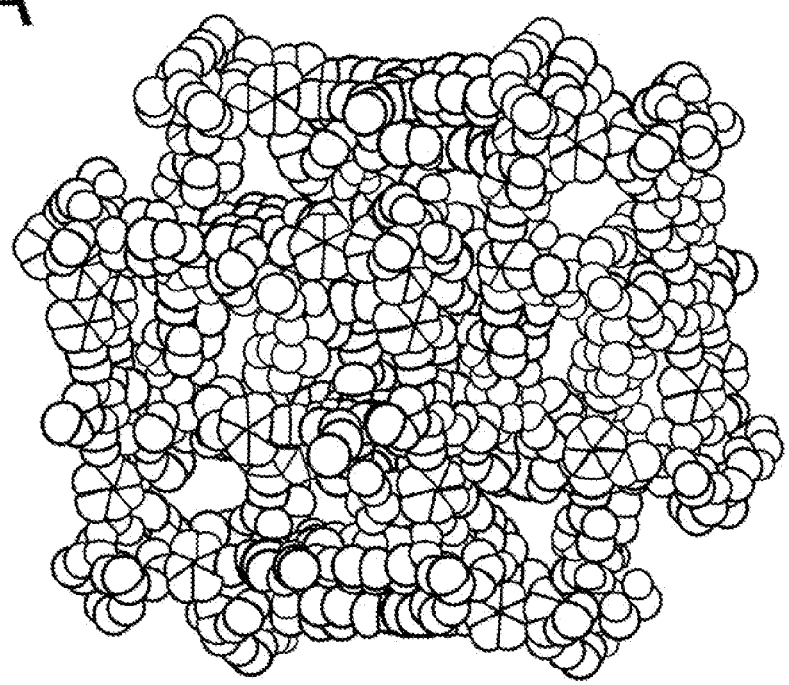
FIG. 3. Space filling illustration of MOF-1000 (A), BORG-1A (B), BORG-1 (C), and BORG-2 (D). The same color codes with FIG. 2 were applied.
Figure 3:
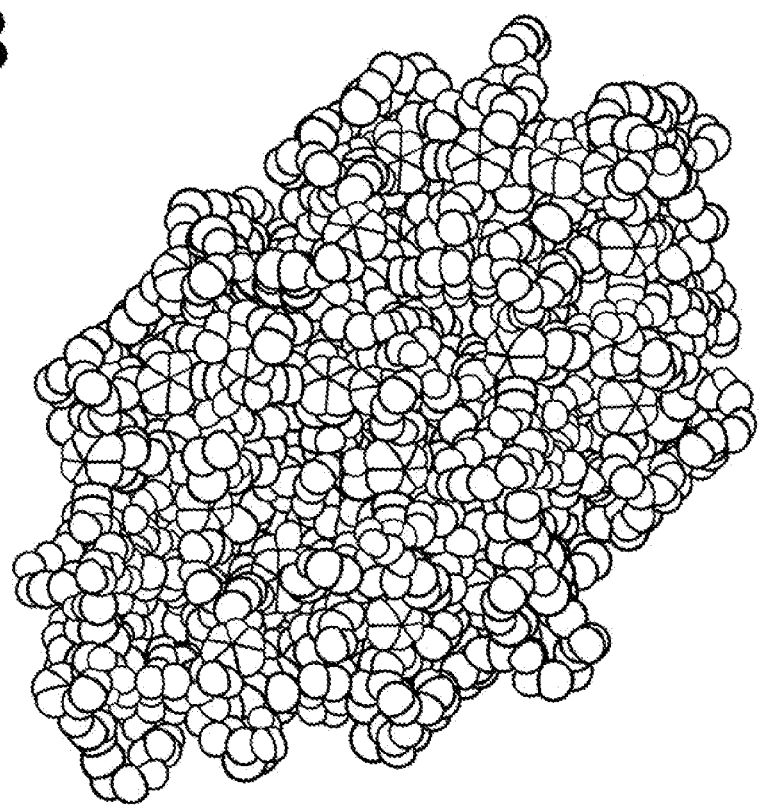
Figure 3:
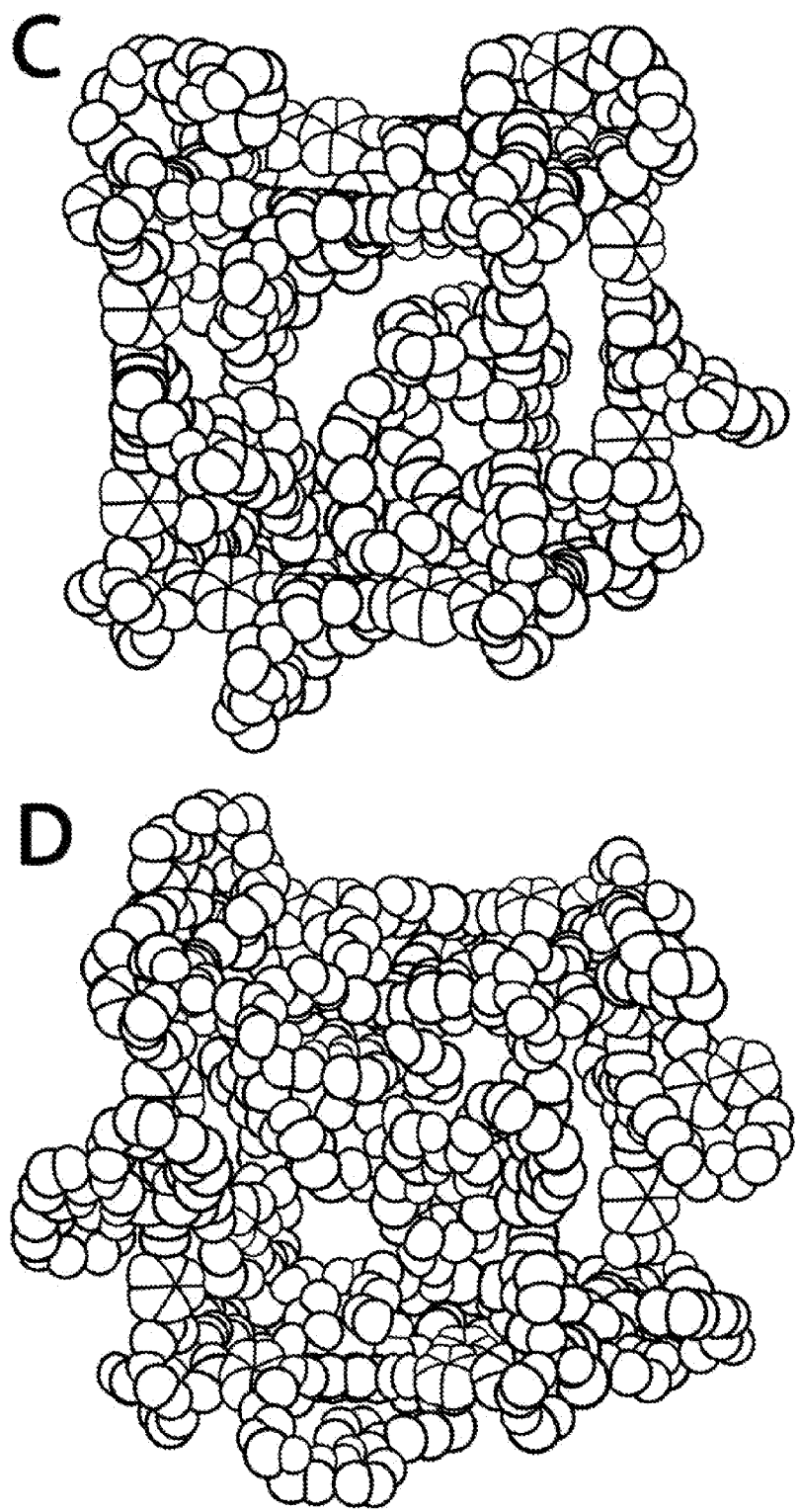

As described above, crystals of MOF-1000 (FIGS. 2A and 3A) were obtained by mixing a solution of strut 1, with $Zn(NO_3)_2 \cdot 4H_2O$, in diethylformamide (DEF) using conditions previously employed in the synthesis of MOF-5 (Eddaoudi et al., Science 295, 469 (2002); H. Li, M. Eddaoudi, M. O'Keeffe, O. M. Yaghi, Nature 402, 276 (1999)). Its crystal structure displays the same structural topology as does MOF-5. It is found to be four-fold interpenetrated because of the length and slender nature of the strut—the distance between the two carbon atoms from the carboxylate groups is 19.3 Å. Successful crystallization of MOF-1000, however, confirmed the practicality of creating BORGs using this synthetic protocol.

The struts 2 and 3, containing 34- and 36-membered polyether rings, which have been extensively used as receptors for the wide range of electron-deficient substrates, are ideally suited as molecular recognition modules for making BORGs. Strut 2 was prepared by means of a convergent synthetic approach (as described above), and used under similar conditions to those employed in the synthesis of MOF-1000 to give BORG-1A and BORG-1. The crystal structure of BORG-1A is a triply interpenetrating framework (FIGS. 2B and 3B), while that of BORG-1 is the corresponding non-interpenetrating form (FIGS. 2C and 3C); both have the MOF-5 type topology. The existence of BORG-1A, despite its occasional appearance as a minor product, validates indirectly the high porosity of BORG-1. The sheer openness of the structure, however, led to optimize the reaction conditions yet further in order to successfully obtain BORG-1 as a pure phase. BORG-1, which has an Fm-3m symmetry, with a unit cell parameter a=52.93 Å, is the largest non-interpenetrating isoreticular MOF (IRMOF) ever characterized by crystallography. Furthermore, this methodology was extended to the synthesis of BORG-2 (FIGS. 2D and 3D) by using the 1,5-dioxynaphthalene-containing strut 3, which was produced via a divergent synthetic route (as described above). Single crystal X-ray diffraction studies indicate that BORG-2 shares an identical cubic backbone with BORG-1, affirming the generality of such a methodology of building a variety of crystalline structures with such long struts capable of molecular recognition.

Calculations of the volumes of open space within the BORG structures confirm the highly open nature of these crystals (86.9% space unoccupied by BORG-1 framework atoms, based on a model using the program Cerius2, version 4.2). The inherent flexibility of the macrocyclic polyether substructure was evident from the single crystal X-ray analysis of BORG-1. The bismethylenedioxy units of the tetraethylene glycol loops in the substructure are found to be highly disordered. Nevertheless, the positions of all the atoms in the inorganic joints and the rigid backbone of the links are unambiguous as judged by comparison of the resulting bond distances and angles with the model structure. Based on the overall geometry and stoichiometry of the BORG framework, it was concluded that the crown ether receptors—capable of the complexation behavior required for molecular recognition—are integrated precisely and periodically inside a robust framework. Thus, the extended framework provides the basis for their strategic placement so that they are exposed to the maximum freedom of expression in three-dimensional space.

Figure 14:
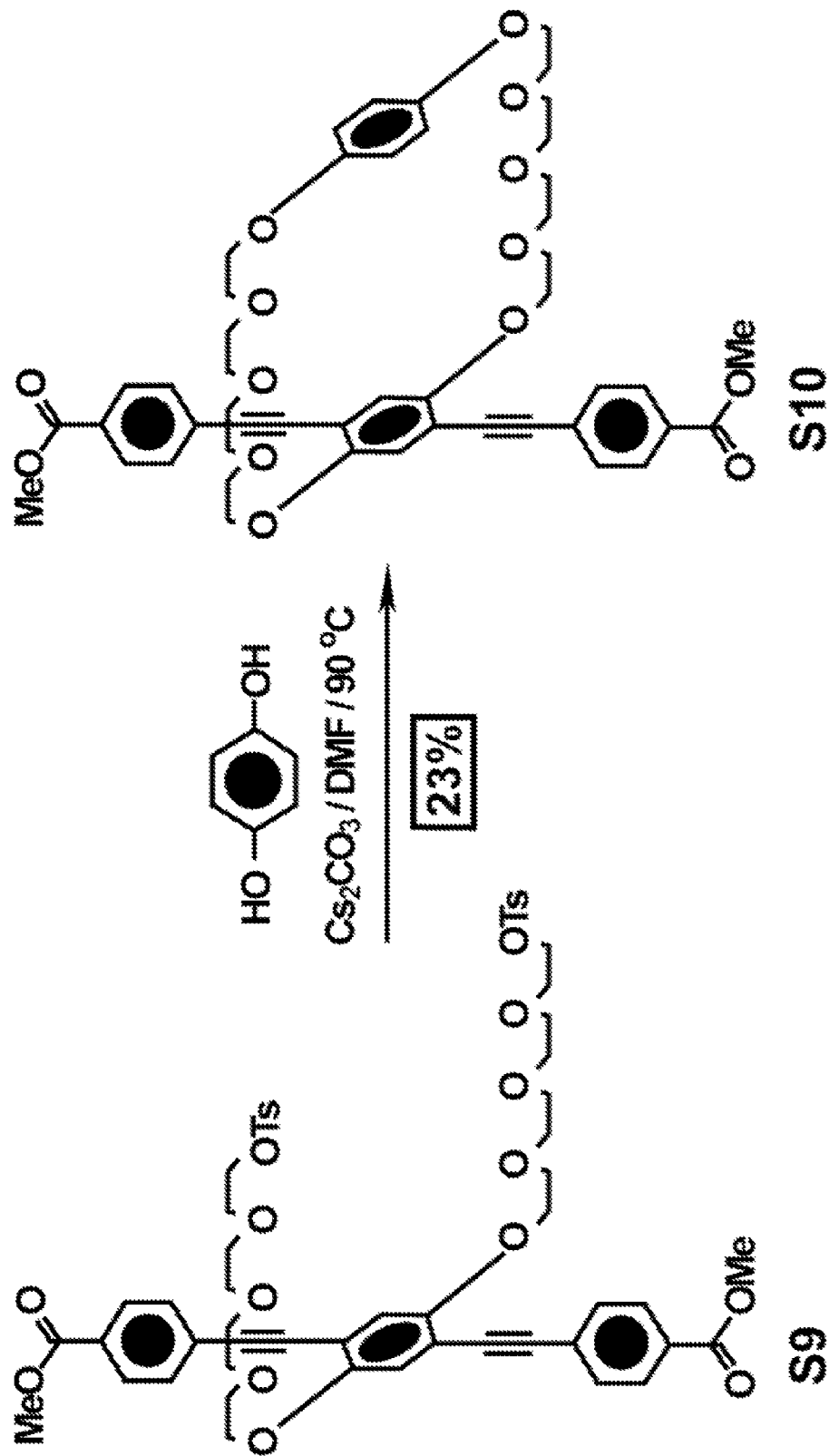
FIG. 14. Shows a scheme for the synthesis of BPP34C10DME useful as a strut in a BORG of the disclosure.

Further evidence of complexation was obtained by examining the 1H NMR spectrum of the digested BORG-1 pseudorotaxanes solid. Integration of the peaks appearing at 7.96 ppm (d, 4H, Ar—$H^\alpha$ in 2, see FIG. 4G) and 4.60 ppm (s, 6H, N—CH3 in $PQT^{2+}$) revealed the expected 1:1 ratio of strut 2 and the $PQT^{2+}$ dication, indicating that the docking phenomenon of the $PQT^{2+}$ dications does indeed take place at every crown ether ring throughout the whole BORG framework (FIG. 14). Solid-state 15N NMR spectroscopy, a technique which is highly sensitive to the environment of the nitrogen ($^{15}N$) in the $PQT^{2+}$ dication, provided further strong evidence for docking in BORG-1. Isotope-labeled $PQT^{2+}$ with 25% abundance of 15N was used to make the BORG-1 pseudorotaxanes and the solid was examined by 15N cross-polarization magic-angle spinning (CP/MAS) spectroscopy. The spectrum of the uncomplexed $PQT^{2+}$ dication has a $^{15}N$ signal centered on 207.2 ppm, while the spectrum of the PQT$^{2+}$ dication, bound within the crown ether rings in BORG-1, shows a significant upfield shift to 204.6 ppm for the 15N resonance resulting from docking into the macrocyclic polyether units of the struts (FIG. 4, D to F).

Figure 41:
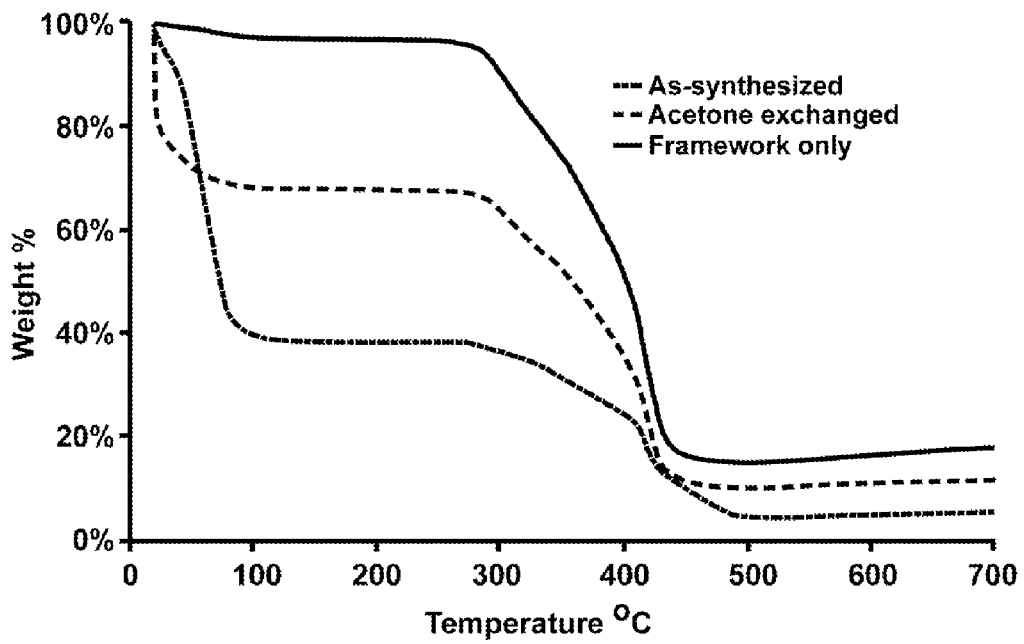
FIG. 41. Shows The overlay of TGA traces of BORG-2. As-synthesized, Me$_2$CO exchanged, framework only.
Figure 42:
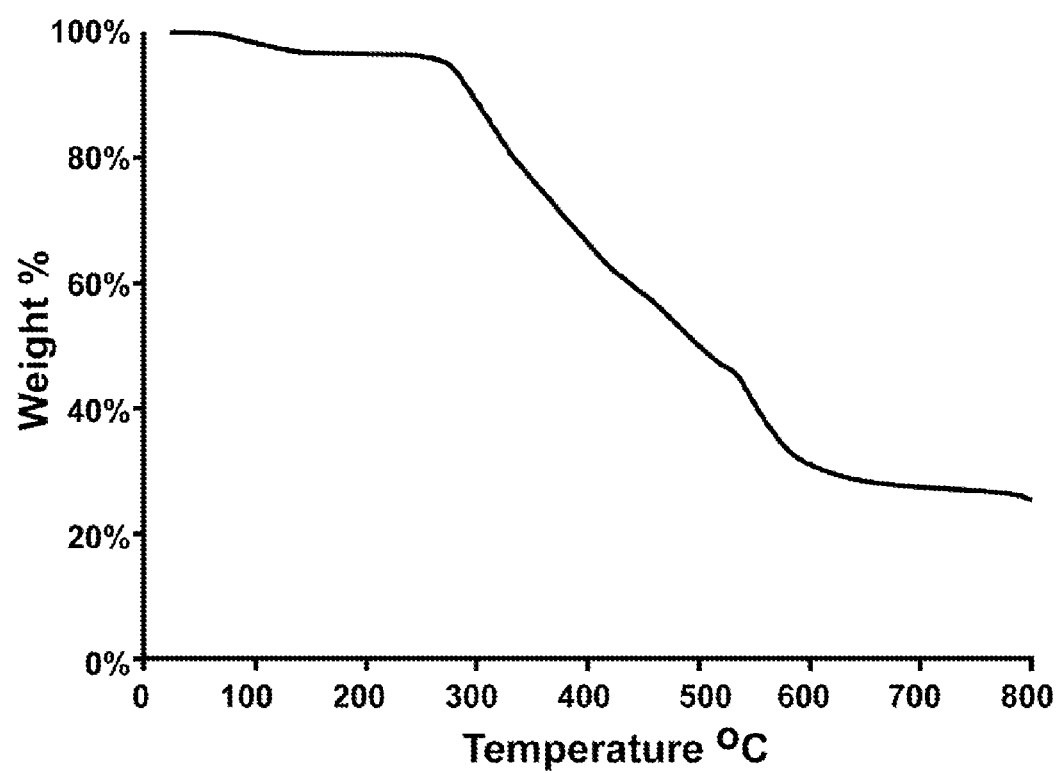
FIG. 42. Shows a TGA trace of BORG-1 pseudorotaxanes framework. The material is thermally stable to 300° C. Before the TGA experiment, the sample was evacuated at room temperature for 12 h after removing the sample from a saturated solution of paraquat in Me$_2$CO.

Similar studies carried out on strut 2 were used as a molecular model for comparison with BORG-1 complexation experiments. Here, addition of PQT.2PF$_6$ to a Me$_2$CO solution of strut 2 led to the formation of a pseudorotaxane [PQT ⊂ 2].2PF$_6$. The binding affinity (Ka=820 M) between the PQT$^{2+}$ dication and strut 2 in solution was obtained from spectrophotometric titrations. Single crystal X-ray diffraction of the [PQT ⊂ 2].2PF$_6$ (FIG. 41) clearly shows the insertion of the Π-electron deficient bipyridinium dication through the middle of the macrocyclic polyether. Π-Π Stacking aided and abetted by [C-$\neg$ H...O] interactions are reflected in the interplanar separation of 3.6 Å between the bipyridinium unit of PQT$^{2+}$ and the hydroquinone rings. The same upfield shift trend in the 15N NMR spectra observed for BORG-1 pseudorotaxanes was also evident in the 15N NMR spectra of [PQT ⊂ 2].2PF$_6$ in the solid state (FIG. 4H) as well as in solution. Control experiments were carried out by attempting to introduce PQT.2PF$_6$ into porous MOF-177 crystals, the pore dimensions of which were expected to allow the free movement of the PQT$^{2+}$ dications within the pores. It was determined that less than 0.06 PQT$^{2+}$ dications per strut of MOF-177 were incorporated in the pores. These results show that specific stereoelectronic host-guest interactions, rather than just simple diffusion and adsorption, are responsible for the all but quantitative formation of the BORG-1 pseudorotaxanes.

UV/Visible Absorption and Fluorescence Studies of Strut 2 and the Pesudorotaxane [PQT ⊂ 2].2PF$_6$:

UV/visible spectroscopy was performed on an Agilent 8453 Spectroscopy System. Emission spectra were recorded on a coupled charge device (CCD) through a SpectraPro 2300i 0.300 m imaging Triple Grating monochromator/spectrograph, excited by a 377 nm/16 mW laser.

Measurement of the Binding Constant of PQT.2PF$_6$ and Strut 2 by Spectrophoto-Metric Titration:

TABLE 1

The charge-transfer absorptions at 435 nm of the pseudorotaxane [PQT ⊂ 2] · 2PF$_6$ in eight samples of differing concentrations.

| [PQT] (mM) | 0.250 | 0.500 | 1.00 | 2.50 | 5.00 | 10.0 | 15.0 | 20.0 |
|---|---|---|---|---|---|---|---|---|
| ΔA (a.u.) | 0.105 | 0.137 | 0.203 | 0.322 | 0.376 | 0.410 | 0.435 | 0.462 |

The concentration of strut 2 was set at 0.500 mM in all samples. The various concentrations of PQT.2PF6 were added and the corresponding absorptions were measured with UV/vis spectrometry. ΔA is the absolute absorption corrected using a blank control sample ([PQT.2PF6]=0).

Figure 19:
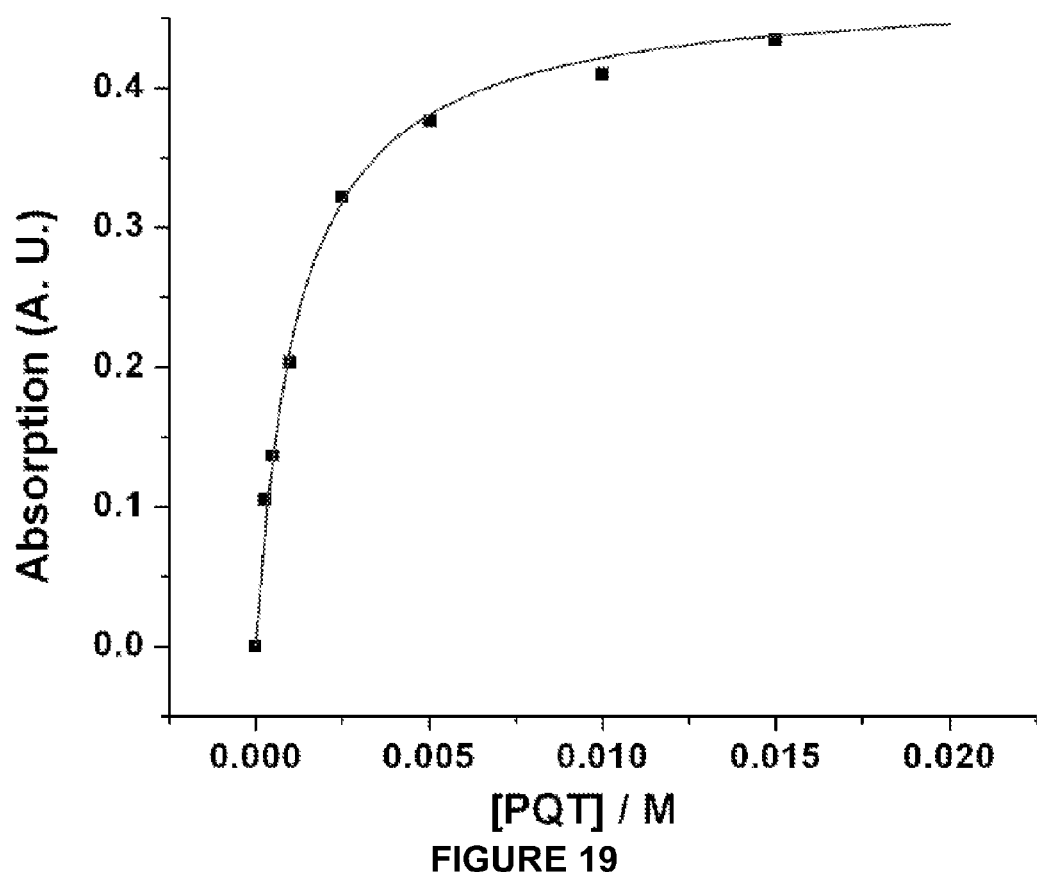
FIG. 19. ΔA vs. [PQT]/. The concentration of strut 2 was kept constant at 0.500 mM. Optical pathway=1.0 cm. The continuous line was calculated for K=829±71 M$_{-1}$ and Δs=944±19 M$^{-1}$·cm$^{-1}$.
Figure 20:
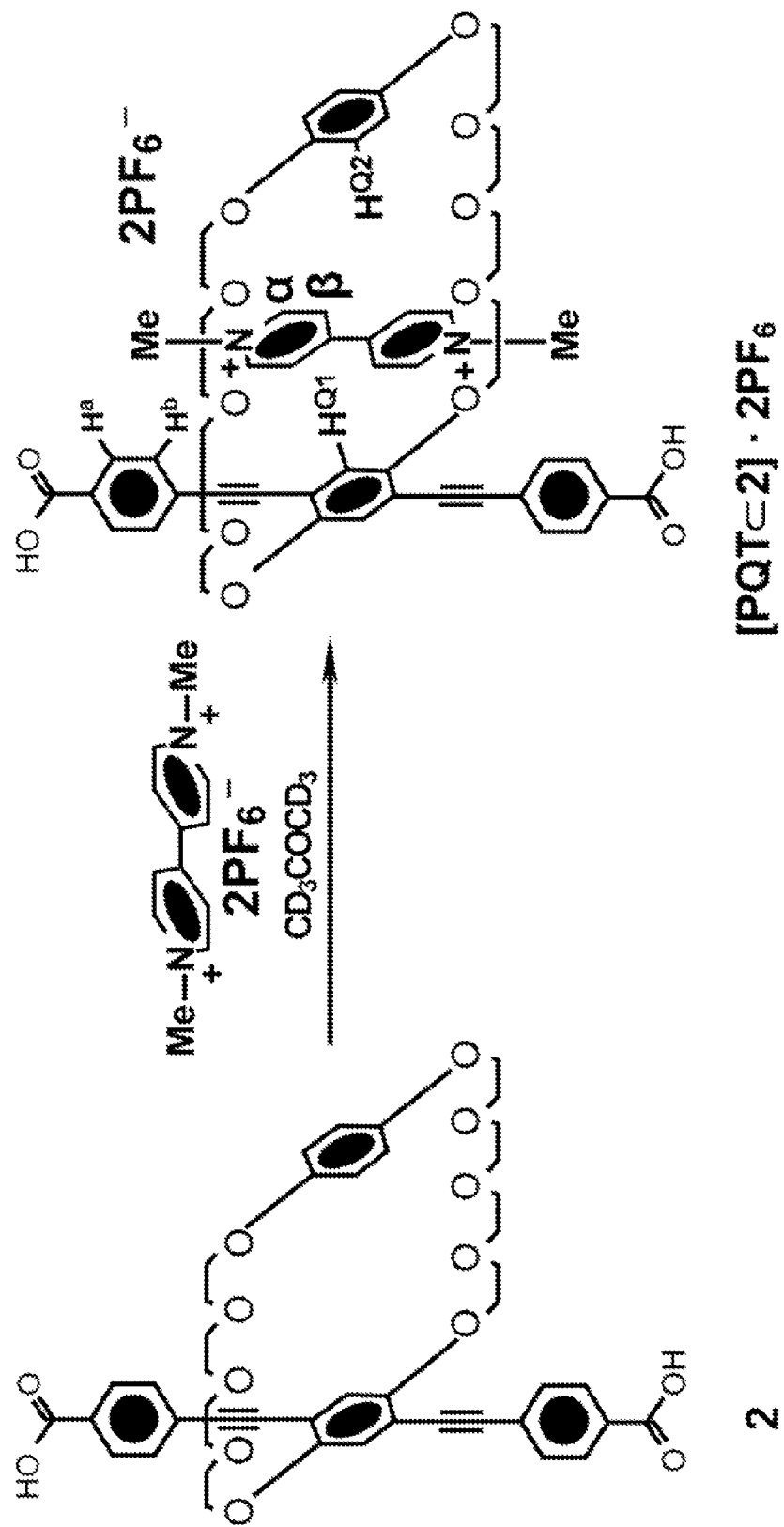
FIG. 20. Shows the formation of the pseudorotaxane [PQT ⊂ 2].2PF$_6$
Figure 21:
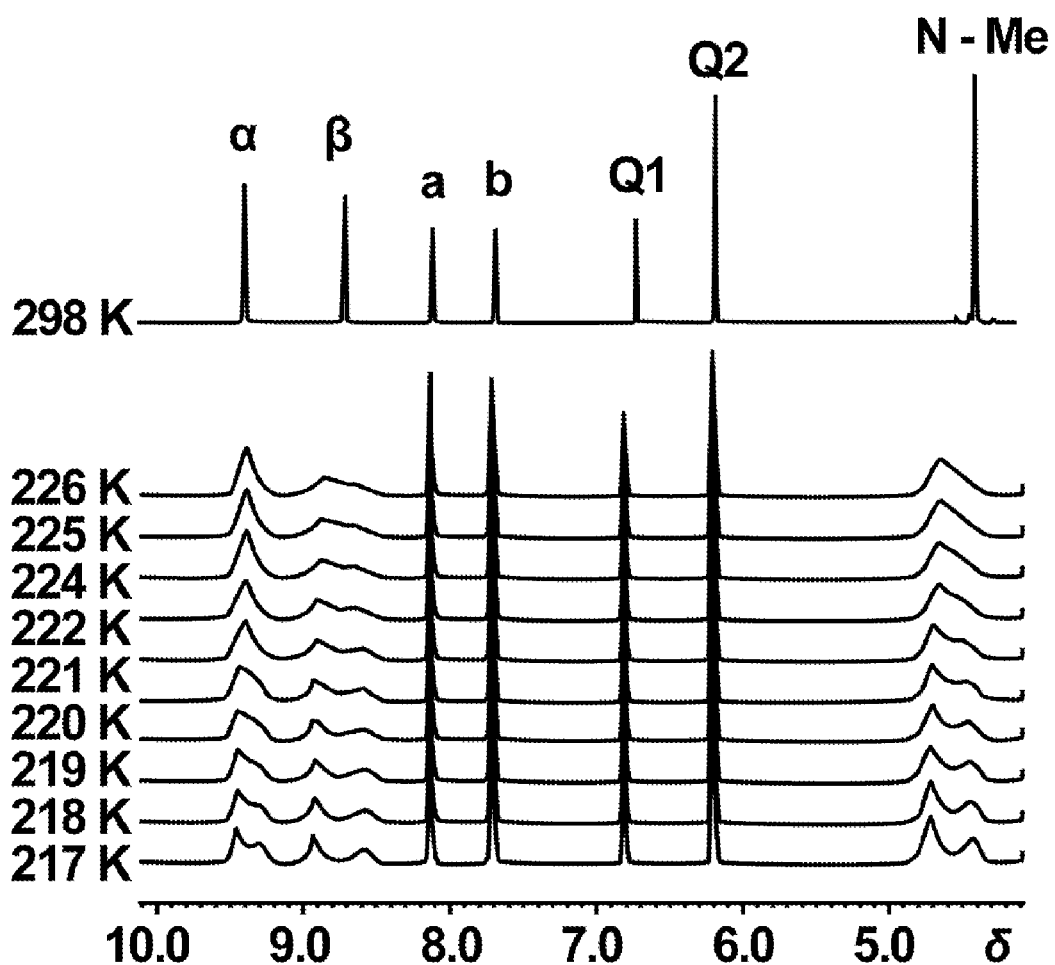
FIG. 21. Shows $^1$H NMR spectra of PQT.2PF$_6$ (1.2×10$^{-3}$ mM): 2 (4.0×10$^{-4}$ mM)=3:1 in CD$_3$COCD$_3$ at various temperatures. The exchange of the complexed and uncomplexed PQT$^{2+}$ was slowed down at lowered temperatures, causing the separation of signals for α, β, and N-Me protons from the PQT$^{2+}$.
Figure 22:
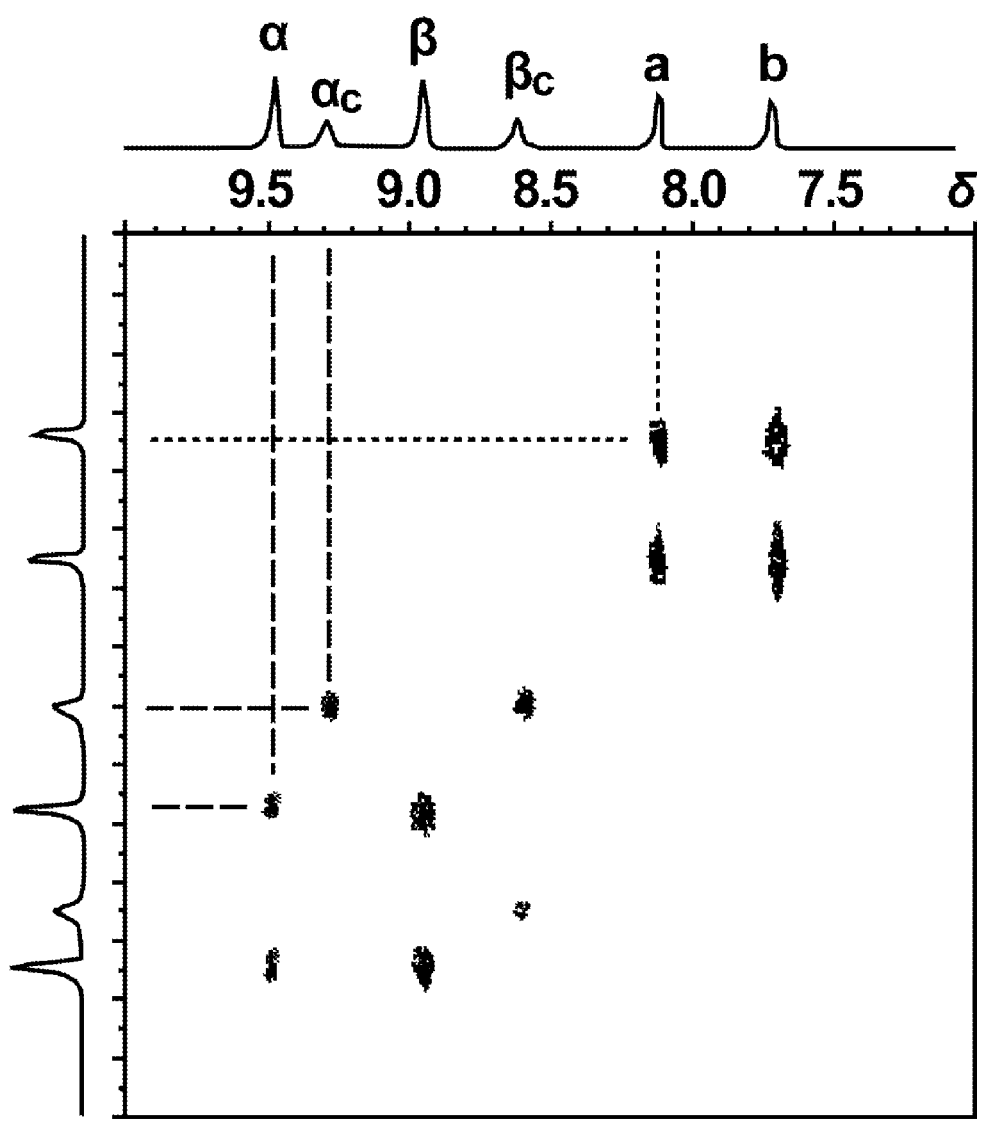
FIG. 22. Shows $^1$H-$^1$H COSY NMR spectrum and [1]H-$^{13}$C HMQC spectrum of PQT.2PF6 (1.2×10$^{-3}$ mM): 2 (4.0×10$^{-4}$ mM)=3:1 in CD3COCD3 at 200 K. Correlations among nuclei from PQT, (4-carboxyphenyl)ethynyl, and hydroquinone moieties are indicated.
Figure 22:
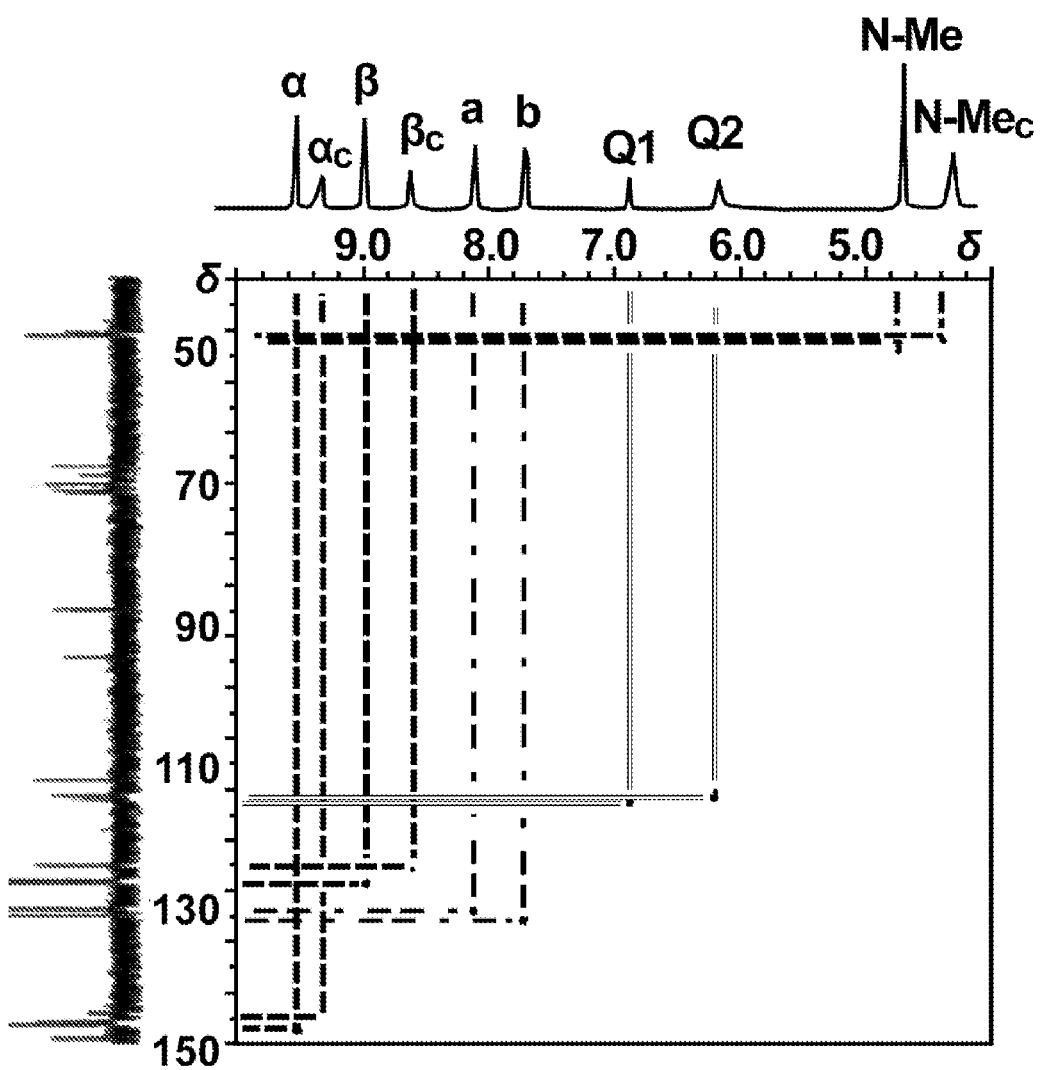
Figure 23:
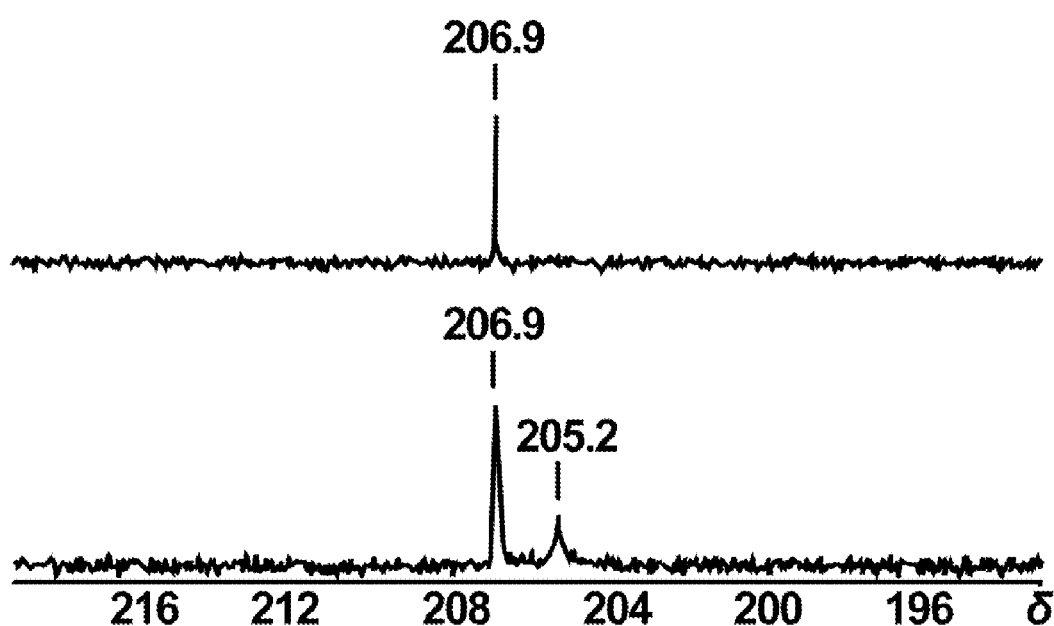
FIG. 23. Shows $^{15}$N NMR Spectra of a) PQT.2PF6 (1.2×10$^{-3}$ mM) and b) PQT.2PF6 (1.2×10$^{-3}$ mM): 2 (4.0×10$^{-4}$ mM)=3:1 in CD3COCD3 at 200 K. Complexed PQT2+ (205.2 ppm) displayed a chemical shift 1.7 ppm lower than the uncomplexed species (206.9 ppm) as the consequence of the shielding effect of the crown ether.
Figure 24:
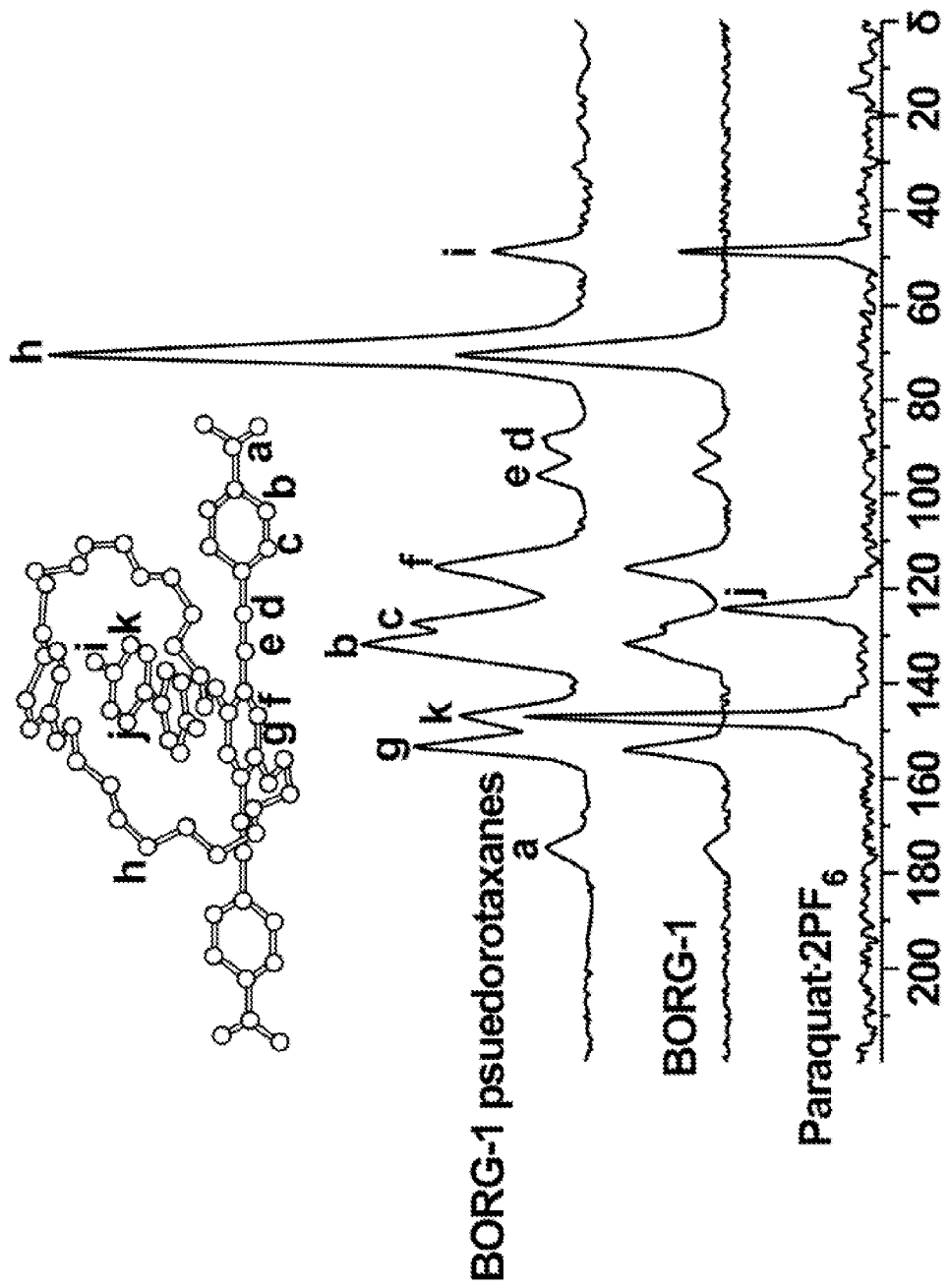
FIG. 24. Shows comparison of solid-state 13C CP/MAS NMR spectra of BORG-1 pseudorotaxanes (top), BORG-1 (middle), and PQT.2PF6 (bottom). The 13C CP/MAS NMR spectrum of BORG-1 pseudorotaxanes did not show a significant shift compared to those of BORG-1 and free PQT.2PF6.
Figure 25:
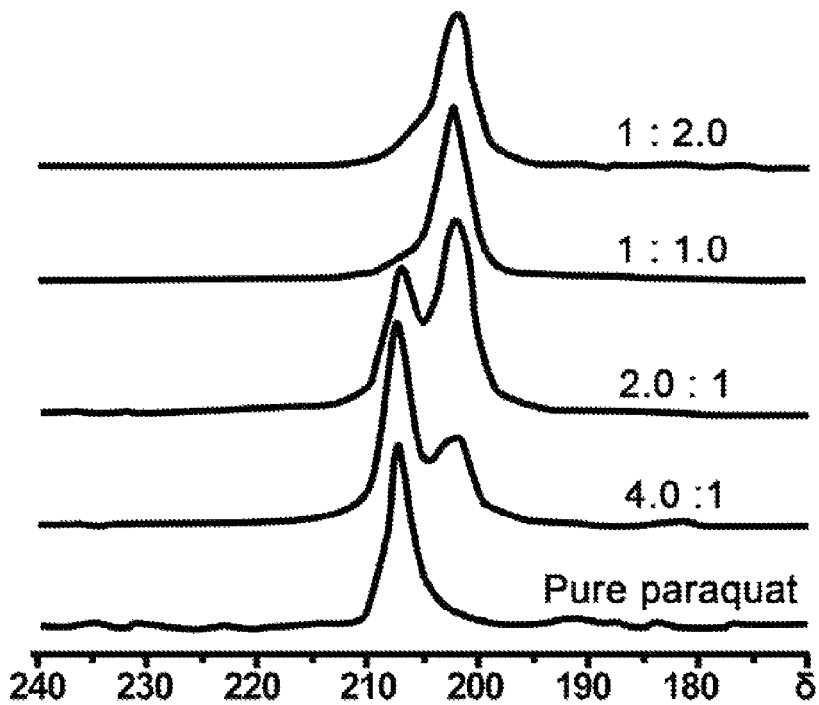
FIG. 25. Shows solid-state 15N CP/MAS NMR spectra of [PQT ⊂ 2].2PF$_6$. Mole ratios of PQT.2PF6 with strut 2 are 1:2.0 (top), 1:1.0 (2$^{nd}$ from top), 2.0:1 (middle), and 4.0:1 (2$^{nd}$ from bottom). The 15N CP/MAS NMR spectrum of pure PQT.2PF6 is shown in red. The mean chemical shift of 15N in free PQT.2PF6 was 207.0 ppm, while that of the complexed PQT.2PF6 was 202.1 ppm.
Figure 26:
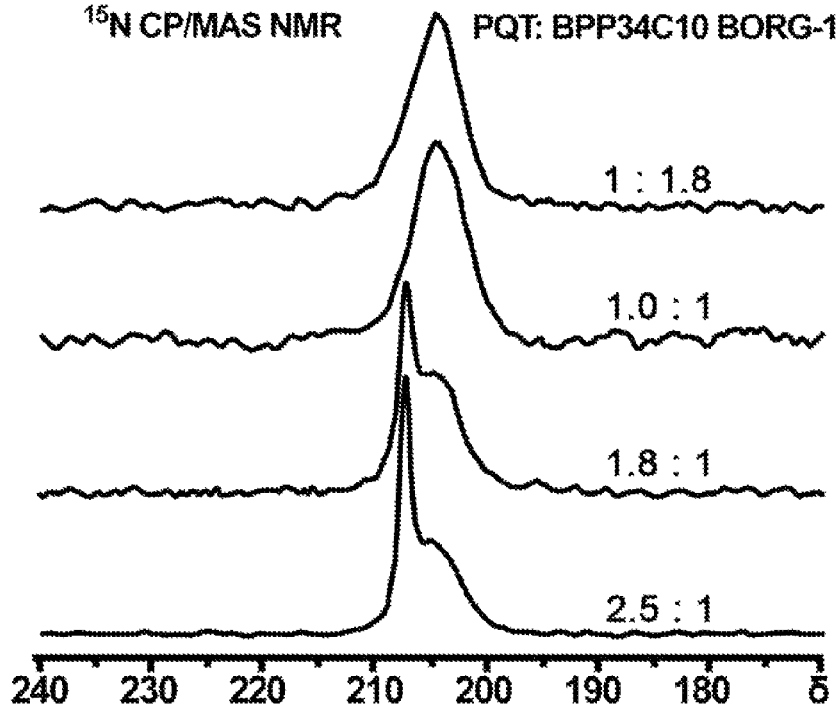
FIG. 26. Shows solid-state 15N CP/MAS NMR spectra of BORG-1 pseudorotaxanes. Mole ratios of PQT.2PF6 with BPP34C10 in BORG-1 were 1:1.8, 1:1, 1.8:1, 2.5:1. The mean chemical shift of 15N in free PQT.2PF6 was 207.2 ppm, while that in PQT.2PF6 complexed with BORG-1 was 204.6 ppm.
Figure 27:
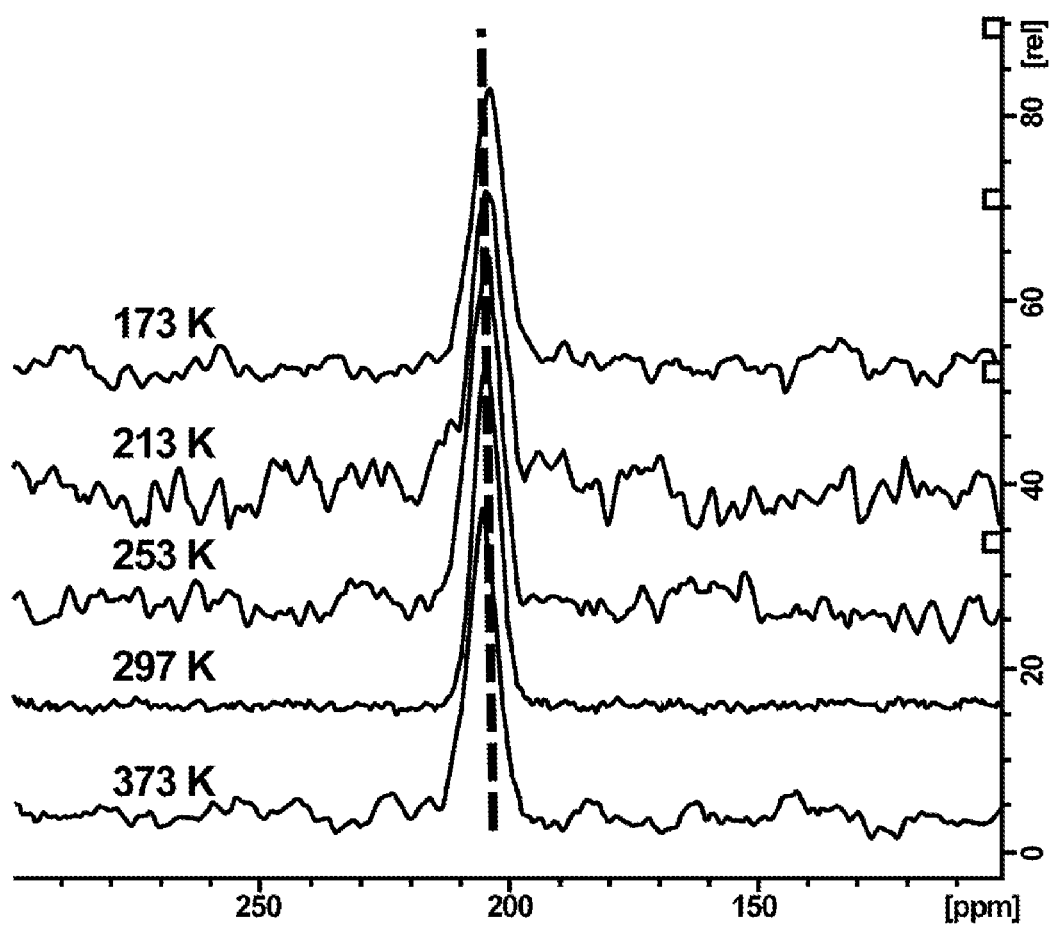
FIG. 27. Shows solid-state 15N CP/MAS NMR spectra of BORG-1 pseudorotaxanes (BORG-1 and PQT.2PF6 in 1:1 ratio) at variable temperature from 173 to 373 K. No peak split or widening was observed.
Figure 28:
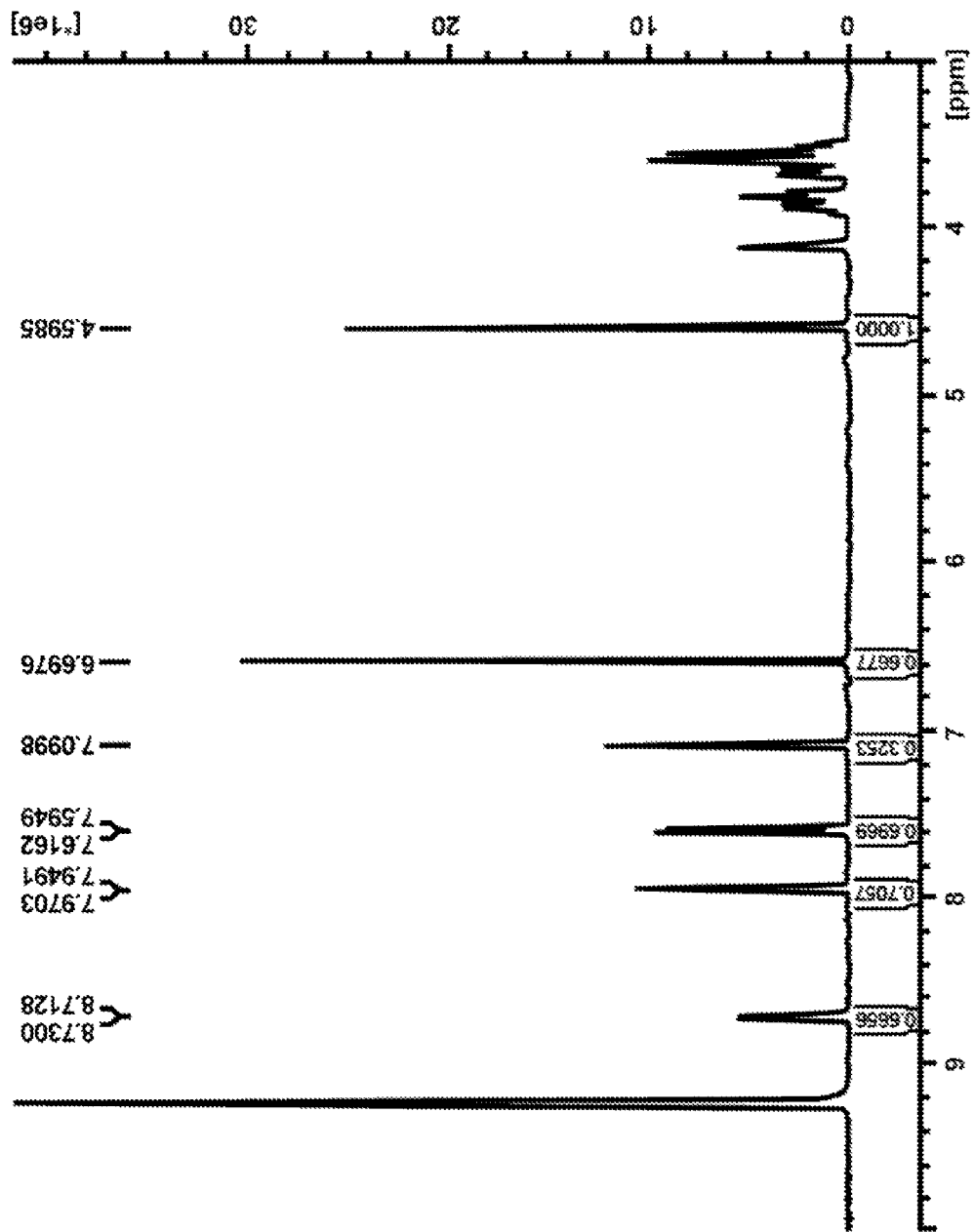
FIG. 28. Shows 1H NMR spectrum of BORG-1 pseudorotaxanes after digestion. Integrations of peaks at 7.96 ppm (d, 4H, Ar—H$^a$ in 2, $^3$J=8.5 Hz) and 4.60 ppm (s, 6H, N—CH$_3$ in PQT$^{2+}$) in $^1$H show that the ratio of PQT$^{2+}$ to strut 2 is 1:1.
Figure 29:
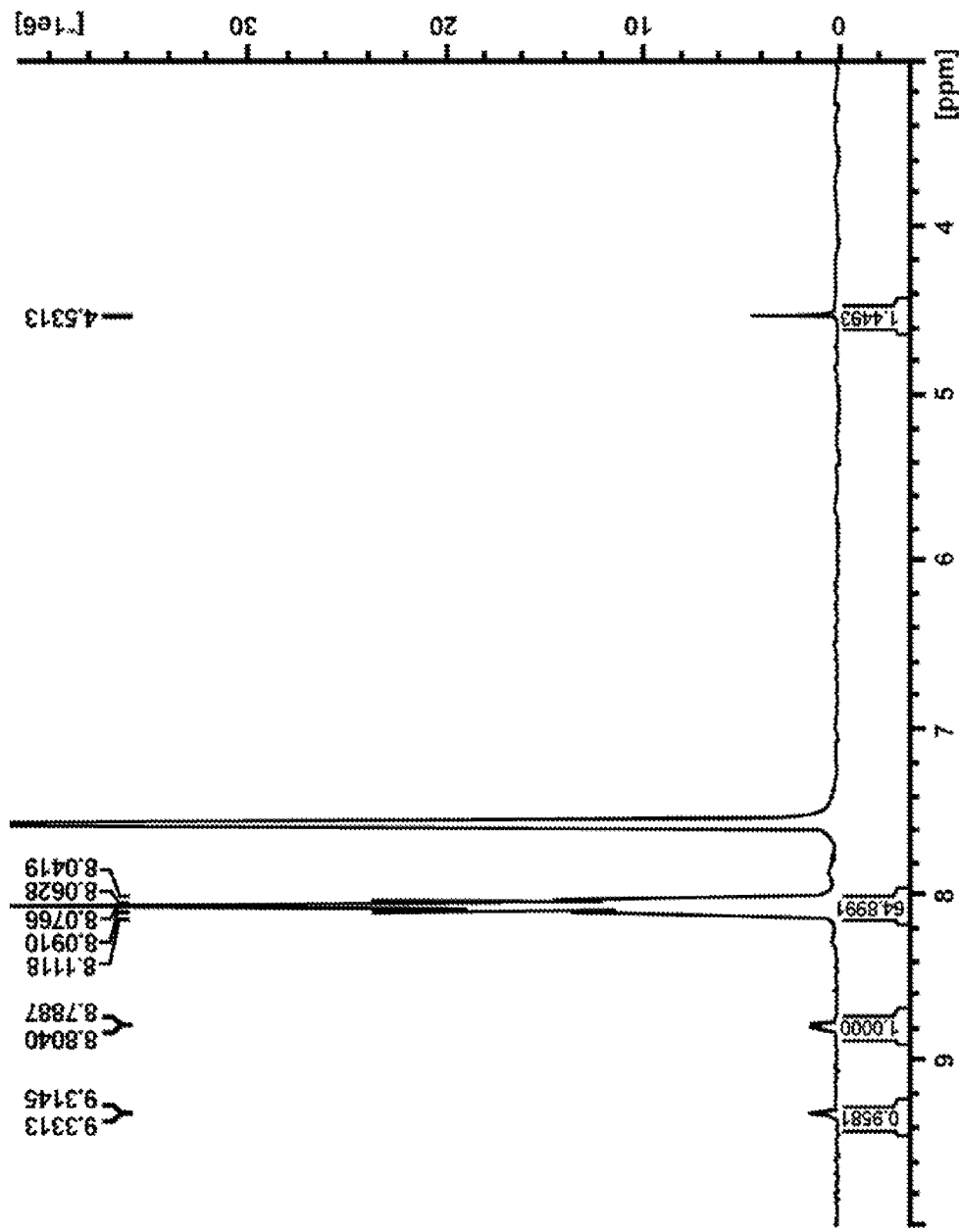
FIG. 29. Shows $^1$H NMR spectrum of PQT$^{2+}$ included MOF-177 after digestion. Integrations of peaks at 8.08 ppm ([15]H, Ar—H in H3BTB) and 4.53 ppm (s, 6H, N—CH$_3$ in PQT$^{2+}$) in $^1$H show that less than 0.06 PQT$^{2+}$ was included for each BTB strut.
Figure 30:
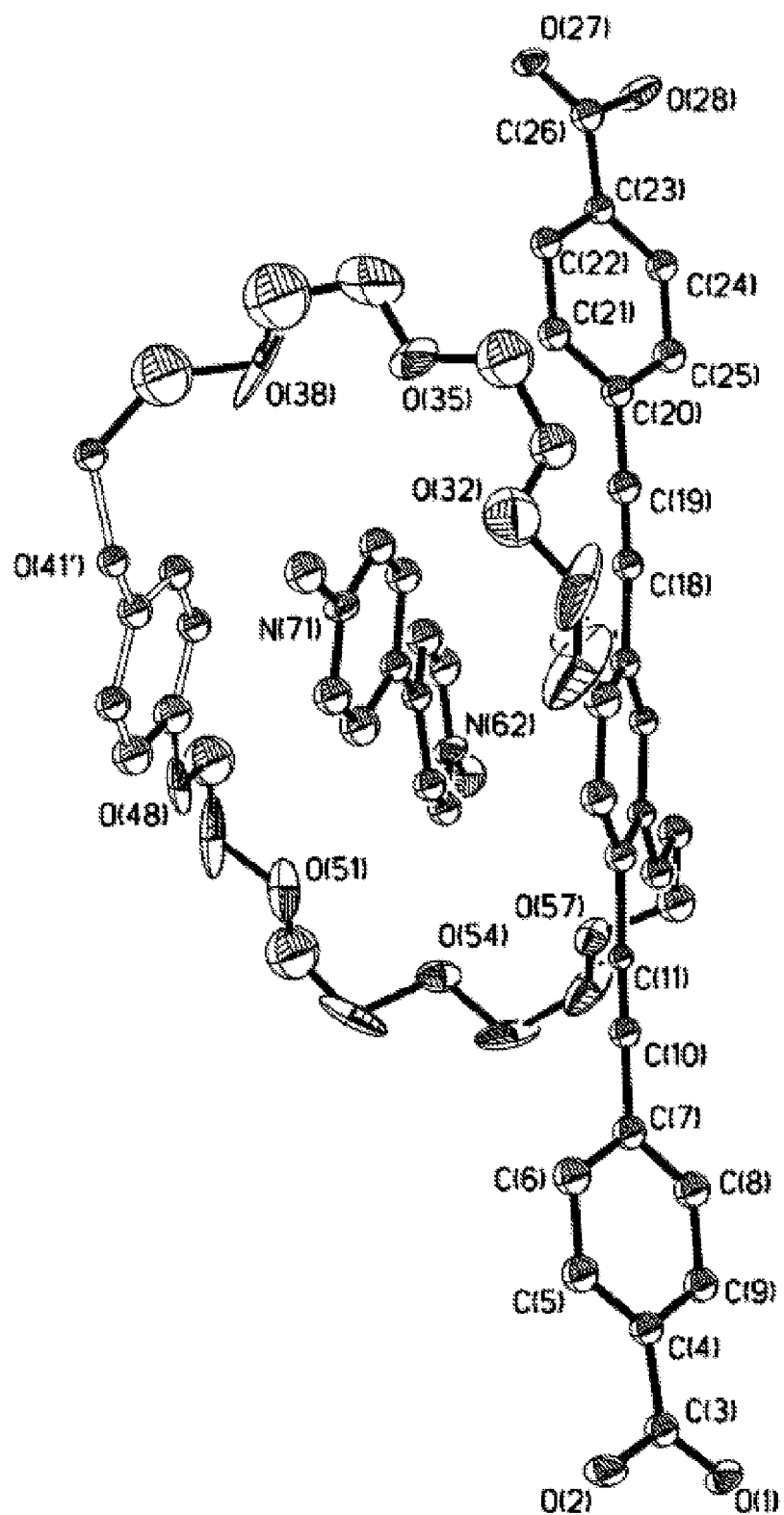
FIG. 30. Shows an ORTEP drawing of the asymmetric unit of [PQT ⊂ 2].2PF$_6$. Hydrogen atoms, solvent molecules and anions were excluded for clarity. Only one component of each disordered group is shown.
Figure 31:
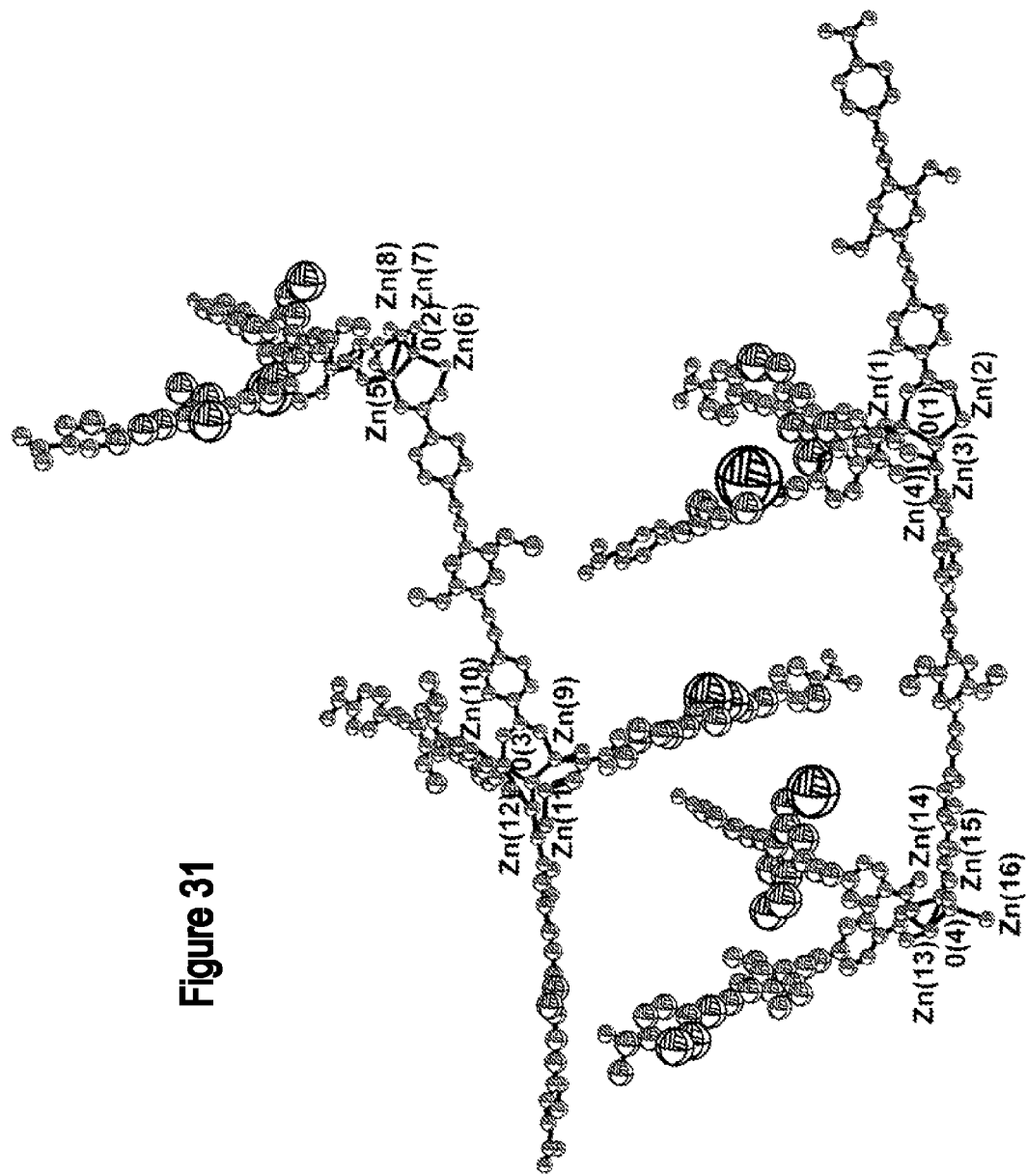
FIG. 31. Shows an ORTEP drawing of the asymmetric unit of MOF-1000, excluding hydrogen atoms and solvents.
Figure 32:
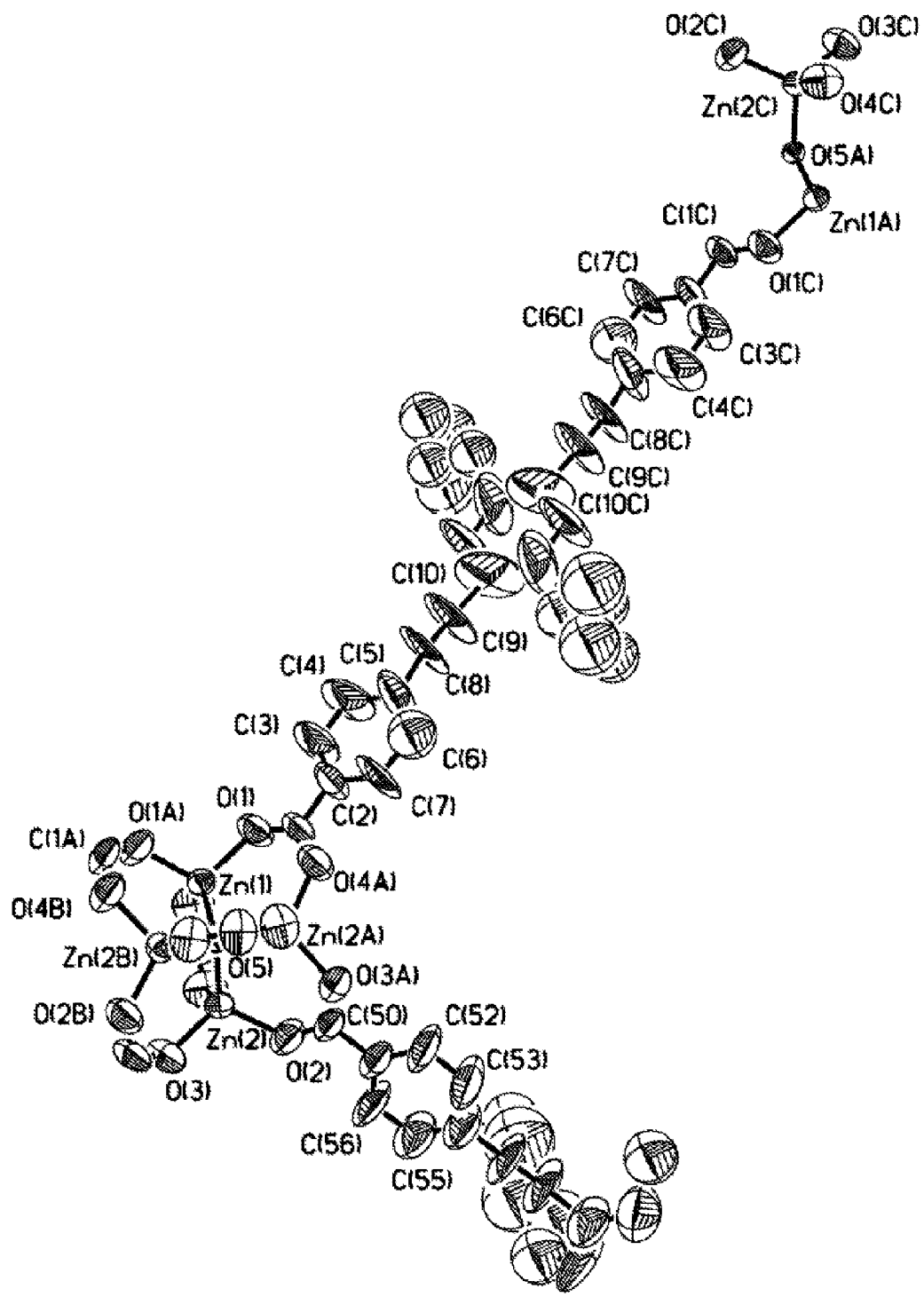
FIG. 32. Shows an ORTEP drawing of BORG-1A, with a full Zn$_4$O SBU and 1.5 links. Hydrogen atoms, hydroquinone rings and partial bismethylenedioxy units of the tetraethylene glycol loops in BPP34C10 are not shown.
Figure 33:
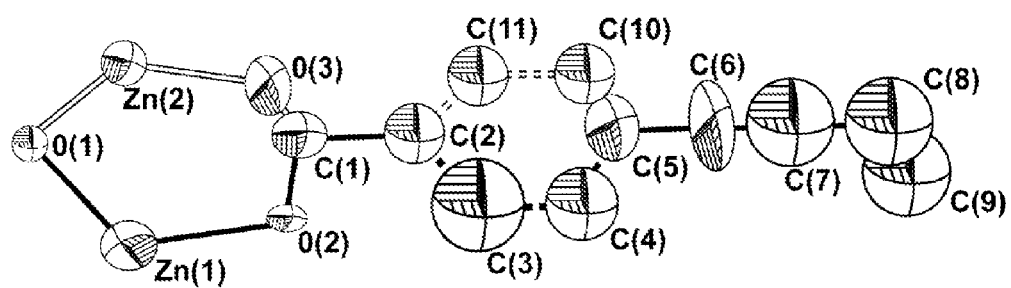
FIG. 33. Shows an ORTEP drawing of BORG-1 asymmetric unit with both components of disorder shown, excluding the crown ethers, hydrogen atoms and guest entities. All ellipsoids are displayed at the 10% probability level.
Figure 34:
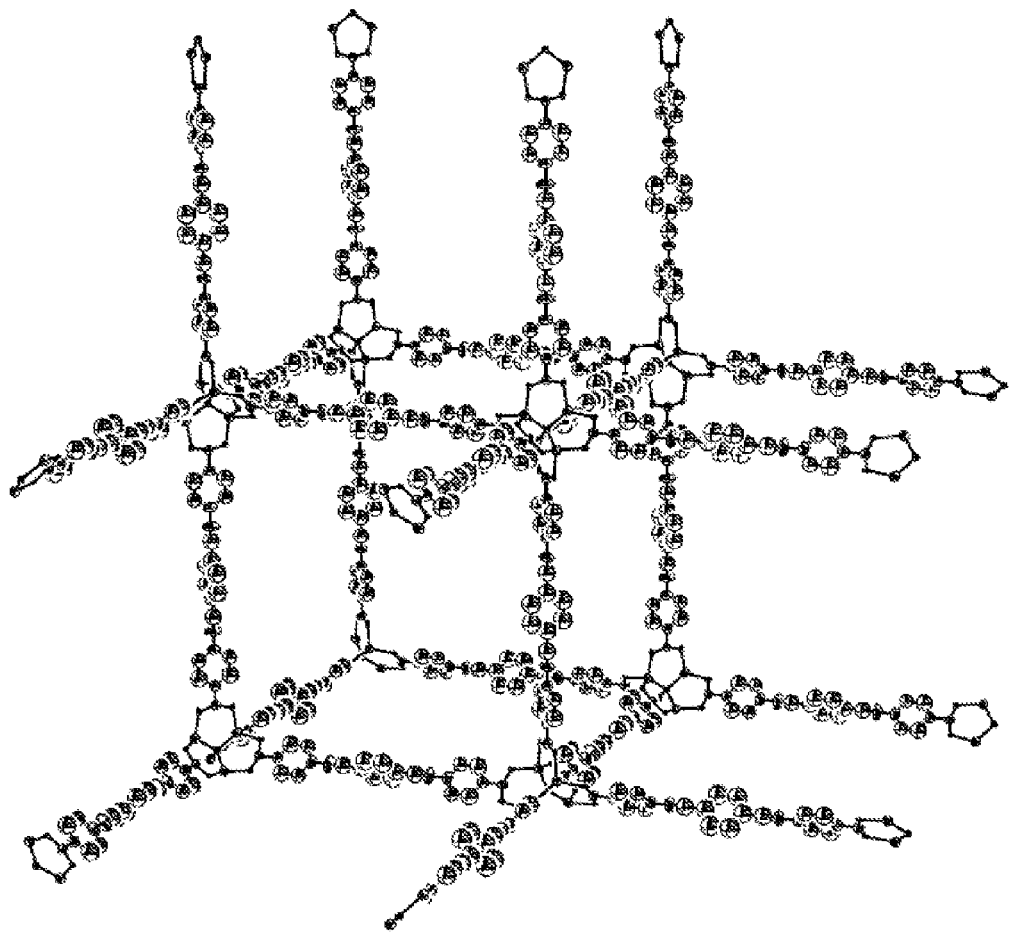
FIG. 34. Shows an ORTEP drawing of BORG-1 framework with only one component of the disorder shown, excluding the crown ethers, hydrogen atoms and guest entities. All ellipsoids are displayed at the 10% probability level.
Figure 35:
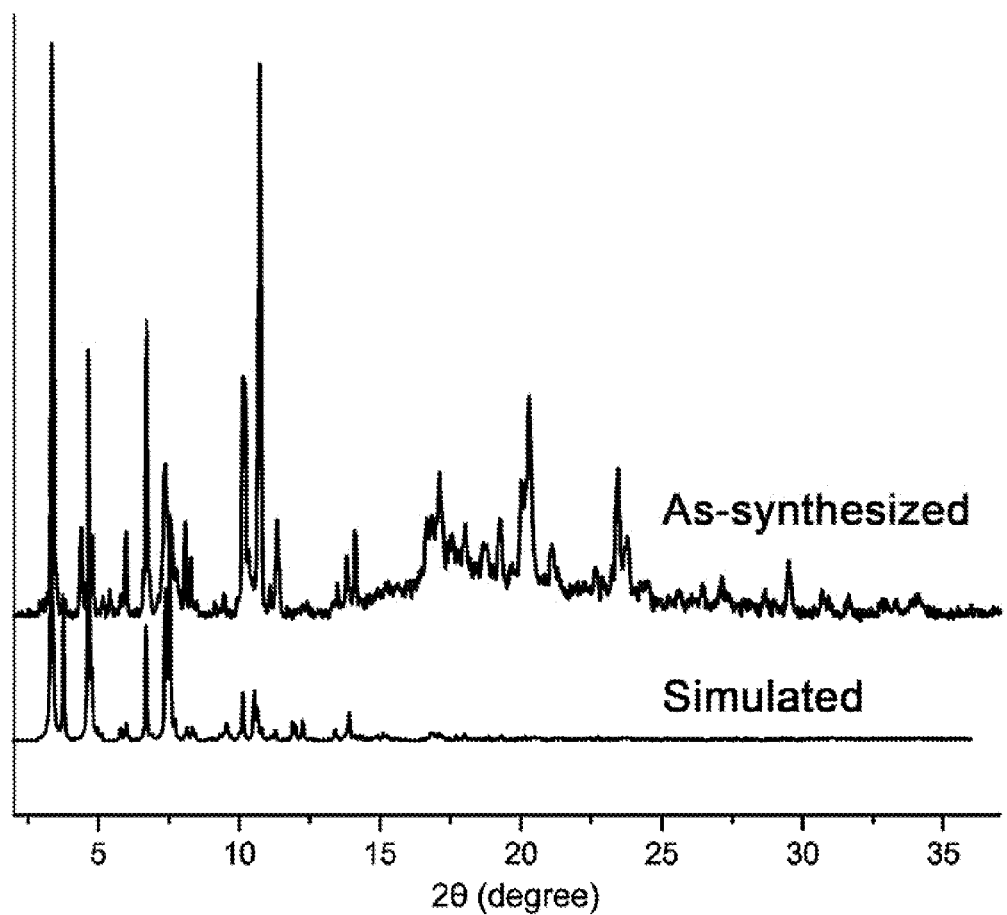
FIG. 35. Shows a comparison of the experimental PXRD pattern of as-synthesized MOF-1000 (top) with the one simulated from its single crystal structure (bottom). The very high degree of correspondence between the patterns indicates that the bulk material has the same structure as the single crystal.
Figure 36:
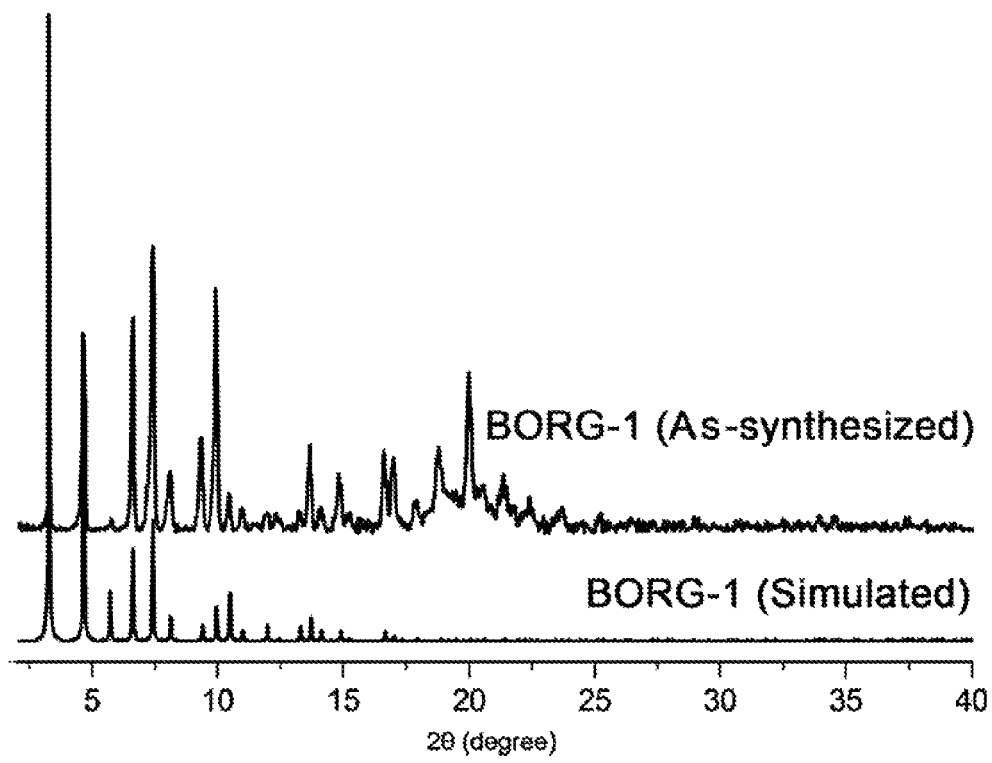
FIG. 36. Shows a comparison of the experimental PXRD pattern of as-synthesized BORG-1 (top) with the one simulated from its single crystal structure (bottom). The very high degree of correspondence between the patterns indicates that the bulk material has the same structure as the single crystal.
Figure 37:
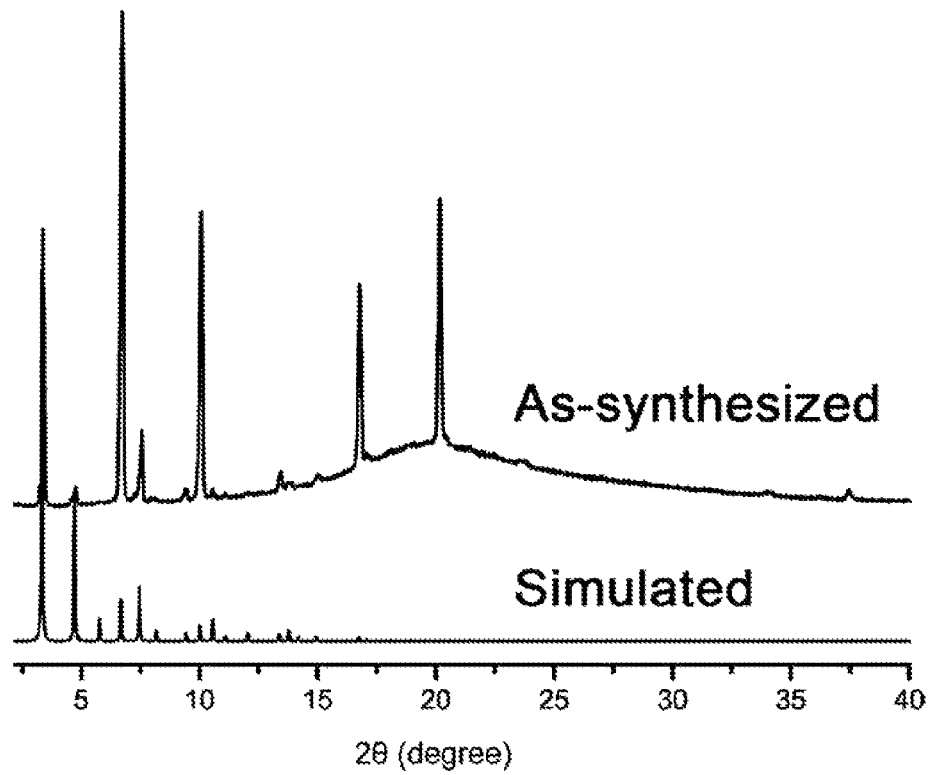
FIG. 37. Shows a comparison of the experimental PXRD pattern of as-prepared BORG-2 (top) with the one simulated from its single crystal structure (bottom, identical with BORG-1 simulation). The very high degree of correspondence between the patterns indicates that the bulk material has the same structure as the single crystal.
Figure 38:
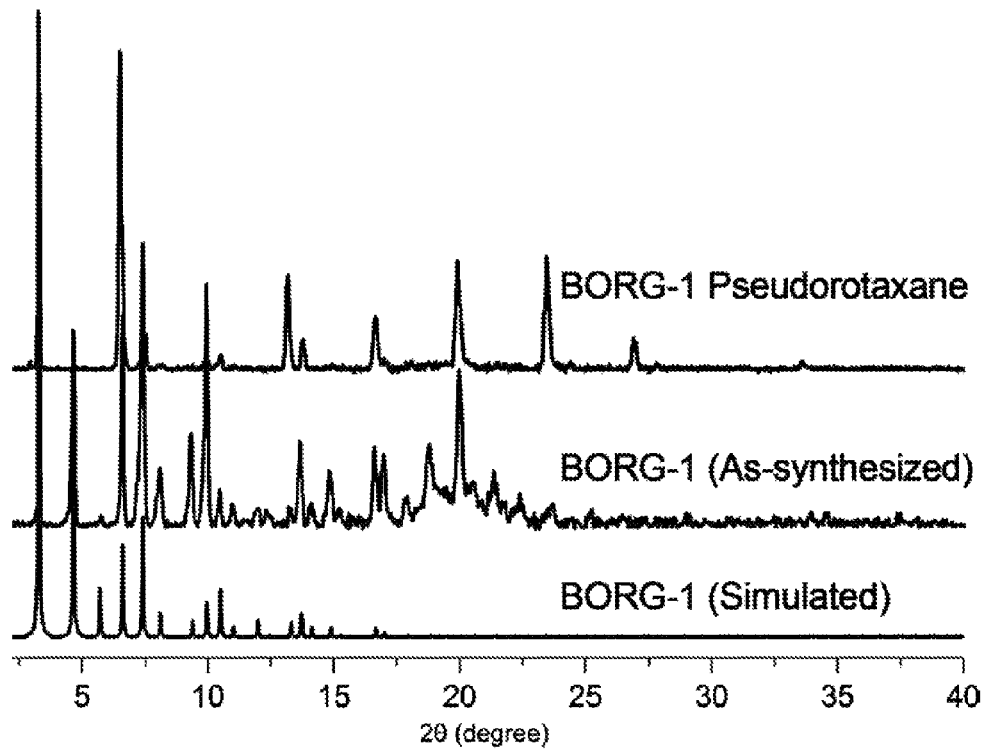
FIG. 38. Shows a comparison of the experimental PXRD patterns of BORG-1 pseudorotaxanes (top) and BORG-1 (as-synthesized, middle; simulated, bottom). The framework retains the same structure after inclusion of paraquat.

The binding constant was obtained by computer fitting (FIG. 19) of the experimental absorbance values to the following equation (3):

$$\frac{\Delta A}{b} = \frac{[2]_0 K (\Delta \varepsilon)[PQT]}{1 + K[PQT]}$$

where ΔA is the absorbance of the charge-transfer complex measured at a host concentration [2]0=0.500 mM and a guest concentration [PQT], b is the optical path length (1 cm), Δε is the molar absorptivity of the charge-transfer complex, and K is the equilibrium constant for the formation of the complex. The experimental data points were consistent with 1:1 stoichiometry for all the complexes.

Solution NMR Spectroscopic Studies of the Pseudorotaxane [PQT ⊂ 2].2PF$_6$:

$^{15}$N-labeled paraquat bishexafluorophosphate (PQT.2PF$_6$) (8.7 mg, 0.018 mmol) and strut 2 (5.0 mg, 0.006 mmol) were dissolved in CD$_3$COCD$_3$ (0.5 mL). $^1$H, $^{13}$C, $^{15}$N, $^1$H-$^1$H COSY, and $^1$H-$^{13}$C HMQC NMR experiments were conducted at room temperature and lowered temperatures.

TABLE 2

Changes of chemical shifts of selected nuclei in the pseudorotaxane (δc) [PQT ⊂ 2] · 2PF6 (1.2 × 10–3 mM, 200 K, CD3COCD3) compared to the uncomplexed (δuc) PQT2+. Δδ is the chemical shift difference (in ppm).

| Nuclei | $^1$H | | | $^{13}$C | | | $^{15}$N |
|---|---|---|---|---|---|---|---|
| | α | β | N—Me | α | β | N—Me | N—Me |
| δ$_{uc}$ | 9.50 | 8.96 | 4.72 | 147.1 | 126.7 | 48.5 | 206.9 |
| δ$_c$ | 8.96 | 8.62 | 4.34 | 146.6 | 124.5 | 48.1 | 205.2 |
| Δδ | −0.20 | −0.34 | −0.38 | −0.5 | −2.2 | −0.4 | −1.7 |

Solid-State 13C and 15N CP/MAS NMR Spectroscopic Studies of BORG-1 and BORG-1 Pseudorotaxanes.

Solid-State 13C CP/MAS and $^{15}$N CP/MAS nuclear magnetic resonance spectroscopy High resolution solid-state nuclear magnetic resonance (NMR) spectra were recorded at ambient pressure on a Bruker DSX-300 spectrometer using a standard Bruker magic-angle spinning (MAS) probe with 4 mm (outside diameter) zirconia rotors. The magic angle was adjusted by maximizing the number and amplitudes of the signals of the rotational echoes observed in the $^{79}$Br MAS FID signal from KBr. Cross-polarization with MAS (CP/MAS) was used to acquire 13C data at 75.47 MHz. The $^1$H and $^{13}$C ninety-degree pulse widths were both 4 ms. The CP contact time was 3 ms. High power two-pulse phase modulation (TPPM) $^1$H decoupling was applied during data acquisition. The decoupling frequency corresponded to 72 kHz. The MAS sample-spinning rate was 10 kHz. Recycle delays varied from 3 to 30 s, depending upon the compound as determined by observing no apparent loss in the 13C signal from one scan to the next. The 13C chemical shifts are given relative to tetramethylsilane as zero ppm, calibrated using the methine carbon signal of adamantane assigned to 29.46 ppm as a secondary reference.

CP/MAS was also used to acquire $^{15}$N data at 30.41 MHz. The CP contact time was 3 ms at ambient temperature. High power two-pulse phase modulation (TPPM) $^1$H decoupling was applied during data acquisition. The decoupling frequency corresponded to 72 kHz.

The MAS sample-spinning rate was 5 kHz. The recycle delay time was 3 s, which was determined from the $^{13}$C CP/MAS experiments. The $^{15}$N chemical shifts were externally referenced with $^{15}$N-glycine (32.6 ppm versus liquid NH$_3$ at 25° C.). In the variable temperature experiment, the temperature calibration was performed using the 207Pb resonance of Pb(NO$_3$)$_2$. The CP contact time varied from 3 to 5 ms, depending upon the temperature.

Solid-State 15N CP/MAS Nuclear Magnetic Resonance Spectroscopy of [PQT⊂2].2PF6.

Strut 2 and PQT.2PF$_6$ (isotope labeled with 25% abundance of $^{15}$N) with different mole ratios (1:4, 1:2, 1:1, 2:1) were dissolved in Me$_2$CO. The color change of the solution (yellow to orange) indicated pseudorotaxane formation. The solvent was removed by evaporation and the solid was dried under vacuum ($10^{-2}$ Torr) for 4 h at room temperature.

Solid-State 15N CP/MAS Nuclear Magnetic Resonance Spectroscopy of BORG-1 Pseudorotaxanes. Preparation of BORG-1 Pseudorotaxanes (BORG-1: $PQT.2PF_6$=1:1):

BORG-1 crystalline solid (approximately 20 mg) in fresh DMF was exchanged with fresh Me2CO (10 mL) 3 times a day for 3 days. After Me2CO was decanted, saturated $PQT.2PF_6$ (isotope labeled with 25% abundance of 15N) solution in $Me_2CO$ (5 mL) was added. The color of the crystals immediately turned red. After sitting for 6 h, the solid was isolated by filtration and flush-washed with $Me_2CO$ (10 mL). The solid was dried under vacuum ($10^{-2}$ Torr) for 24 h at room temperature.

Preparation of BORG-1 Pseudorotaxanes (BPP34C10 in BORG-1: $PQT.2PF_6$=1.8:1, 1:1.8 and 1:2.5):

BORG-1 (about 10 mg) crystalline solid in DMF was exchanged with fresh Me2CO (10 mL) 3 times a day for 3 days. After $Me_2CO$ was decanted, $PQT.2PF_6$ (isotope labeled with 25% abundance of $^{15}N$) solution in $Me_2CO$ (3 mL) was added. The amount of $PQT.2PF_6$ varies from 6 mg to 22 mg in every sample. The crystals turned red. After sitting for 6 h, the solid was isolated by filtration and dried under vacuum ($10^{-2}$ Torr) overnight at room temperature.

After the solid-state $^{15}N$ CP/MAS experiment, 10 mg of the sample was transferred to a NMR tube. The solid was digested with 5 drops of DCl (20% in $D_2O$) and 0.5 mL DMSO-d6. The molar ratio of the strut and $PQT.2PF_6$ in each sample was determined by integration of peaks at 7.96 ppm (d, 4H, Ar—$H^a$ in 2, $^3J$=8.5 Hz) and 4.60 ppm (s, 6H, N—$CH_3$ in $PQT^{2+}$) in $^1H$ solution NMR spectra.

Determination of PQT.2PF6 Loading in BORG-1 and MOF-177 by 1H NMR Spectroscopy PQT.2PF6 Diffusion in MOF-177:

MOF-177 (about 10 mg) crystalline solid in DEF was exchanged with fresh Me2CO (10 mL) for 3 times a day for 3 days. After decanting the Me2CO, saturated $PQT.2PF_6$ solution in $Me_2CO$ (5 mL) was added. After sitting for 6 h, the crystals were isolated by filtration and flush-washed with $Me_2CO$ (10 mL). The solid was dried under vacuum ($10^{-2}$ Torr) for 24 h at room temperature. Determination of $PQT.2PF_6$ Loading by $^1H$ NMR: BORG-1 pseudorotaxanes and $PQT^{2+}$ included MOF-177 were digested in a mixture of 0.5 mL $CD_3SOCD_3$ and 0.1 mL DCl (20% in $D_2O$). The ratio of strut 2 and $PQT.2PF_6$ in BORG-1 pseudorotaxanes was determined by the integration of peaks of Ar—$H^a$ in 2 (d, 4H) and N—$CH_3$ in $PQT^{2+}$ (s, 6H) in $^1H$ solution NMR. The ratio of the strut 4,4',4"-benzene-1,3,5-triyl-tribenzoic acid ($H_3BTB$) and $PQT^{2+}$ in $PQT^{2+}$-included MOF-177 was determined by the integration of peaks of Ar—H in $H_3BTB$ ($^{15}H$) and N—$CH_3$ in $PQT^{2+}$ (s, 6H) in 1H solution NMR. Peak positions may vary in every experiment depending on the amount of DCl in the system.

Single Crystal X-Ray Diffraction Data Collection, Structure Solution and Refinement Procedures.

Data were collected on a Bruker SMART APEXII three circle diffractometer equipped with a CCD area detector and operated at 1200 W power (40 kV, 30 mA) to generate Cu Kα radiation (λ=1.5418 Å). The incident X-ray beam was focused and monochromated using Bruker Excalibur Gobel mirror optics. Crystals were mounted either on nylon CryoLoops (Hampton Research) with Paraton-N (Hampton Research), or in flame sealed borosilicate capillaries containing a small amount of mother liquor to prevent desolvation during data collection.

Initial ω-φ scans of each specimen were taken to gain preliminary unit cell parameters and to assess the mosaicity (i.e. breadth of spots between frames) of the crystal to select the required frame width for data collection. For all cases frame widths of 0.5° were judged to be appropriate and full hemispheres of data were collected using the Bruker APEX2 software suite to carry out overlapping φ and ω scans at different detector (2θ) settings. Following data collection, reflections were sampled from all regions of the Ewald sphere to redetermine unit cell parameters for data integration and to check for rotational twinning using CELL_NOW. Following exhaustive review of collected frames the resolution of the dataset was judged, and if necessary regions of the frames where no coherent scattering was observed were removed from consideration for data integration. Data were integrated using Bruker APEX2 V 2.1 software with a narrow frame algorithm and a 0.400 fractional lower limit of average intensity. Absorption corrections were ineffectual for improving the quality of data, which is not unexpected for small crystals of low density solids containing primarily light atoms. Space group determination and tests for merohedral twinning were carried out using XPREP (10). In all cases the highest possible space group was chosen and no indications of merohedral twinning were observed.

All structures were solved by direct methods and refined using the SHELXTL '97 software suite. Atoms were located from iterative examination of difference F-maps following least-squares refinements of the earlier models. Final models were refined anisotropically (if the number of data permitted and stable refinement could be reached) until full convergence was achieved. Several structures contained disordered components within the structure. In these cases occupancies X and (1−X) and equivalent displacement parameters were assigned to each pair of atoms in the disordered groups and X was refined as an independent free variable. Some atoms could not be located precisely due to high disorder (atoms in crown ethers in BORG-1, BORG-1A etc.). Hydrogen atoms were placed in calculated positions and included as riding atoms with isotropic displacement parameters 1.2-1.5 times Ueq of the attached carbon atoms. Modeling of electron density within the voids of the frameworks did not lead to identification of guest entities in all structures due to the lowered resolution of the data. This difficulty, which is typical of porous crystals that contain solvent filled pores, lies in the raw data where observed strong (high intensity) scattering becomes limited to ~1.0 Å at best, with higher resolution data present but weak (low intensity). As is a common strategy for improving X-ray data, increasing the exposure time of the crystal to X-rays did not ameliorate the quality of the high angle data in these cases, as the intensity from low angle data saturated the detector and minimal improvement in the high angle data was achieved. Additionally, diffuse scattering from the highly disordered crown ethers and solvents in the void spaces within the crystal and solvents from the capillary used to mount the crystal contributed to the background noise and the 'washing out' of high angle data. The only optimal crystals suitable for analysis were generally small and weakly diffracting, and unfortunately, larger crystals, which might improve the quality of the data, presented a lowered degree of crystallinity, and optimization of crystal growing conditions for large high-quality specimens has not yet been fruitful. For all extended framework structures it was also more reasonable to model against data collected at elevated temperatures (−50 to −15° C., rather than −120 to −100° C.) when guest entities in the structures were allowed to move freely and therefore did not contribute coherent scattering terms to the observed structure factors. Conversely, at cryogenic temperatures it was found that free solvent in the crystal would "freeze" into non-ordered arrays within the pore structure. In such cases the modeling of the disordered guest entities becomes intractable and interferes with determination of the framework. Thus, electron density within void spaces which could not be assigned to any definite guest entity was modeled as isolated oxygen and carbon atoms, and the foremost errors in all the models lie with assignment of guest electron density. To prove the correctness of the atomic positions in the framework, the application of the SQUEEZE routine of A. Spek has been performed when applicable. However, atomic co-ordinates for the "non-SQUEEZE" structures have also been presented and the CIFs were also submitted for the cases where the program SQUEEZE has been employed. All structures were examined using the Adsym subroutine of PLATON to assure that no additional symmetry could be applied to the models. All ellipsoids in ORTEP diagrams are displayed at the 30% probability level unless noted otherwise.

Experimental and Refinement Details for [PQT ⊂ 2].2PF$_6$

A red block shaped crystal (0.10×0.10×0.05 mm$^3$) of [PQT ⊂ 2].2PF6 coated with Paraton-N oil on a Cryo-Loop pin was mounted on a SMART APEXII three circle diffractometer equipped with a CCD area detector and operated at 1200 W power (40 kV, 30 mA) to generate Cu Kα radiation (λ=1.5418 Å) while being flash frozen to 100 K in a liquid N2 cooled stream of nitrogen. Full hemispheres of data were collected using the Bruker APEX2 software suite to carry out overlapping φ and ω scans at three different detector (2θ) settings (2θ=28, 60, 100°. A total of 9915 reflections were collected, of which 4650 were unique and 3240 of these were greater than 2σ(I). The range of θ was from 2.41 to 44.11°. Analysis of the data showed negligible decay during collection. The structure was solved in the triclinic Pspace group with Z=2 using direct methods. Atoms C40, O41, C42, C43, C44 and C47 were found to be disordered and were refined with the occupancy for each group modeled as its own independent free variable (X, 1–X). Two PF6– were found in the asymmetric unit, one of which was found to be disordered with half occupancy for each group. Two and a half acetone molecules were also found in every asymmetric unit. Due to the low data to parameter ratio, only P, O, N, some C and some F atoms were refined anisotropically. Hydrogen atoms were generated as spheres riding the coordinates of their parent atoms. A final ratio of 7.5 for reflections to parameters was achieved. Absorption correction was not performed. Final full matrix least-squares refinement on F2 converged to R1=0.0961 (F>2σ(F)) and wR2=0.2525 (all data) with GOF=1.061.

TABLE 3

Crystal data and structure refinement for [PQT ⊂ 2] · 2PF$_6$.

| | |
|---|---|
| Empirical formula | C65.50 H76 F12 N2 O16.50 P2 |
| Formula weight | 1446.22 |
| Temperature | 100(2) K |
| Wavelength | 1.54178 Å |
| Crystal system | Triclinic |
| Space group | P$\bar{1}$ |
| Unit cell dimensions | a = 11.0078(4) Å α = 73.836(2)° |
| | b = 16.9569(6) Å β = 83.257(2)° |
| | c = 19.1579(7) Å γ = 85.681(2)° |
| Volume | 3407.5(2) |
| Z | 2 |
| Density (calculated) | 1.409 Mg/m$^3$ |
| Absorption coefficient | 1.469 mm$^{-1}$ |
| F(000) | 1506 |
| Crystal size | 0.10 × 0.10 × 0.05 mm$^3$ |
| Theta range for data collection | 2.41–44.11° |

TABLE 3-continued

Crystal data and structure refinement for [PQT ⊂ 2] · 2PF$_6$.

| | |
|---|---|
| Index ranges | –9 <= h <= 9, –15 <= k <= 15, –16 <= l <= 17 |
| Reflections collected | 9915 |
| Independent reflections | 4650 [R(int) = 0.0554] |
| Completeness to theta = 44.11° | 88.7% |
| Absorption correction | None |
| Refinement method | Full-matrix least-squares on F$^2$ |
| Data/restraints/parameters | 4650/65/620 |
| Goodness-of-fit on F$^2$ | 1.061 |
| Final R indices [I > 2sigma(I)] | R$_1$ = 0.0961, wR$_2$ = 0.2298 |
| R indices (all data) | R$_1$ = 0.1306, wR$_2$ = 0.2525 |
| Largest diff. peak and hole | 0.771 and –0.447 e.Å$^{-3}$ |

Experimental and Refinement Details for MOF-1000

A light yellow block shaped crystal (0.20×0.20×0.10 mm$^3$) of MOF-1000 was placed in a 0.4 mm diameter borosilicate capillary along with a small amount of mother liquor. The capillary was flame sealed and mounted on a SMART APEXII three circle diffractometer equipped with a CCD area detector and operated at 1200 W power (40 kV, 30 mA) to generate Cu Kα radiation (λ=1.5418 Å) while being cooled to 258(2) K in a liquid N2 cooled stream of nitrogen. After a preliminary unit cell parameters check, the data collection strategy for MOF-1000 was refined by the APEX2 software suite according to the desired completeness and redundancy (desired completeness: 100%, desired redundancy: 4). In total, 5053 frames were collected under the strategy of overlapping φ and ω scans at different detector (2θ) settings in 53 hours. Exhaustive reviewing of collected frames showed the unit cell parameters change gradually during the data collection. Table 4 shows that different unit cell parameters were obtained when frames from different time segments were selected. Data from two other crystals from different batches were collected at different temperatures 258 and 233 K), and similar change was observed. No clear pattern for the change in unit cell parameters was observed. In order to achieve better structure determination and refinement, only data from the first 28 hours was used, which shows less inconsistency in the unit cell parameters. A total of 124606 reflections were collected, of which 49574 were unique and 31233 of these were greater than 2σ(I). The range of θ was from 1.67 to 45.13°. The program Scale was performed to minimize differences between symmetry-related or repeated reflections.

TABLE 4

Different unit cell parameters were obtained when frames from different time segments were selected for MOF-1000.

| Time | a (Å) | b (Å) | c (Å) | α (°) | β (°) | γ (°) |
|---|---|---|---|---|---|---|
| 0–11 h | 26.41 | 26.47 | 52.62 | 90.78 | 90.46 | 91.95 |
| 11–28 h | 26.32 | 26.47 | 52.50 | 91.07 | 90.61 | 92.17 |
| 28–43 h | 26.41 | 26.61 | 53.47 | 90.15 | 93.64 | 93.01 |
| 43–53 h | 26.13 | 26.44 | 52.70 | 90.43 | 95.82 | 93.28 |

The structure was solved in the triclinic P1 space group with Z=2 using direct methods. All non-hydrogen atoms were refined isotropically with hydrogen atoms generated as spheres riding the coordinates of their parent atoms. The center benzene ring and methoxy groups show a high degree of disorder due to the length of the strut. MOF-1000 contains three struts per Zn4O secondary building unit. In every Zn$_4$O secondary unit, one zinc atom is octahedral, to which two diethylformamide molecules are bonded in addition to four oxygen atoms, while the three other zinc atoms are tetrahedral. Due to the low data quality and the inconsistent unit cell parameters during the data collection, only some of the diethylformamide molecules can be located, while others show only parts of diethylformamide molecules. The attempts made to model solvent molecules did not lead to identification of guest entities in all structures. Since the solvent is not bonded to the framework, this can be expected for the MOF structures. Very high displacement parameters, high esd's and partial occupancy due to the disorder make it impossible to determine accurate positions for solvent molecules. Nonetheless, assignment and refinement of the framework of MOF-1000 were unambiguous. Given the magnitude of MOF-1000, the porosity, and the population with highly disordered guest molecules, the final refined structures have, expectedly, elevated reliability factors compared to those from small molecule crystallography. The structure was reported to display the framework of MOF-1000 as isolated in the crystalline form. The structure is a 4-fold interpenetrating primitive cubic framework. To prove the correctness of the atomic positions in the framework, the application of the SQUEEZE routine of A. Spek has been performed. However atomic co-ordinates for the "non-SQUEEZE" structures are also presented. The program SQUEEZE failed when all the atoms were included due to the huge number of atoms in the unit cell. Solvents coordinated to the Zn4O clusters and all hydrogen atoms were removed before the SQUEEZE routine. Thus the structure reported after SQUEEZE does not include any hydrogen atoms and solvents. Final full matrix least-squares refinement on F2 converged to R1=0.1030 (F>2σ(F)) and wR2=0.2996 (all data) with GOF=1.000. For the structure where the SQUEEZE program has not been employed, final full matrix least-squares refinement on F2 converged to R1=0.2046 (F>2σ(F)) and wR2=0.5392 (all data) with GOF=1.972.

TABLE 5

Crystal Data and Structure of MOF-1000

| | |
|---|---|
| Empirical formula | C342 H202 N6 O85 Zn16 |
| Formula weight | 6801.02 |
| Temperature | 258(2) K |
| Wavelength | 1.54178 Å |
| Crystal system | Triclinic |
| Space group | P$\bar{1}$ |
| Unit cell dimensions | a = 26.4452(15) Å α = 90.895(2)° |
| | b = 26.4452(15) Å β = 90.895(2)° |
| | c = 52.740(3) Å γ = 91.78° |
| Volume | 36857(4) |
| Z | 2 |
| Density (calculated) | 0.613 Mg/m$^3$ |
| Absorption coefficient | 0.860 mm$^{-1}$ |
| F(000) | 6912 |
| Crystal size | 0.20 × 0.20 × 0.10 mm$^3$ |
| Theta range for data collection | 1.67-45.13° |
| Index ranges | −24 <= h <= 19, −23 <= k <= 23, −46 <= l <= 48 |
| Reflections collected | 124606 |
| Independent reflections | 49574 [R(int) = 0.0590] |
| Completeness to theta = 45.13° | 82.7% |
| Absorption correction | None |
| Refinement method | Full-matrix least-squares on F$^2$ |
| Data/restraints/parameters | 49574/262/1825 |
| Goodness-of-fit on F$^2$ | 1.972 |
| Final R indices [I > 2sigma(I)] | R$_1$ = 0.2046, wR$_2$ = 0.5159 |
| R indices (all data) | R$_1$ = 0.2399, wR$_2$ = 0.5392 |
| Largest diff. peak and hole | 1.963 and −1.050 e.Å$^{-3}$ |

TABLE 6

Crystal Data and Structure MOF-1000 (SQUEEZE)

| | |
|---|---|
| Empirical formula | C312 O76 Zn16 |
| Formula weight | 6009.04 |
| Temperature | 258(2) K |
| Wavelength | 1.54178 Å |
| Crystal system | Triclinic |
| Space group | P$\bar{1}$ |
| Unit cell dimensions | a = 26.4452(15) Å α = 90.895(2)° |
| | b = 26.4452(15) Å β = 90.895(2)° |
| | c = 52.740(3) Å γ = 91.78° |
| Volume | 36857(4) |
| Z | 2 |
| Density (calculated) | 0.541 Mg/m$^3$ |
| Absorption coefficient | 0.824 mm$^{-1}$ |
| F(000) | 5920 |
| Crystal size | 0.20 × 0.20 × 0.10 mm$^3$ |
| Theta range for data collection | 1.67-45.13° |
| Index ranges | −24 <= h <= 19, −23 <= k <= 23, −46 <= l <= 48 |
| Reflections collected | 124606 |
| Independent reflections | 49574 [R(int) = 0.0525] |
| Completeness to theta = 45.13° | 82.7% |
| Absorption correction | None |
| Refinement method | Full-matrix least-squares on F$^2$ |
| Data/restraints/parameters | 49574/220/1601 |
| Goodness-of-fit on F$^2$ | 1.000 |
| Final R indices [I > 2sigma(I)] | R$_1$ = 0.1030, wR$_2$ = 0.2795 |
| R indices (all data) | R$_1$ = 0.1268, wR$_2$ = 0.2996 |
| Largest diff. peak and hole | 1.179 and −0.701 e.Å$^{-3}$ |

Experimental and Refinement Details for BORG-1A

A light yellow hexagonal shaped crystal (0.30×0.30×0.10 mm3) of BORG-1A was placed in a 0.5 mm diameter borosilicate capillary along with a small amount of mother liquor. The capillary was flame sealed and mounted on a SMART APEXII three circle diffractometer equipped with a CCD area detector and operated at 1200 W power (40 kV, 30 mA) to generate Cu Kα radiation (λ=1.5418 Å) while being cooled to 258(2) K in a liquid N2 cooled stream of nitrogen. Full hemispheres of data were collected using the Bruker APEX2 software suite to carry out overlapping φ and ω scans at three different detector (2θ) settings (2θ=28, 60, 100°). A total of 35903 reflections were collected of which 5845 were unique and 4142 of these were greater than 2σ(I). The range of θ was from 1.44 to 42.62°. Analysis of the data showed negligible decay during collection. The program Scale was performed to minimize differences between symmetry related or repeated reflections.

The structure was solved in the trigonal Pspace group with Z=6 using direct methods. All non-hydrogen atoms in the backbone of the framework were refined anisotropically with hydrogen atoms generated as spheres riding the coordinates of their parent atoms. Due to the highly porosity of the BORG-1A structure, bisparaphenylene-[34]-crown-10 (BPP34C10) crown ethers were surrounded by all the guest entities. Even though the crown ether was chemically bonded to the backbone of the link, the macrocycle with 34 atoms shows extremely flexibility in the uncomplexed form and there can be many conformations. Several disordered atoms were located from macrocycles (O11, C12, C13, O13, C14, O60, C61, C62, O62, C63 and O64), and stable isotropic refinement was achieved. Macrocycle atoms relatively far away from the backbone have higher displacement parameters, indicating an elevated degree of disorder, probably including both static disorder and dynamic disorder. Attempts to determine the positions of hydroquinone rings and other bismethylenedioxy units of the tetraethylene glycol loops in the crown ethers did not lead to positive identification due to the highly disordered crown ether with limited periodicity. The attempts made to model solvent molecules did not lead to identification of guest entities. Since the solvent is not bonded to the framework, this can be expected for the BORG structures. Very high displacement parameters, high esd's and partial occupancy due to the disorder made it impossible to determine accurate positions for solvent molecules. Nonetheless, assignment and refinement of the backbone framework and partial crown ether segments of BORG-1A was unambiguous, as judged by the resulting bond and angle metrics. Given the magnitude of BORG-1A, its high porosity, and population with highly disordered crown ethers and guest molecules, the final refined structure has, expectedly, elevated reliability factors compared to those from small molecule crystallography.

The structure was reported to display the backbone framework and partial crown ether segments for BORG-1A as isolated in the crystalline form. BORG-1A contains three links per Zn4O secondary building unit. The structure is a 3-fold interpenetrating cubic framework with centers of their SBUs aligned along the body diagonal of the cube. To prove the correctness of the atomic positions in the framework the application of the SQUEEZE routine of A. Spek has been performed, and both backbone frameworks and partial ethylene glycol segments have been included. However atomic co-ordinates for the "non-SQUEEZE" structures are also presented. Final full matrix least-squares refinement on F2 converged to R1=0.0780 (F>2σ(F)) and wR2=0.2271 (all data) with GOF=1.036. For the structure where the SQUEEZE program has not been employed, final full matrix least-squares refinement on F2 converged to R1=0.1449 (F>2σ(F)) and wR2=0.4189 (all data) with GOF=1.792. When only framework atoms were included in the latter structure factor calculation, the residual electron density in the F-map was located within the pores of BORG-1A.

The empirical formula from crystal structure refinement is $C_{26}H_8O_{5.17}Zn_{1.33}$, with a density of 0.396 g cm$^{-3}$. This model only contains parts of crown ether segments. If all the atoms in the framework are considered, the calculated empirical formula is $C_{46}H_{46}O_{14.33}Zn_{1.33}$, with a density of 0.739 g cm$^{-3}$.

TABLE 7

Crystal Data and Structure for BORG-1A

| | |
|---|---|
| Empirical formula | C25.5 H8 O5.58 Zn1.33 |
| Formula weight | 490.84 |
| Temperature | 258(2) K |
| Wavelength | 1.54178 Å |
| Crystal system | Trigonal |
| Space group | P$\bar{3}$ |
| Unit cell dimensions | a = 22.5541(3) Å α = 90° |
| | b = 22.5541(3) Å β = 90° |
| | c = 30.6820(10) Å γ = 120° |
| Volume | 12344.5(5) |
| Z | 6 |
| Density (calculated) | 0.396 Mg/m$^3$ |
| Absorption coefficient | 0.598 mm$^{-1}$ |
| F(000) | 1472 |
| Crystal size | 0.30 × 0.30 × 0.10 mm$^3$ |
| Theta range for data collection | 1.44-42.62° |
| Index ranges | −18 <= h <= 18, −18 <= k <= 17, −26 <= l <= 26 |
| Reflections collected | 35903 |
| Independent reflections | 5845 [R(int) = 0.0385] |
| Completeness to theta = 42.62° | 100.0% |
| Absorption correction | None |
| Refinement method | Full-matrix least-squares on F$^2$ |
| Data/restraints/parameters | 5845/78/308 |
| Goodness-of-fit on F$^2$ | 1.792 |
| Final R indices [I > 2sigma(I)] | R$_1$ = 0.1449, wR$_2$ = 0.3859 |
| R indices (all data) | R$_1$ = 0.1704, wR$_2$ = 0.4189 |
| Largest diff. peak and hole | 1.389 and −0.408 e.Å$^{-3}$ |

TABLE 8

Crystal Data and Structure BORG-1A (SQUEEZE)

| | |
|---|---|
| Empirical formula | C25.5 H8 O5.58 Zn1.33 |
| Formula weight | 490.84 |
| Temperature | 258(2) K |
| Wavelength | 1.54178 Å |
| Crystal system | Trigonal |
| Space group | P$\bar{3}$ |
| Unit cell dimensions | a = 22.5541(3) Å α = 90° |
| | b = 22.5541(3) Å β = 90° |
| | c = 30.6820(10) Å γ = 120° |
| Volume | 12344.5(5) |
| Z | 6 |
| Density (calculated) | 0.396 Mg/m$^3$ |
| Absorption coefficient | 0.598 mm$^{-1}$ |
| F(000) | 1472 |
| Crystal size | 0.30 × 0.30 × 0.10 mm$^3$ |
| Theta range for data collection | 1.44-42.62° |
| Index ranges | −18 <= h <= 18, −18 <= k <= 17, −26 <= l <= 26 |
| Reflections collected | 35903 |
| Independent reflections | 5845 [R(int) = 0.0446] |
| Completeness to theta = 42.62° | 100.0% |
| Absorption correction | None |
| Refinement method | Full-matrix least-squares on F$^2$ |
| Data/restraints/parameters | 5845/78/308 |
| Goodness-of-fit on F$^2$ | 1.036 |
| Final R indices [I > 2sigma(I)] | R$_1$ = 0.0780, wR$_2$ = 0.2159 |
| R indices (all data) | R$_1$ = 0.0890, wR$_2$ = 0.2271 |
| Largest diff. peak and hole | 0.990 and −0.286 e.Å$^{-3}$ |

Experimental and Refinement Details for BORG-1

A light yellow cubic crystal (0.45×0.45×0.45 mm$^3$) of BORG-1 was placed in a 0.6 mm diameter borosilicate capillary along with a small amount of mother liquor. The capillary was flame sealed and mounted on a SMART APEXII three circle diffractometer equipped with a CCD area detector and operated at 1200 W power (40 kV, 30 mA) to generate Cu Kα radiation (λ=1.5418 Å) while being cooled to 258(2) K in a liquid N$_2$ cooled stream of nitrogen. After a preliminary unit cell check of parameters, the data collection strategy for BORG-1 was refined by the APEX2 software suite for the desired completeness and redundancy (desired completeness: 100%, desired redundancy: 4). In total, 2591 frames were collected with overlapping φ and ω scans at different detector (2θ) settings. A total of 57237 reflections were collected, of which 1508 were unique and 1098 of these were greater than 2σ(I). The range of θ was from 1.45 to 33.90°. Analysis of the data showed crystal decomposition during collection due to solvent loss. Linear dependence of the frame number on crystal decomposition was counted by B-value refinement when the program Scale was performed by the APEX2 software.

The structure was solved in the cubic Fm3m space group with Z=8 using direct methods. Zn1, Zn2, O1, O2, O3, C1, C5 and C6 have been refined anisotropically, while other non-hydrogen atoms that could be located have been refined isotropically, with hydrogen atoms generated as spheres riding the coordinates of their parent atoms. Zinc and carboxyl oxygen atoms in inorganic building blocks were disordered over two sites respectively. Relative occupancy was fixed during the refinement to avoid correlation with displacement parameters. These optimized occupancy values were assigned by making the anisotropic Uij components of the atoms in the two parts approximately within the same range. In addition, the phenylene rings connected to carboxyl groups were refined as disordered over two sites with equal occupancy. It was assumed that the rotational energy barrier of the center phenylene ring moiety could be low and might have many conformers with various dihedral angles between the center phenylene ring and phenylene rings on either side. Thus severe disorder in the center phenylene ring was also expected, and this allowed a more severe disorder of the tetraethylene glycol loops in the uncomplexed crown ethers. As a result, high displacement parameters for atoms from the center phenyl ring (C8, C9) were to be expected. Hydrogen atoms were added as spheres riding the coordinates of C9, even though only half of the C9 atoms were bonded to hydrogen, while the other half of the C9 atoms were bonded to the tetraethylene glycol loops. Furthermore, due to the high porosity of the BORG-1 structure (a=52.9345(7) Å), crown ethers were surrounded by all the guest entities. Attempts to determine the positions of the hydroquinone rings and the other bismethylenedioxy units of the tetraethylene glycol loops in the crown ethers did not lead to positive identification due to the highly disordered crown ethers with limited periodicity in the highly porous structure. The attempts made to model the solvent molecules also did not lead to identification of the guest entities. Very high displacement parameters, high esd's and partial occupancy due to the disorder made it impossible to determine accurate positions for the solvent molecules. Thus, electron density within void spaces which could not be assigned to any definite entity was modeled as isolated carbon atoms (C1S, C2S, C3S, C4S and C5S), and the foremost errors in all the models lay with assignment of crown ethers and guest electron density. Given the size of BORG-1, the high porosity, and population with highly disordered crown ethers and guest molecules, the final refined structures had, expectedly, elevated reliability factors compared to those from small molecule crystallography.

The structure was reported to display the backbone framework for BORG-1 as isolated in the crystalline form, although it cannot be a structure with accurate bond lengths and bond angles. Other supporting characterization data (vide infra Materials and Methods) are consistent with the crystal structure. BORG-1 contains three links per Zn4O secondary building unit. The structure is a non-interpenetrating cubic framework. To prove the correctness of the atomic positions in the framework the application of the SQUEEZE routine of A. Spek has been performed with the backbone framework only. However, atomic co-ordinates for the "non-SQUEEZE" structures are also presented. Final full matrix least-squares refinement on F2 converged to R1=0.0737 (F>2σ(F)) and wR2=0.2588 (all data) with GOF=1.042. For the structure where the SQUEEZE program has not been employed, final full matrix least-squares refinement on F2 converged to R1=0.2884 (F>2σ(F)) and wR2=0.6396 (all data) with GOF=3.094. When only framework atoms were included in the latter structure factor calculation, the residual electron density in the F-map was located within the pores of BORG-1.

The empirical formula from the crystal structure refinement is $C_{72}H_{36}O_{13}Zn_4$ (without any guest molecule), with a density of 0.123 g cm$^{-3}$. This model only contains the backbone of the framework. If all the atoms in the framework are considered, the calculated empirical formula is $C_{138}H_{138}O_{43}Zn_4$, with a density of 0.246 g cm$^{-3}$.

TABLE 9

Crystal Data and Structure for BORG-1

| | |
|---|---|
| Empirical formula | C81 H36 O13 Zn4 |
| Formula weight | 1478.58 |
| Temperature | 258(2) K |
| Wavelength | 1.54178 Å |
| Crystal system | Cubic |
| Space group | Fm3̄m |
| Unit cell dimensions | a = 52.9345(7) Å α = 90° |
| | b = 52.9345(7) Å β = 90° |
| | c = 52.9345(7) Å γ = 90° |
| Volume | 148326(3) |
| Z | 8 |
| Density (calculated) | 0.132 Mg/m$^3$ |
| Absorption coefficient | 0.196 mm$^{-1}$ |
| F(000) | 5968 |
| Crystal size | 0.45 × 0.45 × 0.45 mm$^3$ |
| Theta range for data collection | 1.45-33.90° |
| Index ranges | -37 <= h <= 37, -34 <= k <= 37, -38 <= l <= 38 |
| Reflections collected | 57237 |
| Independent reflections | 1508 [R(int) = 0.1861] |
| Completeness to theta = 33.90° | 99.1% |
| Absorption correction | None |
| Refinement method | Full-matrix least-squares on F$^2$ |
| Data/restraints/parameters | 1508/82/66 |
| Goodness-of-fit on F$^2$ | 3.094 |
| Final R indices [I > 2sigma(I)] | $R_1$ = 0.2884, $wR_2$ = 0.6079 |
| R indices (all data) | $R_1$ = 0.3107, $wR_2$ = 0.6396 |
| Largest diff. peak and hole | 0.882 and -0.549 e.Å$^{-3}$ |

TABLE 10

Crystal Data and Structure for BORG-1 (SQUEEZE)

| | |
|---|---|
| Empirical formula | C72 H36 O13 Zn4 |
| Formula weight | 1370.49 |
| Temperature | 258(2) K |
| Wavelength | 1.54178 Å |
| Crystal system | Cubic |
| Space group | Fm3̄m |
| Unit cell dimensions | a = 52.9345(7) Å α = 90° |
| | b = 52.9345(7) Å β = 90° |
| | c = 52.9345(7) Å γ = 90° |
| Volume | 148326(3) |
| Z | 8 |
| Density (calculated) | 0.123 Mg/m$^3$ |
| Absorption coefficient | 0.192 mm$^{-1}$ |
| F(000) | 5536 |
| Crystal size | 0.45 × 0.45 × 0.45 mm$^3$ |
| Theta range for data collection | 1.45-33.90° |
| Index ranges | -37 <= h <= 37, -34 <= k <= 37, -38 <= l <= 38 |
| Reflections collected | 57237 |
| Independent reflections | 1508 [R(int) = 0.1889] |
| Completeness to theta = 33.90° | 99.1% |
| Absorption correction | None |
| Refinement method | Full-matrix least-squares on F$^2$ |
| Data/restraints/parameters | 1508/82/51 |
| Goodness-of-fit on F$^2$ | 1.042 |
| Final R indices [I > 2sigma(I)] | $R_1$ = 0.0737, $wR_2$ = 0.2462 |
| R indices (all data) | $R_1$ = 0.0820, $wR_2$ = 0.2588 |
| Largest diff. peak and hole | 0.171 and -0.183 e.Å$^{-3}$ |

Experimental Details for BORG-2

A light yellow cubic shape crystal (0.20×0.20×0.20 mm$^3$) of BORG-2 was placed in a 0.4 mm diameter borosilicate capillary along with a small amount of mother liquor. The capillary was flame sealed and mounted on a SMART APEXII three circle diffractometer equipped with a CCD area detector and operated at 1200 W power (40 kV, 30 mA) to generate Cu Kα radiation (λ=1.5418 Å) while being cooled to 258(2) K in a liquid N2 cooled stream of nitrogen. Data were collected using the Bruker APEX2 software suite to carry out overlapping φ and ω scans at two different detector (2θ) settings (2θ=28, 60°). 986 reflections with min. I/sigma 20 were harvested for unit cell determination from a total of 240 frames. The theta range for the unit cell determination is 2.350 to 37.375°. The bravis lattice of cubic F with a=52.9482 Å was chosen (FOM=0.64).

The only optimal BORG-2 crystals suitable for analysis were generally small and weakly diffracting, and unfortunately, larger crystals, which might have improved the quality of the data, presented a lowered degree of crystallinity, and optimization of crystal growing conditions for large high-quality specimens has not yet been fruitful. Analysis of the data showed crystal decomposition during collection. Additionally, diffuse scattering from the highly disordered crown ethers and solvent in the void spaces within the crystal and from the capillary used mount the crystal contributes to the background noise and the 'washing out' of high angle data. A complete structure solution was not obtained due to the high Rint value (0.4205 before scale). Nevertheless, determination of the unit cell parameters was unambiguous. The unit cell constants and the space group information for BORG-2 was nearly identical to that of BORG-1. Thus, atom positions from BORG-1 were used to model BORG-2. BORG-2 contains 1,5-dinaphthoparaphenylene-[36]crown-10 while BORG-1 has bisparaphenylene-[34]-crown-10. This difference in the crown does not change the PXRD simulation pattern, since both BORG-1 and BORG-2 are extremely disordered in the crown part of the structure. The structure of BORG-2 was characterized by powder X-ray diffraction.

TABLE 11

Simulated Atomic Coordinates for BORG-2
Crystal system: Cubic
Space group: Fm$\bar{3}$m (No. 225)
Unit cell parameters: a = 52.9482 Å

|  | x | y | z | s.o.f. |
|---|---|---|---|---|
| Zn1 | 0.728169 | 0.271831 | 0.228169 | 0.08333 |
| O2 | 0.690045 | 0.267476 | 0.232524 | 0.25000 |
| Zn2 | 0.728836 | 0.271164 | 0.271164 | 0.08333 |
| O3 | 0.693782 | 0.264602 | 0.264602 | 0.25000 |
| O1 | 0.750000 | 0.250000 | 0.250000 | 0.04167 |
| C1 | 0.683806 | 0.250000 | 0.250000 | 0.25000 |
| C2 | 0.655102 | 0.250000 | 0.250000 | 0.25000 |
| C3 | 0.641857 | 0.266205 | 0.233795 | 0.25000 |
| H3 | 0.650622 | 0.276972 | 0.223028 | 0.25000 |
| C4 | 0.615487 | 0.266167 | 0.233833 | 0.25000 |
| H4 | 0.606566 | 0.276870 | 0.223130 | 0.25000 |
| C5 | 0.602767 | 0.250000 | 0.250000 | 0.25000 |
| C6 | 0.575671 | 0.250000 | 0.250000 | 0.25000 |
| C7 | 0.554419 | 0.250000 | 0.250000 | 0.25000 |
| C8 | 0.526302 | 0.250000 | 0.250000 | 0.25000 |
| C9 | 0.513538 | 0.233648 | 0.233648 | 0.50000 |
| H9 | 0.522469 | 0.222949 | 0.222949 | 0.50000 |
| C10 | 0.615257 | 0.266005 | 0.266005 | 0.25000 |
| H10 | 0.606347 | 0.276711 | 0.276711 | 0.25000 |
| C11 | 0.642055 | 0.265952 | 0.265952 | 0.25000 |
| H11 | 0.650856 | 0.276704 | 0.276704 | 0.25000 |

Experimental and Simulated Powder X-Ray Diffraction Patterns.

Powder X-ray diffraction (PXRD) data were collected using a Bruker D8-Discover θ-2θ diffractometer in reflectance Bragg-Brentano geometry. Cu Kα radiation (λ=1.5406 Å; 1,600 W, 40 kV, 40 mA) was focused using a planar Gobel Mirror riding the Kα line. A 0.6 mm divergence slit was used for all measurements. Diffracted radiation was detected using a Vantec line detector (Bruker AXS) (6° 2θ sampling width) equipped with a Ni monochromator. All samples were mounted on a glass slide or a zero background quartz plate fixed on a sample holder by dropping crystals and then leveling the sample surface with a wide blade spatula. The best counting statistics were achieved by using a 0.02° 2θ step scan from 2-50° with an exposure time of 0.4 s per step.

Thermal Gravimetric Analysis.

All samples were run on a TA Instruments Q-500 series thermal gravimetric analyzer with samples held in platinum pans in a continuous air flow atmosphere. Samples were heated at a constant rate of 5° C./min during all TGA experiments.

Figure 39:
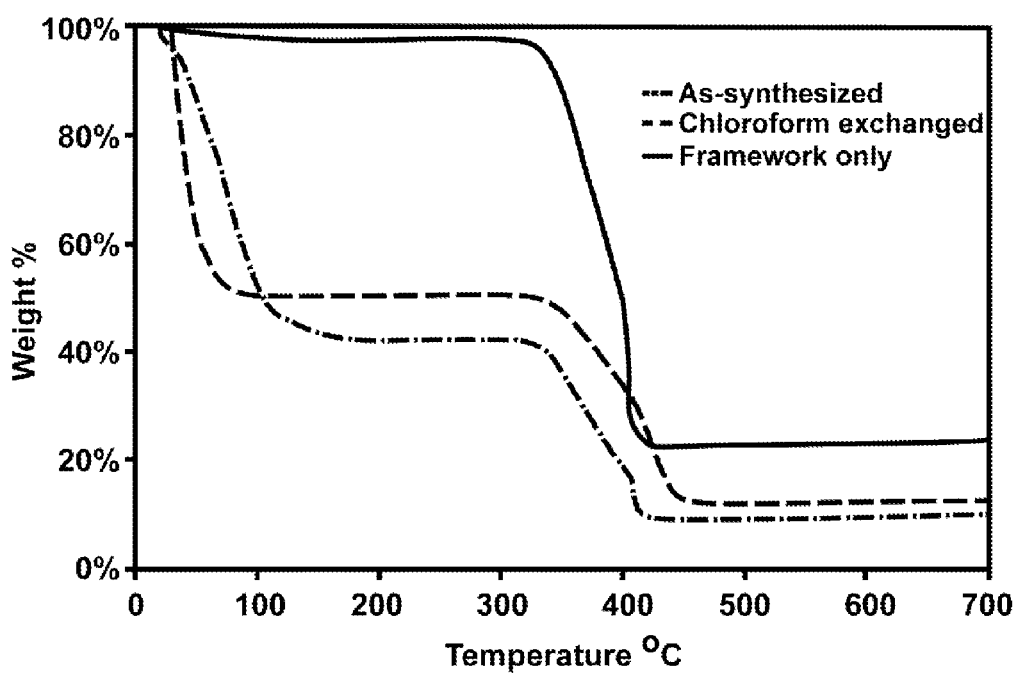
FIG. 39. Shows an overlay of TGA traces of MOF-1000. As-synthesizee, chloroform (pentene stabilized) exchanged, framework only.

The TGA trace of the MOF-1000 (FIG. 39) sample after being CHCl$_3$ (pentene stabilized) exchanged three days, three times each day and evacuated at room temperature for 12 h, is shown. The material is thermally stable to 330° C., and a sharp weight loss from that point onwards indicates the decomposition of the material. This weight-loss step from MOF-1000 to ZnO (77.7%) matches the calculated weight loss (79.0%).

Figure 40:
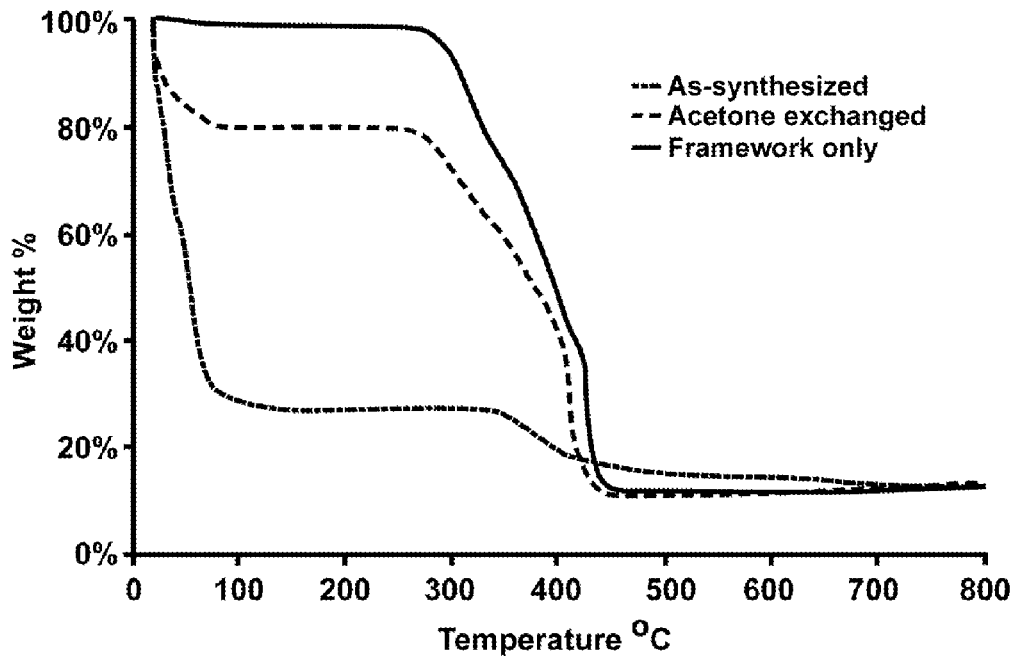
FIG. 40. Shows the overlay of TGA traces of BORG-1. As-synthesized, Me$_2$CO exchanged, framework only.

The TGA trace of the BORG-1 (FIG. 40) sample after being Me$_2$CO exchanged three days, three times each day, and evacuated at room temperature for 12 h, is shown in blue. The material is thermally stable to 300° C., and a sharp weight loss from that point onwards indicates the decomposition of the material. This weight-loss step from BORG-1 to ZnO (86.6%) matches the calculated weight loss (88.2%).

The TGA trace of the BORG-2 (FIG. 41) sample after being Me$_2$CO exchanged three days, three times each day, and evacuated at room temperature for 12 h, is shown. The material is thermally stable to 300° C., and a sharp weight loss from that point onwards indicates the decomposition of the material. This weight-loss step from BORG-2 to ZnO (85.0%) matches the calculated weight loss (88.8%).

A number of embodiments of the invention have been described. Nevertheless, it will be understood that various modifications may be made without departing from the spirit and scope of the invention. Accordingly, other embodiments are within the scope of the following claims.

What is claimed is:

1. A metal organic framework comprising a linking moiety connecting at least two metals, the linking moiety having the structure:

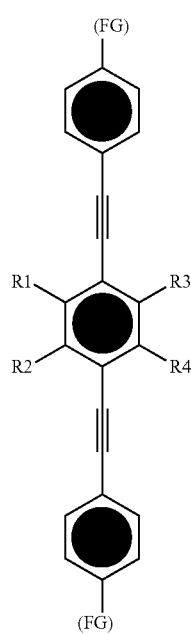

wherein, FG refer to functional linking groups selected from the group consisting of $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $CH(RSH)_2$, $C(RSH)_3$, $CH(RNH_2)_2$, $C(RNH_2)_3$, $CH(ROH)_2$, $C(ROH)_3$, $CH(RCN)_2$, $C(RCN)_3$, $CH(SH)_2$, $C(SH)_3$, $CH(NH_2)_2$, $C(NH_2)_3$, $CH(OH)_2$, $C(OH)_3$, $CH(CN)_2$, and $C(CN)_3$, that undergo condensation with a metal to link the at least two metals, wherein R is an alkyl group having from 1 to 5 carbon atoms, or an aryl group comprising 1 to 2 phenyl rings and wherein the functional linking group forms a coordination complex with the metals; and wherein $R^1$ and $R^4$ are linked together to form a macrocycle and/or wherein $R^2$ and $R^3$ are linked together to form a macrocycle, wherein the macrocycle linking $R^1$ and $R^4$ and/or the macrocycle linking $R^2$ and $R^3$ each comprises seven or more ring atoms.

2. The metal organic framework of claim 1, wherein the macrocycle is selected from the group consisting of a crown ether; and a cyclic macromolecule comprising C, O, N, or S.

3. The metal organic framework of claim 1, wherein the macrocycle is selected from the group consisting of:

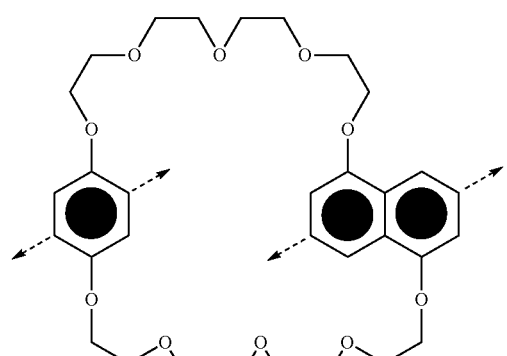

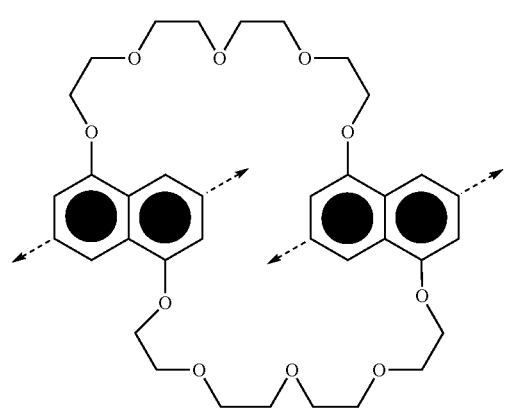

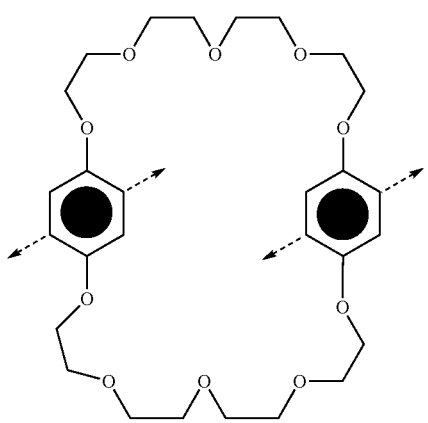

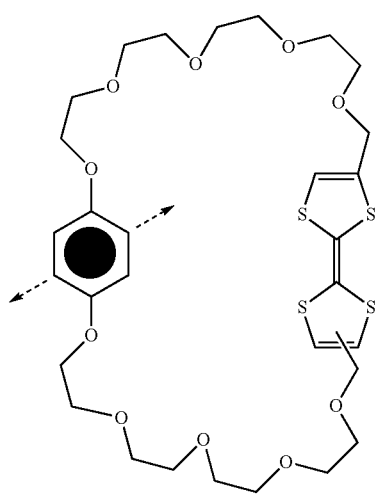

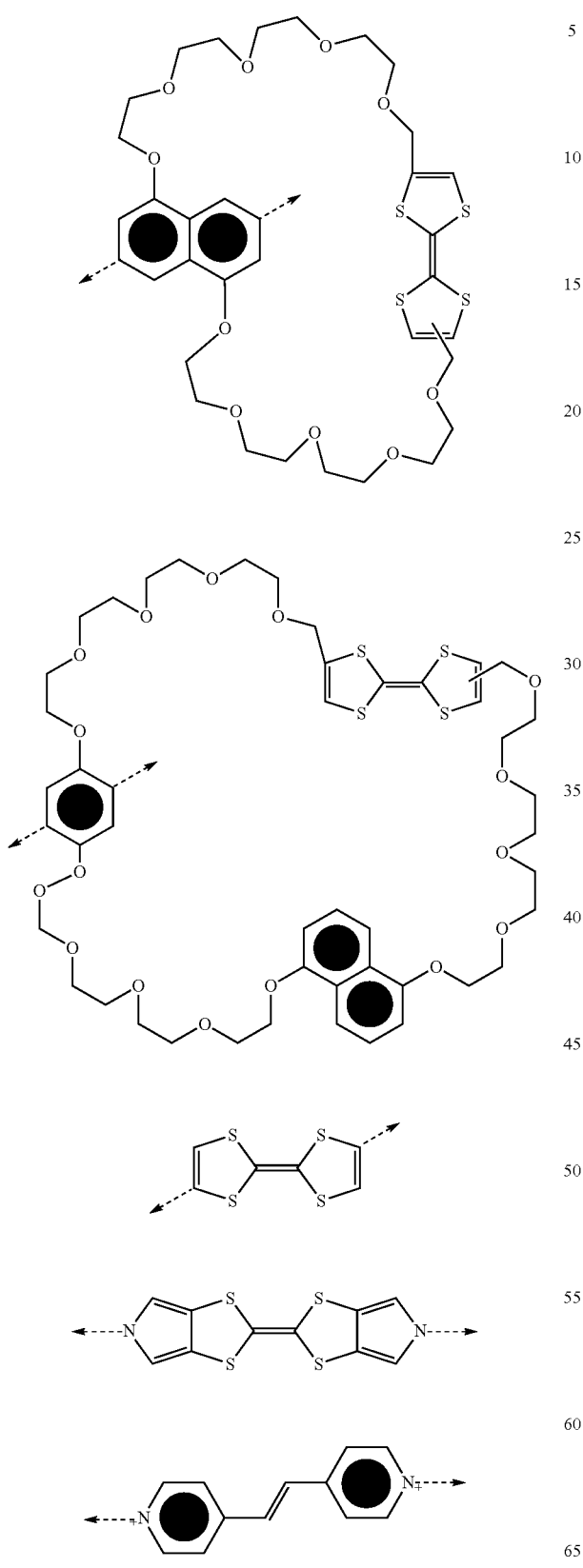
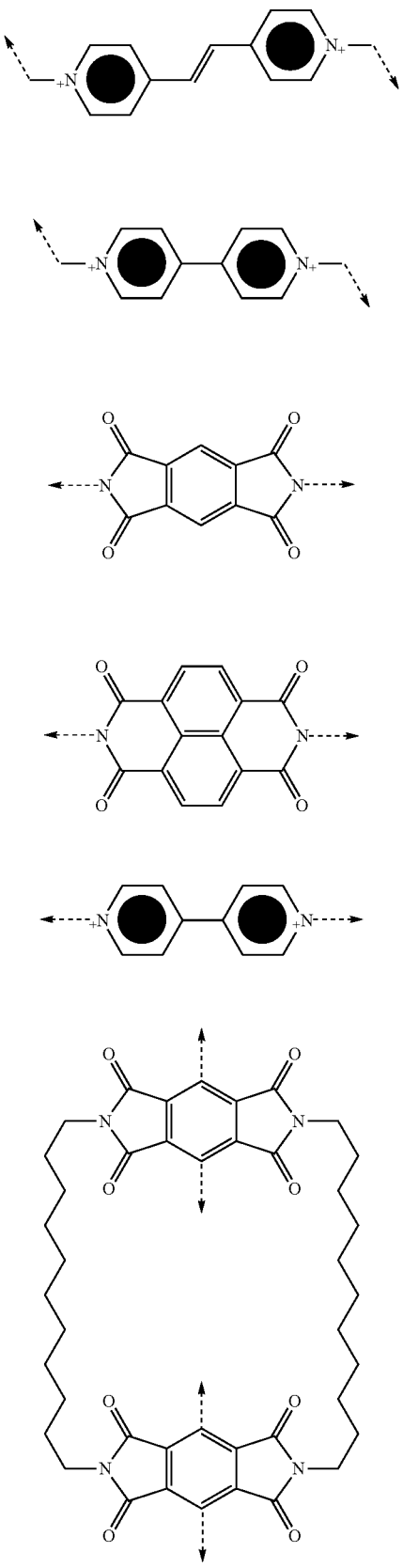

71
-continued
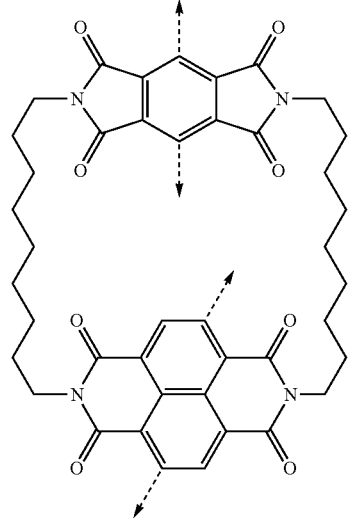
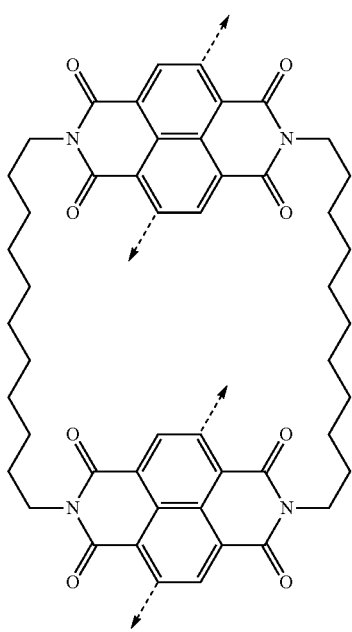
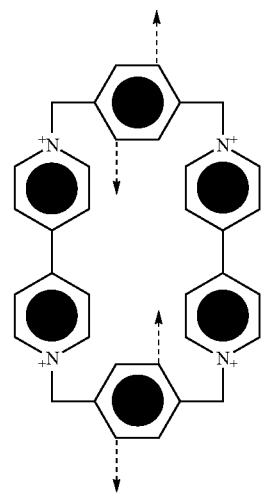
72
-continued
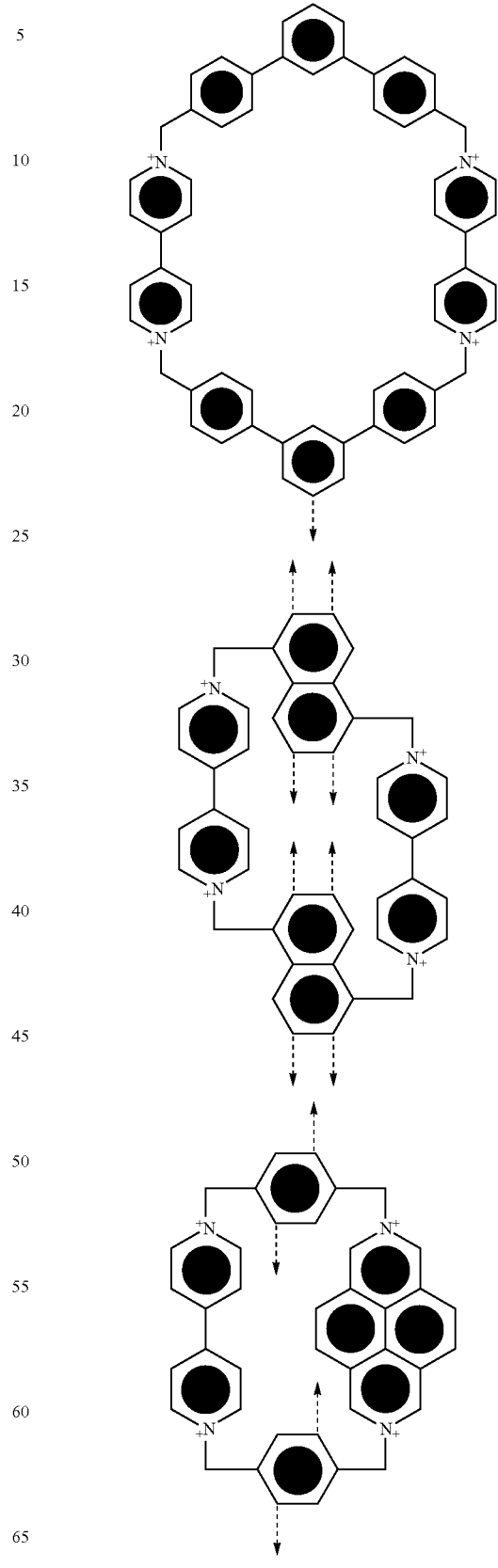

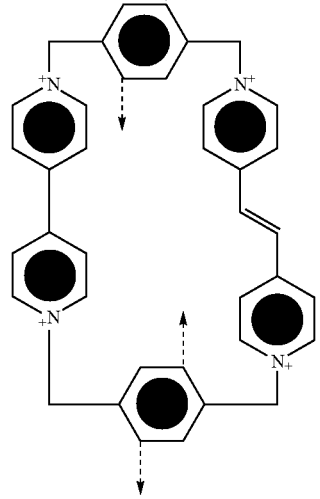

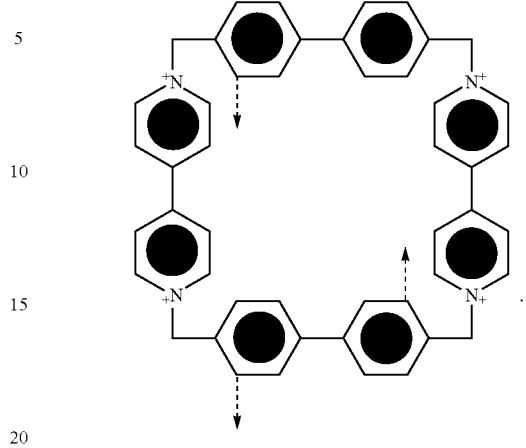

wherein the arrows denote $R^1$ and $R^4$ or $R^2$ and $R^3$ of the linking moiety.

4. The metal organic framework of claim 1, wherein the linking moiety comprising the macrocycle or a functional group moiety with stereospecific and stereoelectronic control comprises a structure selected from the group consisting of structures I, XI-XV and XXVI-XXX or any combination thereof:

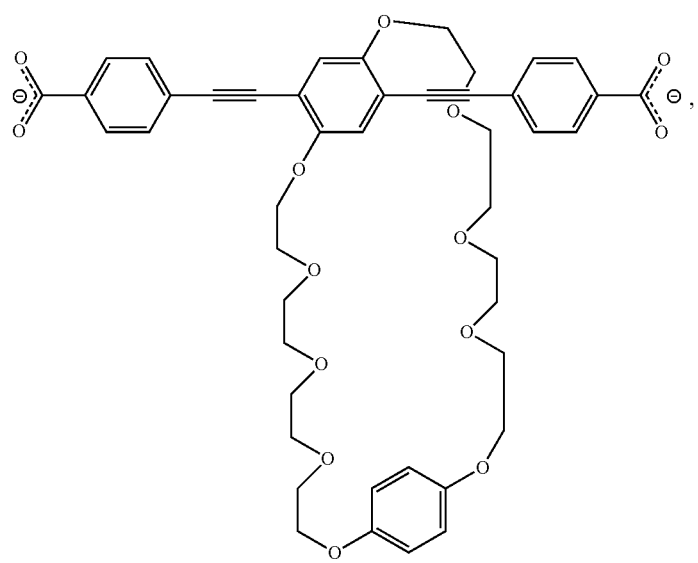

I

XI
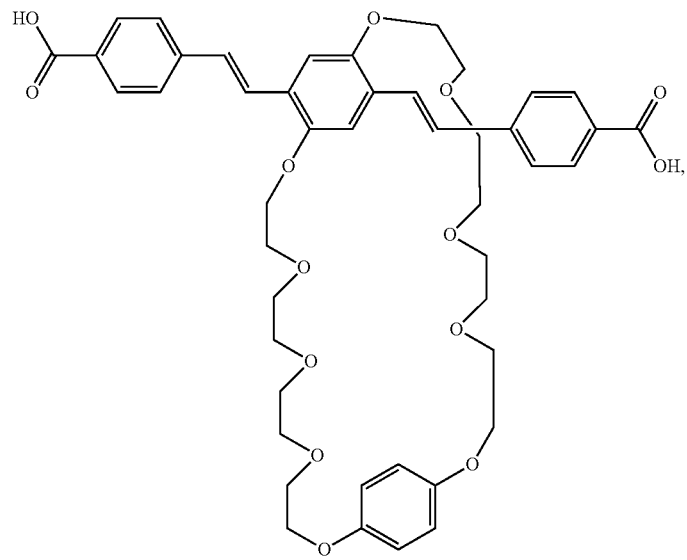
XII
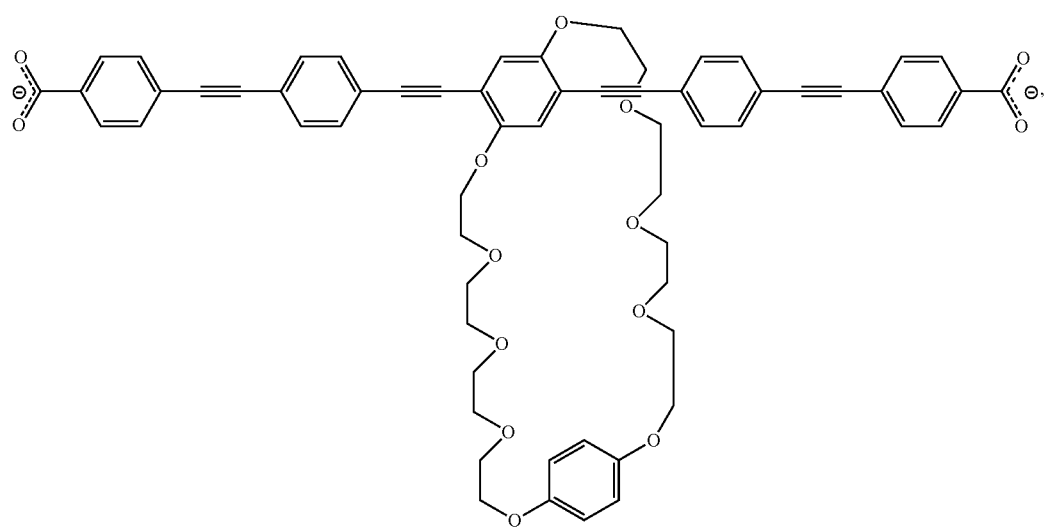

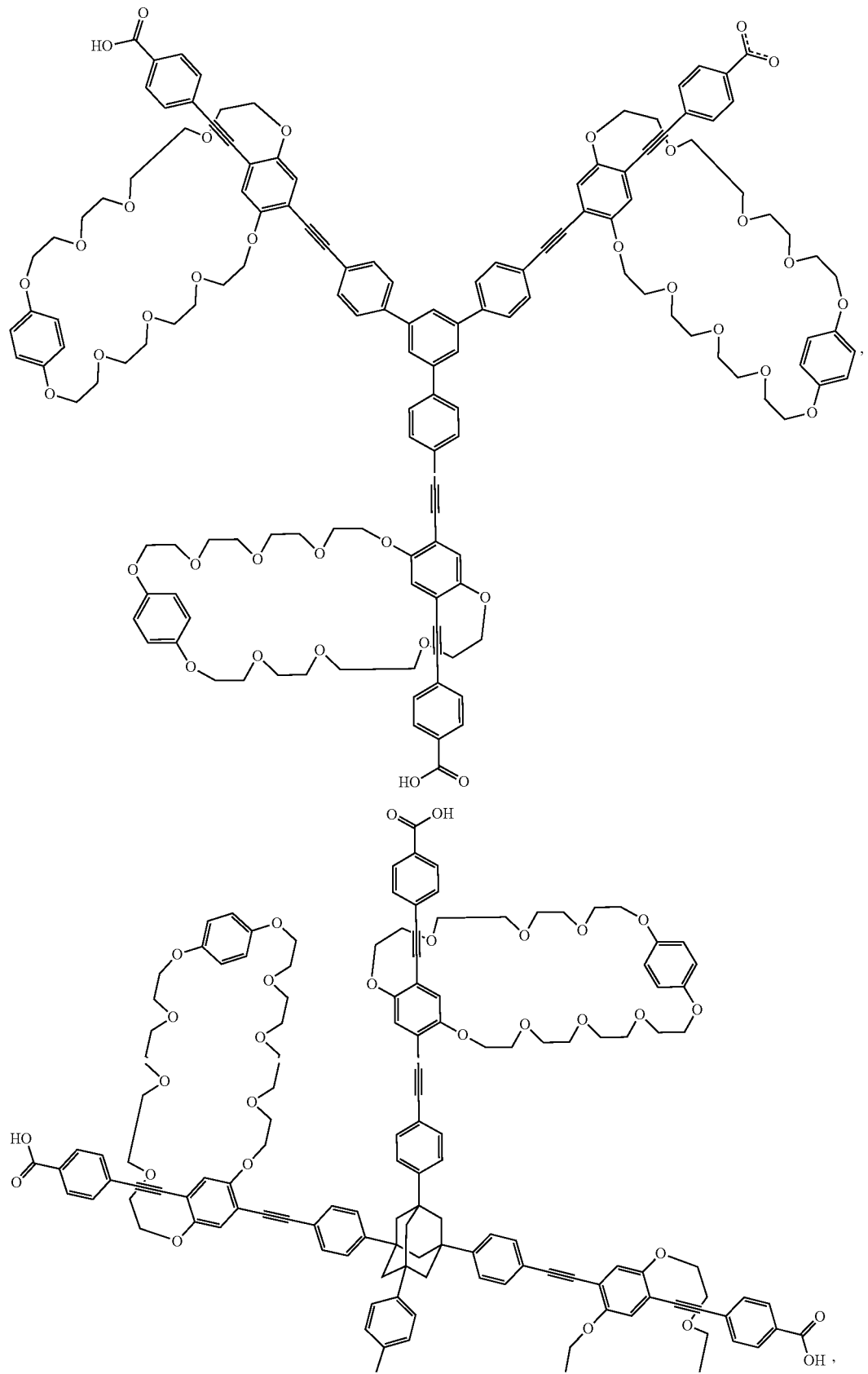

-continued
79
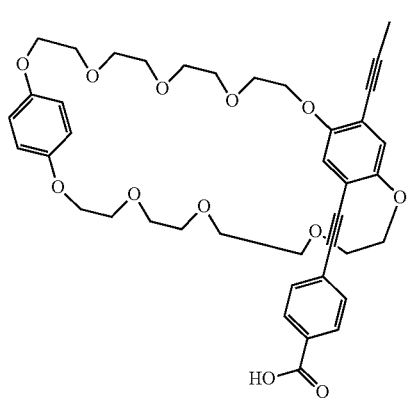
80
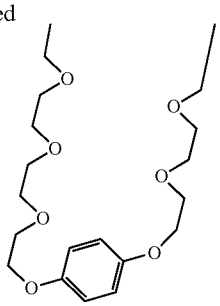
XV
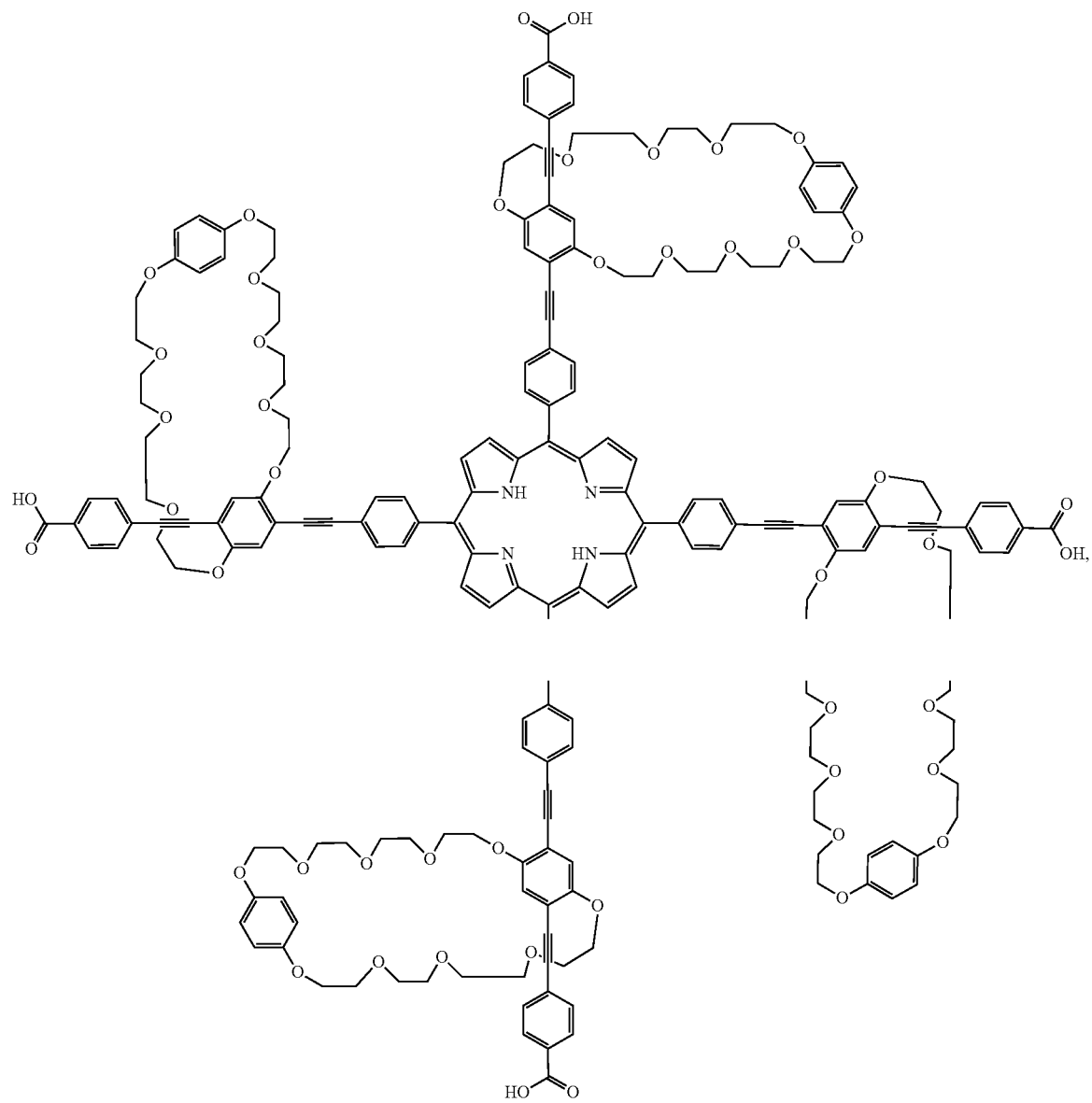

XXVII
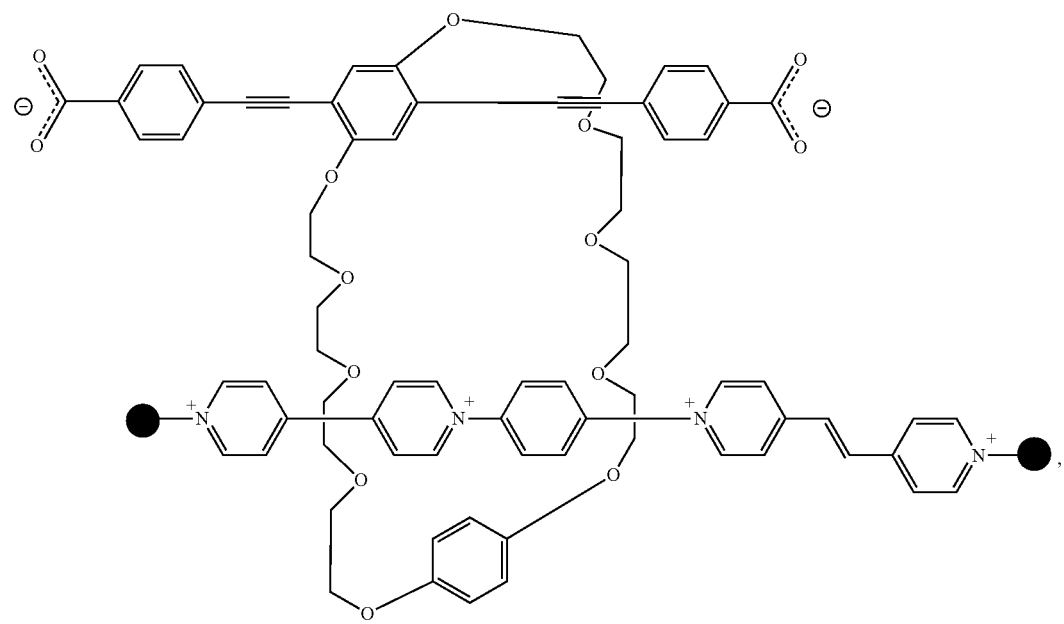
XXVI
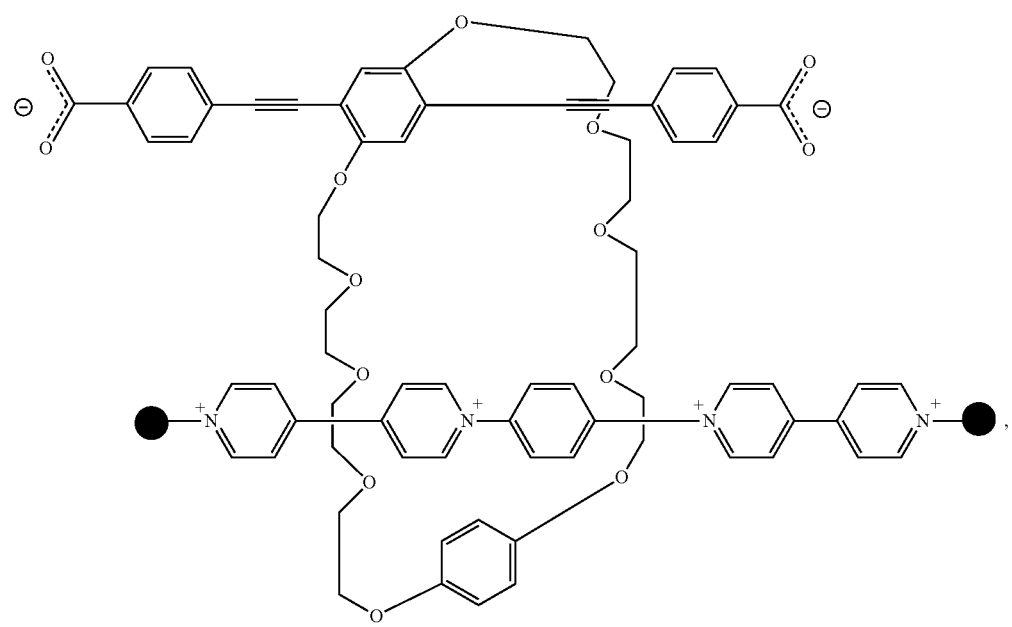

XXVIII
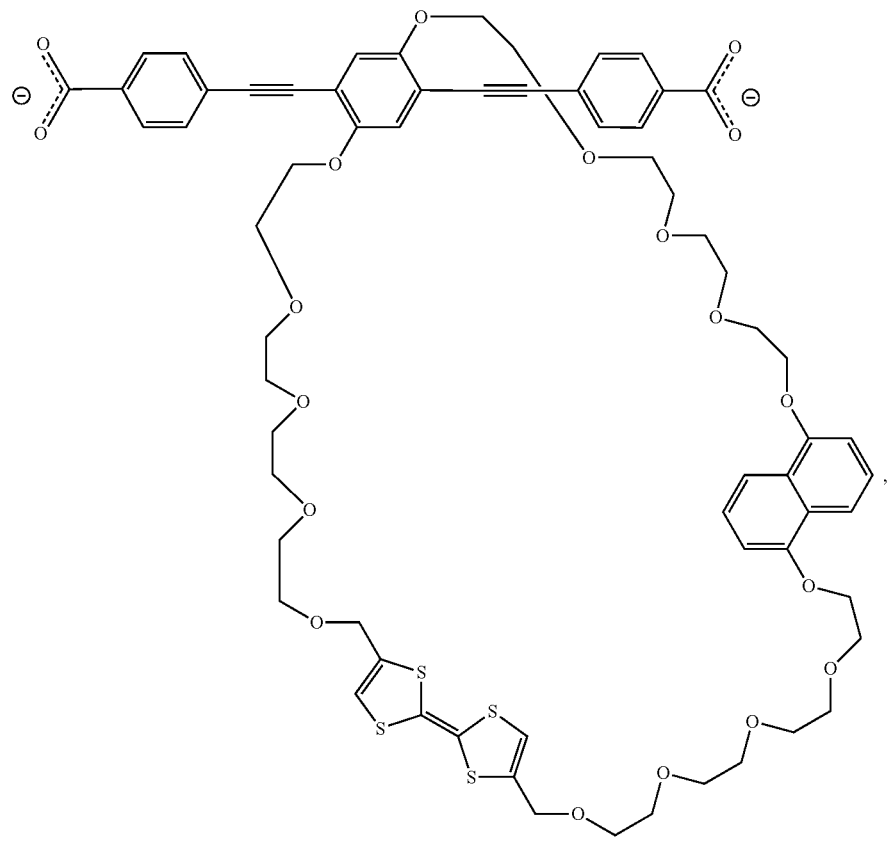
XXIX
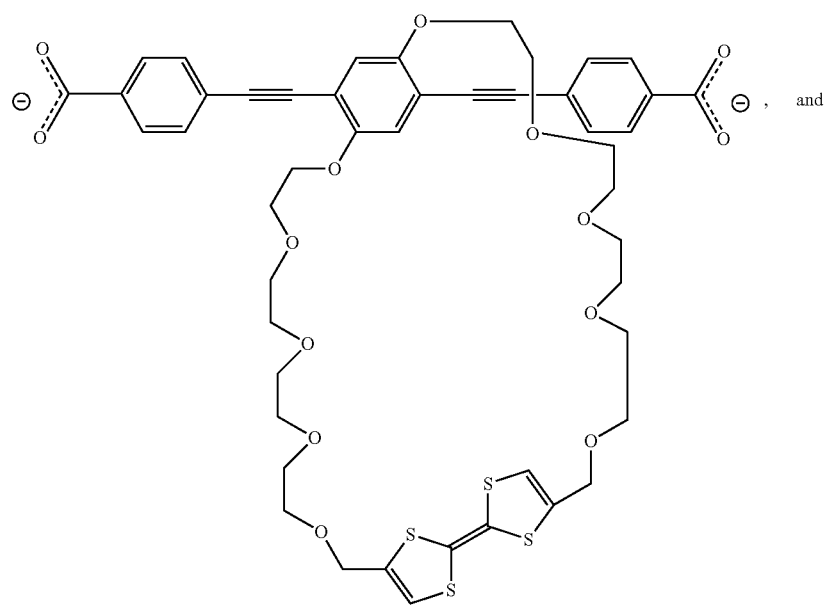, and

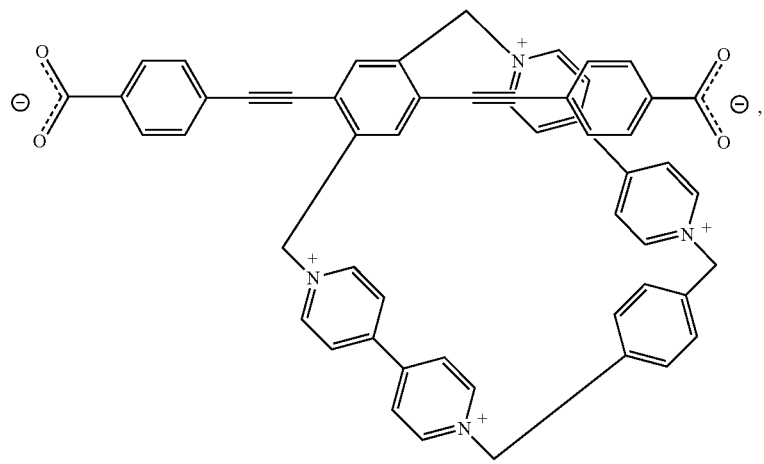

XXX

5. The metal organic framework of claim 1, wherein the metal organic framework comprises a macrocycle selected from the group consisting of pseudorotaxane, rotaxane, catenane, chelates and cryptand.

6. The metal organic framework of claim 5, wherein the catenane framework comprises linking moieties having a structure selected from the group consisting of structures XXXI-XXXIII:

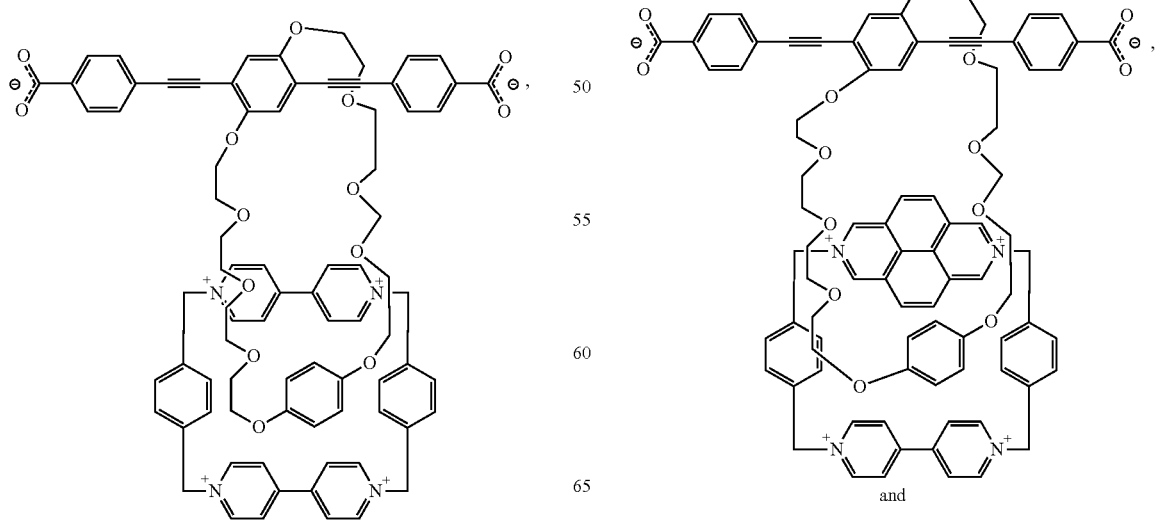

and

XXXIII

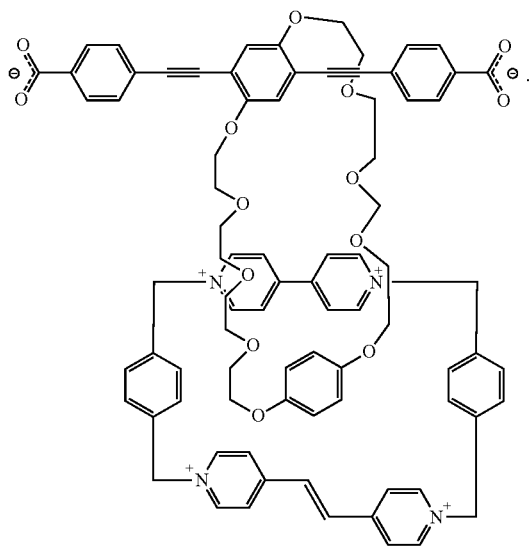

7. The framework of claim 1, wherein the functional linking group comprises a carboxylic acid functional group.

8. The framework of claim 1, wherein the metal is a transition metal.

9. The framework of claim 1, wherein the metal is selected from the group consisting of $Li^+$, $Na^+$, $Rb^+$, $Mg^{2+}$, $Ca^{2+}$, $Sr^{2+}$, $Ba^{2+}$, $Sc^{3+}$, $Ti^{4+}$, $Zr^{4+}$, $Ta^{3+}$, $Cr^{3+}$, $Mo^{3+}$, $W^{3+}$, $Mn^{3+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Ni^{2+}$, $Ni^+$, $Pd^{2+}$, $Pd^+$, $Pt^{2+}$, $Pt^+$, $Cu^{2+}$, $Cu^+$, $Au^+$, $Zn^{2+}$, $Al^{3+}$, $Ga^{3+}$, $In^{3+}$, $Si^{4+}$, $Si^{2+}$, $Ge^{4+}$, $Ge^{2+}$, $Sn^{4+}$, $Sn^{2+}$, $Bi^{5+}$, $Bi^{3+}$, and combinations thereof.

10. A microelectronic switch comprising a metal organic framework of claim 1.

11. The microelectronic switch of claim 10, wherein at least two monodentate or multidentate cores are linked to one another by a structure selected from the group consisting of structures I, XI-XV, and XXVI-XXXIII and any combination thereof.

12. A sensor comprising a framework of claim 1.

13. A gas separation device comprising a framework of claim 1.

14. A small molecule separation/purification device comprising a framework of claim 1.

15. A guest recognition device comprising a framework of claim 1.

16. A chiral molecule separation medium comprising a framework of claim 1.

* * * * *